(12) United States Patent
Gutkind et al.

(10) Patent No.: US 11,679,113 B2
(45) Date of Patent: Jun. 20, 2023

(54) ANTICANCER TREATMENT FOR UVEAL MELANOMA

(71) Applicant: The Regents of the University of California, Oakland, CA (US)

(72) Inventors: Jorge Gutkind, La Jolla, CA (US); David Schlaepfer, La Jolla, CA (US); Justine Paradis, La Jolla, CA (US); Ayush Kishore, La Jolla, CA (US); Monica Acosta, La Jolla, CA (US); Nadia Arang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 352 days.

(21) Appl. No.: 16/824,639

(22) Filed: Mar. 19, 2020

(65) Prior Publication Data

US 2020/0323863 A1    Oct. 15, 2020

Related U.S. Application Data

(60) Provisional application No. 62/832,425, filed on Apr. 11, 2019.

(51) Int. Cl.
| | |
|---|---|
| *A61P 35/04* | (2006.01) |
| *A61K 31/506* | (2006.01) |
| *A61K 31/5355* | (2006.01) |
| *A61K 31/437* | (2006.01) |
| *A61K 31/136* | (2006.01) |
| *A61K 31/4402* | (2006.01) |
| *A61K 31/166* | (2006.01) |
| *A61K 31/4184* | (2006.01) |
| *A61K 31/519* | (2006.01) |
| *A61K 31/44* | (2006.01) |
| *A61K 31/4523* | (2006.01) |
| *A61K 31/53* | (2006.01) |
| *A61K 31/4439* | (2006.01) |
| *A61K 48/00* | (2006.01) |
| *A61K 31/5025* | (2006.01) |

(52) U.S. Cl.
CPC ...... *A61K 31/5355* (2013.01); *A61K 31/5025* (2013.01); *A61K 48/005* (2013.01); *A61P 35/04* (2018.01)

(58) Field of Classification Search
CPC ... A61P 35/04; A61K 31/506; A61K 31/5355; A61K 31/437; A61K 31/136; A61K 31/4402; A61K 31/166; A61K 31/4184; A61K 31/519; A61K 31/44; A61K 31/4523; A61K 31/53; A61K 31/4439
See application file for complete search history.

(56) References Cited

PUBLICATIONS

AACR Annual Meeting 2018, Apr. 14-18, 2018, Chicago, IL, "Targeting FAK inhibits YAP-dependent tumor growth in uveal melanoma."
Feng et al., "A Platform of Synthetic Lethal Gene Interaction Networks Reveals that the GNAQ Uveal Melanoma Oncogene Controls the Hippo Pathway through FAK." Cancer Cell , vol. 35, 2019, p. 457-472.
Feng et al., "A Platform of Synthetic Lethal Gene Interaction Networks Reveals that the GNAQ Uveal Melanoma Oncogene Controls the Hippo Pathway through FAK." Cancer Cell, 2019, Appendix, vol. 35.
Feng et al., "A Platform of Synthetic Lethal Gene Interaction Networks Reveals that the GNAQ Uveal Melanoma Oncogene Controls the Hippo Pathway through FAK." Cancer Cell, 2019, Supplemental Information, vol. 35.
Feng et al., "Graphical abstract GNAQ-FAK-Hippo-XF 1" Cancer Cell, 2019.
Sulzmaier, et al., "FAK in cancer: mechanistic findings and clinical applications", Nat Rev Cancer, Sep. 2014, 14(9); pp. 598-610.

*Primary Examiner* — Brenda L Coleman
(74) *Attorney, Agent, or Firm* — Foley & Lardner LLP

(57) ABSTRACT

Provided herein are methods for treating uveal melanoma in a subject in need thereof by administering an effective amount of an agent that inhibits expression of FAK protein to the subject. In one aspect, the agent that inhibits expression of FAK protein comprises, or alternatively consists essentially of, or yet further consists of a gene editing agent, such as for example one or more of: RNA interference (RNAi), CRISPR/Cas, ZFN, and/or TALEN. In another aspect, the agent is VS-4718. Also described herein are kits comprising, or alternatively consisting essentially of, or yet further consisting of one or more of: agents that inhibit expression of FAK protein, siRNAs, shRNAs, miRNAs, nucleases and/or guide RNA sequences for carrying out the methods of this disclosure, and optional instructions for use.

9 Claims, 19 Drawing Sheets

Specification includes a Sequence Listing.

A

| Oncogenic signatures gene set | Oncogenic signatures gene set (original name) | Score | 0.95 MoE | p value | FDR |
|---|---|---|---|---|---|
| PDGF down-regulated genes | PDGF_UP.V1_DN | -0.864 | 0.184 | 0.001 | 0.200 |
| NRL-KO up-regulated genes | NRL_DN.V1_UP | -0.863 | 0.173 | 0.002 | 0.200 |
| KRAS dependency signature genes | SINGH_KRAS_DEPENDENCY_SIGNATURE_ | -0.863 | 0.184 | 0.003 | 0.200 |
| KRAS up-regulated genes | KRAS.300_UP.V1_UP | -0.851 | 0.172 | 0.006 | 0.225 |
| Rapa up-regulated genes | MTOR_UP.N4.V1_UP | -0.818 | 0.164 | 0.008 | 0.270 |
| IL21 up-regulated genes | IL21_UP.V1_UP | -0.812 | 0.170 | 0.010 | 0.270 |
| YAP conserved signature genes | CORDENONSI_YAP_CONSERVED_SIGNATURE | -0.810 | 0.180 | 0.010 | 0.270 |
| EGFR up-regulated genes | EGFR_UP.V1_UP | -0.800 | 0.179 | 0.012 | 0.270 |
| IL15 up-regulated genes | IL15_UP.V1_UP | -0.778 | 0.166 | 0.014 | 0.270 |
| PTEN-KD up-regulated genes | PTEN_DN.V2_UP | -0.775 | 0.175 | 0.014 | 0.270 |
| RAD001 down-regulated genes | MTOR_UP.V1_DN | -0.736 | 0.183 | 0.019 | 0.318 |
| E2F3 up-regulated genes | E2F3_UP.V1_UP | -0.721 | 0.158 | 0.023 | 0.336 |
| JAK2-KD down-regulated genes | JAK2_DN.V1_DN | -0.718 | 0.178 | 0.024 | 0.336 |
| BMI1-KD up-regulated genes | BMI1_DN_MEL18_DN.V1_UP | -0.716 | 0.168 | 0.025 | 0.336 |
| P53-KD up-regulated genes | P53_DN.V2_UP | -0.710 | 0.180 | 0.029 | 0.360 |
| BRCA1-KD up-regulated genes | BRCA1_DN.V1_DN | -0.686 | 0.156 | 0.033 | 0.388 |
| Up-regulated genes in astroglia cells | CAHOY_ASTROGLIAL | -0.682 | 0.147 | 0.035 | 0.388 |
| KRAS up-regulated genes | KRAS.50_UP.V1_UP | -0.659 | 0.164 | 0.043 | 0.440 |
| TGFB1 down-regulated genes | TGFB_UP.V1_DN | -0.653 | 0.152 | 0.046 | 0.440 |
| Late serum down-regulated genes | CSR_LATE_UP.V1_DN | -0.651 | 0.184 | 0.047 | 0.440 |

B
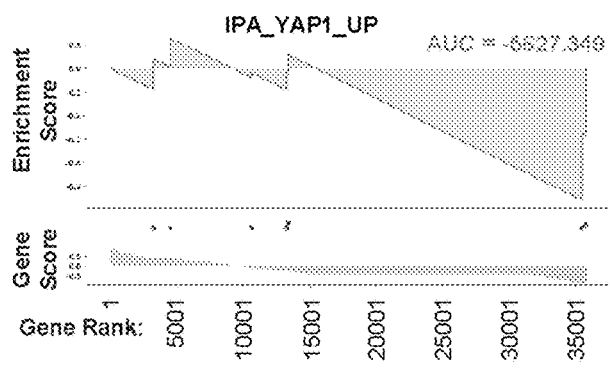

C
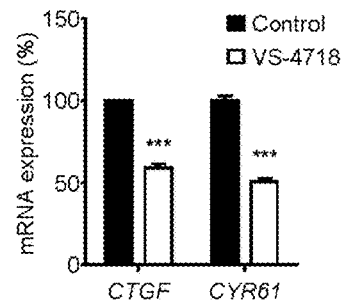

D
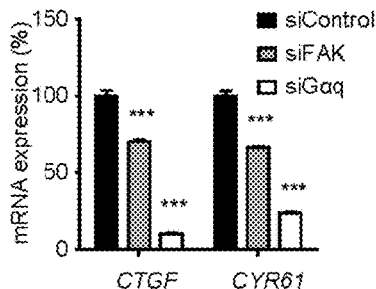

E
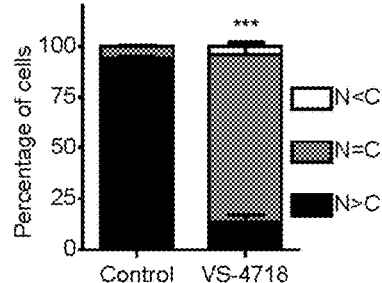

FIGS. 6A-6E

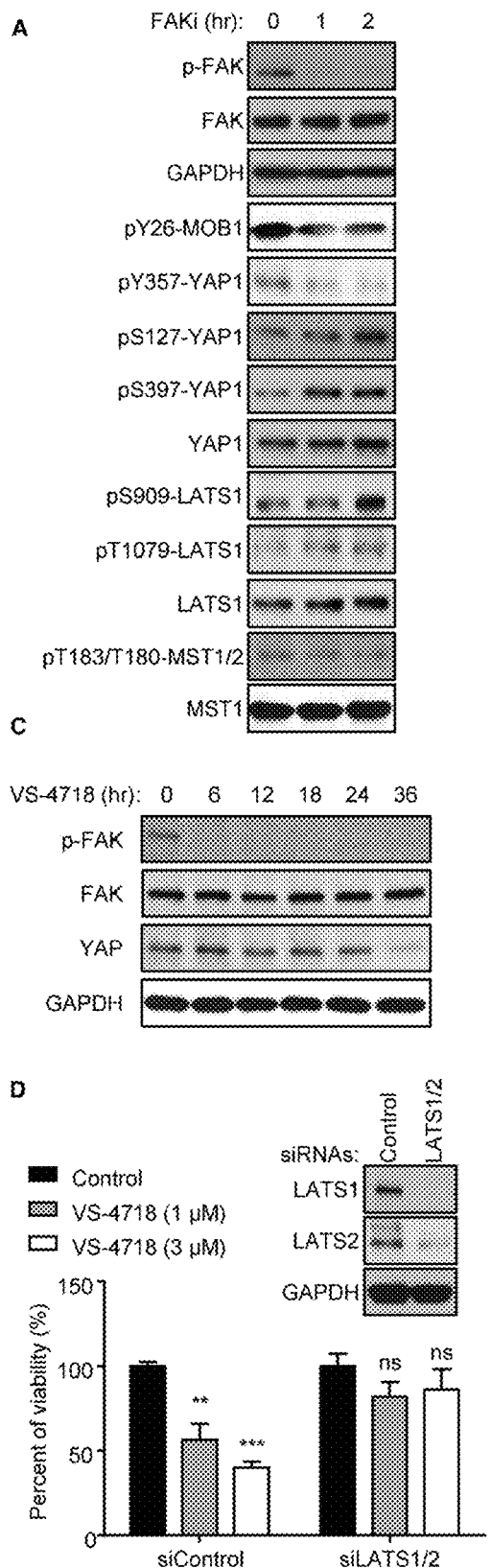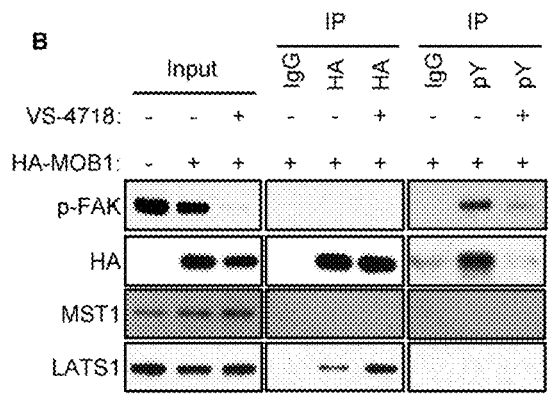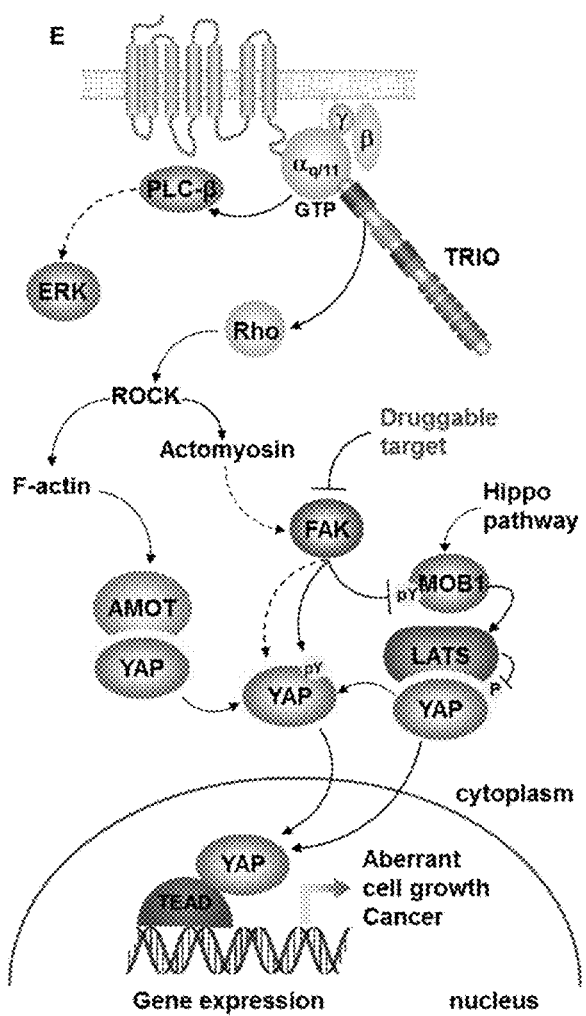
FIGS. 10A-10E

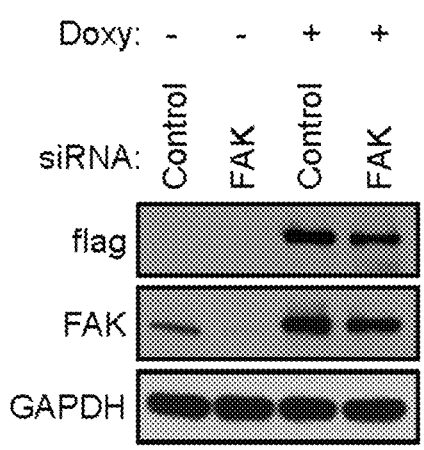
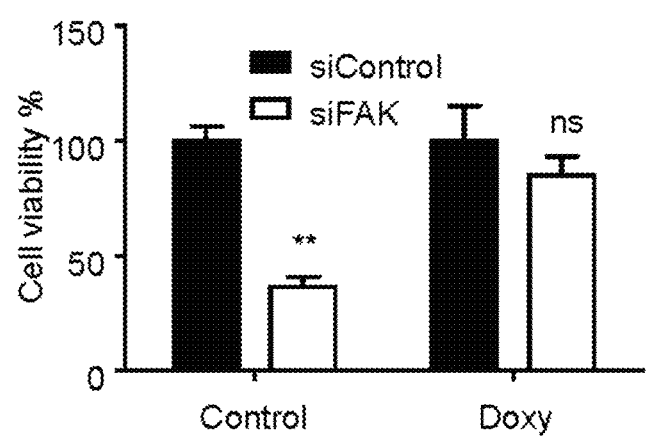
FIG. 13A                    FIG. 13B

SEQUENCE LISTING

<160> NUMBER OF SEQ ID NOS: 14

<210> SEQ ID NO 1
<211> LENGTH: 48
<212> TYPE: PRT
<213> ORGANISM: Homo sapiens

<400> SEQUENCE: 1

Met Ser Phe Leu Phe Ser Ser Arg Ser Ser Lys Thr Phe Lys Pro Lys
1               5                   10                  15

Lys Asn Ile Pro Glu Gly Ser His Gln Tyr Glu Leu Leu Lys His Ala
            20                  25                  30

Glu Ala Thr Leu Gly Ser Gly Asn Leu Arg Gln Ala Val Met Leu Pro
        35                  40                  45

<210> SEQ ID NO 2
<211> LENGTH: 48
<212> TYPE: PRT
<213> ORGANISM: Mus musculus

<400> SEQUENCE: 2

Met Ser Phe Leu Phe Ser Ser Arg Ser Ser Lys Thr Phe Lys Pro Lys
1               5                   10                  15

Lys Asn Ile Pro Glu Gly Ser His Gln Tyr Glu Leu Leu Lys His Ala
            20                  25                  30

Glu Ala Thr Leu Gly Ser Gly Asn Leu Arg Gln Ala Val Met Leu Pro
        35                  40                  45

<210> SEQ ID NO 3
<211> LENGTH: 48
<212> TYPE: PRT
<213> ORGANISM: Rattus norvegicus

<400> SEQUENCE: 3

Met Ser Phe Leu Phe Ser Ser Arg Ser Ser Lys Thr Phe Lys Pro Lys
1               5                   10                  15

Lys Asn Ile Pro Glu Gly Ser His Gln Tyr Glu Leu Leu Lys His Ala
            20                  25                  30

Glu Ala Thr Leu Gly Ser Gly Asn Leu Arg Gln Ala Val Met Leu Pro
        35                  40                  45

<210> SEQ ID NO 4
<211> LENGTH: 48
<212> TYPE: PRT
<213> ORGANISM: Homo sapiens

<400> SEQUENCE: 4

Met Ser Phe Leu Phe Gly Ser Arg Ser Ser Lys Thr Phe Lys Pro Lys
1               5                   10                  15

Lys Asn Ile Pro Glu Gly Ser His Gln Tyr Glu Leu Leu Lys His Ala
            20                  25                  30

Glu Ala Thr Leu Gly Ser Gly Asn Leu Arg Met Ala Val Met Leu Pro
        35                  40                  45

<210> SEQ ID NO 5
<211> LENGTH: 48
<212> TYPE: PRT
<213> ORGANISM: Mus musculus

<400> SEQUENCE: 5

Met Ser Phe Leu Phe Gly Ser Arg Ser Ser Lys Thr Phe Lys Pro Lys

```
1               5                   10                  15
Lys Asn Ile Pro Glu Gly Ser His Gln Tyr Glu Leu Leu Lys His Ala
                20                  25                  30

Glu Ala Thr Leu Gly Ser Gly Asn Leu Arg Met Ala Val Met Leu Pro
            35                  40                  45

<210> SEQ ID NO 6
<211> LENGTH: 48
<212> TYPE: PRT
<213> ORGANISM: Rattus norvegicus

<400> SEQUENCE: 6

Met Ser Phe Leu Phe Gly Ser Arg Ser Ser Lys Thr Phe Lys Pro Lys
1               5                   10                  15

Lys Asn Ile Pro Glu Gly Ser His Gln Tyr Glu Leu Leu Lys His Ala
                20                  25                  30

Glu Ala Thr Leu Gly Ser Gly Asn Leu Arg Met Ala Val Met Leu Pro
            35                  40                  45

<210> SEQ ID NO 7
<211> LENGTH: 47
<212> TYPE: DNA
<213> ORGANISM: Artificial Sequence
<220> FEATURE:
<223> OTHER INFORMATION: Forward primer for Y26F-MOB1

<400> SEQUENCE: 7
catgttttaa gagttcaaac tgatgagatc cttcagggat attcttc            47

<210> SEQ ID NO 8
<211> LENGTH: 47
<212> TYPE: DNA
<213> ORGANISM: Artificial Sequence
<220> FEATURE:
<223> OTHER INFORMATION: Reverse primer for Y26F-MOB1

<400> SEQUENCE: 8
gaagaatatc cctgaaggat ctcatcagtt tgaactctta aaacatg            47

<210> SEQ ID NO 9
<211> LENGTH: 20
<212> TYPE: DNA
<213> ORGANISM: Artificial Sequence
<220> FEATURE:
<223> OTHER INFORMATION: Forward primer for GAPDH

<400> SEQUENCE: 9
gagtcaacgg atttggtcgt                                          20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 10
ttgattttgg agggatctcg                                          20

<210> SEQ ID NO 11
<211> LENGTH: 20
<212> TYPE: DNA
<213> ORGANISM: Artificial Sequence
<220> FEATURE:
```

```
<223> OTHER INFORMATION: Forward primer for CTGF

<400> SEQUENCE: 11
gtttggccca gacccaacta                                                  20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for CTGF

<400> SEQUENCE: 12
ggctctgctt ctctagcctg                                                  20

<210> SEQ ID NO 13
<211> LENGTH: 20
<212> TYPE: DNA
<213> ORGANISM: Artificial Sequence
<220> FEATURE:
<223> OTHER INFORMATION: Forward primer for CYR61

<400> SEQUENCE: 13
caggactgtg aagatgcggt                                                  20

<210> SEQ ID NO 14
<211> LENGTH: 20
<212> TYPE: DNA
<213> ORGANISM: Artificial Sequence
<220> FEATURE:
<223> OTHER INFORMATION: Reverse primer for CYR61

<400> SEQUENCE: 14
gcctgtagaa gggaaacgct                                                  20
```

ANTICANCER TREATMENT FOR UVEAL MELANOMA

CROSS-REFERENCE TO RELATED APPLICATIONS

This application claims priority under 35 U.S.C. § 119(e) to U.S. Provisional Application No. 62/832,425, filed Apr. 11, 2019, the content of which is hereby incorporated by reference in its entirety into this disclosure.

STATEMENT OF GOVERNMENT SUPPORT

This invention was made with government support under the Grant Nos. R33CA225291 and RO1CA102310 awarded by National Cancer Institute. The government has certain rights to the invention.

SEQUENCE LISTING

The instant application contains a Sequence Listing which has been submitted electronically in ASCII format and is hereby incorporated by reference in its entirety. Said ASCII copy, created on Mar. 18, 2020, is named 114198-0902 ST25.txt and is 4,709 bytes in size.

BACKGROUND

The following discussion of the background is merely provided to aid the reader in the understanding the disclosure and is not admitted to describe or constitute prior art to the present disclosure.

Uveal melanoma (UM, also referred to herein as ocular melanoma, OM) is the most common primary cancer of the eye in adults, diagnosed in about 2,500 adults in the US every year. Approximately half of uveal melanoma patients develop liver metastasis within five to ten years after diagnosis independently of successful primary lesion treatment.

Aberrant activity of G proteins and GPCRs have been frequently associated with an oncogenic state and promotion of tumorigenesis (Dorsam and Gutkind, 2007; O'Hayre et al., 2013). However, the precise molecular mechanisms by which prolonged Gαq signaling controls cancer cell growth are still under investigation. Applicant and others have previously shown that these mechanisms are in part due to unique signaling circuitries that lead to the activation of YAP, a transcriptional co-activator regulated by the Hippo pathway. In turn, YAP activation is necessary for UM growth (Feng et al., 2014b; Yu et al., 2014a). As a key downstream target of the tumor suppressive Hippo signaling cascade, YAP is over-activated in multiple cancers (Moroishi et al., 2015; Yu et al., 2015). Despite this, pharmacological targeting of YAP or the Hippo pathway has been challenging. Verteporfin, an ophthalmological drug, inhibits YAP-TEAD interaction, which is the major transcriptional factor regulated by YAP, in UM (Feng et al., 2014b; Yu et al., 2014a) with some anecdotal clinical success (Barbazetto et al., 2003; Soucek and Cihelkova, 2006). However, the potential for verteporfin as a therapeutic has been hindered by its high systemic toxicities after prolonged use (Arnold et al., 2004; Azab et al., 2004).

Currently, no effective therapeutic targets are available for UM, and no specific YAP inhibitors are currently in clinical use (Moroishi et al., 2015). Uveal melanoma (UM) is the most common primary cancer of the eye in adults, and is the second most common melanoma subtype after SKCM (Iorio et al., 2016). It is diagnosed in about 2,500 adults in the United States every year (Julius et al., 2012).

Recent advances in omics technologies have enabled the sequencing and characterization of cancers to an unprecedented depth, revealing previously unknown mechanisms of growth and molecular drivers of disease. Bioinformatics analyses of these data have demonstrated a large heterogeneity in genetic drivers, highlighting complex biological networks towards the identification of therapeutic targets. These large-scale genomics efforts have revealed a small set of cancers that are driven by only a select number of mutational events. One such cancer, uveal melanoma (UM), is characterized by a gain of function mutations in the heterotrimeric G protein, Gαq.

A striking finding from the recent deep sequencing of the UM genomic landscape (TCGA) is that most cases have only a handful of mutations as compared to hundreds in other cancers. Indeed, only 6 genes achieve statistical significance, and typically lack mutations in common cancer drivers, including p53, and RB1, and in melanoma-associated drivers, including BRAF, NRAS, and KIT. Rather, A hotspot mutation in GNAQ or in GNA11 result in encoding constitutively active Gαq proteins rendering them as driver oncogenes in approximately 93% of UM (Van Raamsdonk et al., 2009; Van Raamsdonk et al., 2010). activating mutations in GNAQ and GNA11 (herein referred as GNAQ oncogenes, which encode GTPase deficient and constitutively active Gαq proteins), were identified in ~93% of UM and 4% of SKCM, respectively, where they act as driver oncogenes (Azab et al., 2004). Another ~4% of UM harbor activating mutations in CYSLTR2, a Gαq-linked G protein coupled receptor (GPCR) (Moore et al., 2016) firmly establishing UM as a Gαq-driven malignancy. These findings and our team's early discovery that activated mutants of Gαq represent a new class of oncogenes[4] firmly established UM and a subset of SKCM as Gαq-driven human malignancies. UM tumors harbors genomic alterations in very few tumor suppressor genes, which include mutually exclusive mutations in the SF3B1 (23%) and EIF1AX (13%) splicing factors, and BAP1 (33%), the latter associated with increased risk of metastatic spread (Schrage et al., 2015; Soucek et al., 2006). Approximately 50% of UM patients develop liver metastasis within 5-10 years after diagnosis, independently of the successful treatment of the primary lesions, suggesting that micrometastatic disease precedes treatment of local tumors (Kalinec et al., 1992). Patients with large advanced unresectable tumors and those with primary lesion relapse are at further risk for metastasis (Kalinec et al., 1992). Most metastatic UM (mUM) patients are refractory to current chemotherapies and immune checkpoint blockers, leading to patient death within a year (Kalinec et al., 1992).

Inhibition of the MEK/ERK pathway, a downstream GNAQ target, using the MEK inhibitors (MEKi) selumetinib and trametinib have been extensively evaluated for metastatic or unresectable primary UM treatment; however MEK inhibition with these agents has nearly no impact on the overall survival of mUM patients (Kovacs et al., 2004; Lachowski et al., 2018; and Law et al., 2014). Our team has focused on decoding the oncogenic signaling circuitries downstream of Gαq, which can now provide an opportunity to identify novel druggable targets for UM. In this regard, while the growth promoting activity of Gαq and Gq-GPCRs is already well established (Barretina et al., 2012; Chikumi et al., 2002; and Garnett et al., 2012), the precise mechanisms by which Gαq and its linked receptors transduce sustained proliferative signals is not yet well defined. This is primarily due to the large number of second messenger generating systems and signaling events that can be perturbed upon Gq activation, including PLCβ and PLCε, kinases such as PKC (including classical PKCs and PKCζ, PKD, PKG, CAMKs, MEK5 and most MAPKs, Rho and Ras GTPases, and ARF6, among others (Basu et al., 2013; Chikumi et al., 2002; Cell systems 1, 417-425; Marcotte et al., 2012; and Marcotte et al., 2016) preventing the identification of effective targeted treatment options for mUM.

To date, there are no effective treatment options for (advanced and metastatic UM highlighting an urgent need for novel therapeutic strategies for treating UM.

SUMMARY

This disclosure provides a method for treating uveal melanoma in a subject in need thereof, the method comprising, or consisting essentially of, or yet further consisting of administering an effective amount of an agent that inhibits expression of FAK protein to the subject. In one aspect, the agent that inhibits expression of FAK protein comprises a gene editing agent, or an inhibitor such as VS-4718. In another aspect, the agent is one or more of: VS-4718, GSK2256098, NVP-TAC544, PF 573,228, TAE226, VS-6062, VS-6063, 1H-Pyrrolo(2,3-b)pyridine, Y15, chloropyramine hydrochloride or R2 Y11. In a further aspect, the gene editing agent comprises, or consists essentially of, or yet further consists of RNA interference (RNAi), CRISPR/Cas, ZFN, or TALEN. In one aspect, the gene editing agent is a small interfering RNA (siRNA) targeting transcripts of PTK2. In a further aspect, the siRNA is s11485 available from ThermoFisher Scientific. In yet a further aspect, the siRNA is delivered to a cell of the subject via a vector, including but not limited to, a viral vector, such as a retrovirus, a lentivirus, an adenovirus, an adeno-associated virus (AAV), or a herpes simplex virus (HSV); or a non-viral vector such as a siRNA-lipid complex, a nanoparticle (non-limiting examples of which includes a gold nanoparticle, a lipid nanoparticle and a polymer-based nanoparticle), an antibody conjugate, a chemical carrier, DNA/liposome complex, or micelle (e.g., Lipofectamine (Invitrogen)), or any small molecules that improving oligonucleotide delivery.

Additional melanoma therapies can be combined with the disclosed method, including surgical resection and chemotherapy. The additional therapies alone or in combination thereof can be first line, second line, third line, fourth line or fifth line therapy.

The agents can be administered concurrently or simultaneously. The amounts of each agent can vary with the subject to be treated, the age of the subject and the severity of the disease, which can be determined by the treating veterinarian or physician.

Non-limiting examples of subject to be treated are animals, mammals, simians, rabbits, bovines, ovines, equines, canines, felines and human patients. In one aspect, the subject to be treated is a human. In a further embodiment, the subject is diagnosed with uveal melanoma (UM, including for example, choroidal melanoma, ciliary body melanoma, posterior uveal melanoma, or iris melanoma as well as any local UM, metastatic UM (such as in liver, lung, and bones as well as subcutaneous metastasis), a non-metastatic UM, a primary UM, an advanced UM, a unresectable melanoma or recurrent UM) or suspected of having any UM. Additional anti-melanoma therapies can be added as necessary. In another embodiment, the subject is diagnosed with or suspected of having primary or metastatic skin cutaneous melanoma (SCM) comprising one or more of the following (which is also referred to herein as a constitutively active Gαq): a GNAQ oncogene, a GNA11 oncogene, a CYSLTR2 oncogene, and a constitutively active Gαq. In yet another embodiment, the subject is diagnosed with or suspected of having primary or metastatic cancer comprising one or more of the following (which is also referred to herein as a constitutively active Gαq): a GNAQ oncogene, a GNA11 oncogene, a CYSLTR2 oncogene, and a constitutively active Gαq.

In one aspect of the disclosure, the subject in need of treatment is identified for treatment by testing a sample from the subject for one or more of a deficient GTPase, a constitutively active Gαq protein, an increased expression of Yes-Associated Protein (YAP), a nuclear-localized YAP, an increased phosphorylation of YAP at Y357, a decreased phosphorylation of YAP at S127, a reduced expression of BAP1, or an increased expression of FAK protein. Methods to perform these methods are generally known in the art and some are identified herein.

Administration can vary with the subject and purpose of the therapy, e.g., in one aspect as an animal model to test or treat additional or combination therapies, or as a personalized model to treat a patient. Alternatively, the treatment is for veterinarian use. Non-limiting modes of administration include oral, topical, transdermal, intranasal, vaginal, rectal, subcutaneous intravenous, intraarterial, intramuscular, intraosseous, intraperitoneal, intraocular, subconjunctival, sub-Tenon's, intravitreal, retrobulbar, intracameral, intratumoral, epidural and intrathecal. One or modes of administration can be used simultaneously or concurrently. The amounts and doses can be modified based on the subject being treated.

Also provided is a kit comprising, or consisting essentially of, or yet further consisting of one or more of: agents that inhibit expression of FAK protein, for example, siRNAs, shRNAs, miRNAs, nucleases and guide RNA sequences for carrying out a method as described herein, one or more optional naturally-occurring or non-naturally-occurring carrier(s), and optional instructions for use in a method as disclosed herein.

Further provided is a method for treating uveal melanoma (UM) in a subject in need thereof, the method comprising, or alternatively consisting essentially of, or yet further consisting of, administering an effective amount of a first agent that inhibits focal adhesion kinase (FAK) and a second agent that inhibits mitogen-activated protein kinase (MEK) to the subject. In one aspect, the first agent is one or more of: PF-562271, IN10018, VS-4718, GSK2256098, NVP-TAC544, PF 573,228, TAE226, VS-6062, VS-6063, 1H-Pyrrolo(2,3-b)pyridine, Y15 (1,2,4,5-benzenetetraamine tetrahydrochloride), chloropyramine hydrochloride, R2 Y11, PF-562,271, NVP-226, PND-1186, or GSK2256098. In a second aspect, the second agent is one or more of: selumetinib, trametinib, cobimetinib, CH5126766, Binimetinib, AZD-8330, PD-325901, CI-1040, PD035901 or TAK-733. In one aspect, the first agent is VS-4718 and the second agent is one or more of trametinib, CH5126766, cobimetinib or selumetinib. In a further aspect, the first agent is VS-4718 and the second agent is trametinib. In another aspect, the first agent is VS-6063 and the second agent is trametinib or CH5126766, optionally whereby the combination of VS-6063 and CH5126766 treat a UM synergistically but not any other solid tumor. The agents can be administered concurrently or simultaneously.

In one aspect, the first agent is VS-4718. In another aspect, the first agent is VS-4718 and the second agent is trametinib. In a further aspect the first agent is CH5126766.

In another aspect, the first agent is VS-6063. In another aspect, the first agent is VS-6063 and the second agent is CH5126766. In a further aspect, the first agent is not VS-6063. In another aspect the first agent is not GSK2256098. In a yet further aspect the first agent is neither VS-6063 nor GSK2256098.

Further provided is a composition or therapy comprising, or alternatively consisting essentially of, or yet further consisting of, an effective amount of a first agent that inhibits focal adhesion kinase (FAK) and a second agent that inhibits mitogen-activated protein kinase (MEK). In one embodiment, the activity of a FAK protein refers to its capability of autophosphorylating Tyr397 and/or phosphorylating YAP at Y357 and/or MOB1. In one aspect, the first agent is one or more of: PF-562271, IN10018, VS-4718, GSK2256098, NVP-TAC544, PF 573,228, TAE226, VS-6062, VS-6063, 1H-Pyrrolo(2,3-b)pyridine, Y15 (1,2,4, 5-benzenetetraamine tetrahydrochloride), chloropyramine hydrochloride, R2 Y11, PF-562,271, NVP-226, PND-1186, or GSK2256098. In a second aspect, the second agent is one or more of: selumetinib, trametinib, cobimetinib, CH5126766, Binimetinib, AZD-8330, PD-325901, CI-1040, PD035901 or TAK-733. In one aspect, the first agent is VS-4718 and the second agent is one or more of trametinib, CH5126766, cobimetinib and selumetinib. In a further aspect, the first agent is VS-4718 and the second agent is trametinib. In another aspect, the first agent is VS-6063 and the second agent is trametinib or CH5126766, whereby the combination of VS-6063 and CH5126766 treat a UM synergistically but not any other solid tumor. In one aspect, the first agent is VS-4718. In another aspect, the first agent is VS-4718 and the second agent is trametinib. In a further aspect the first agent is CH5126766. In another aspect, the first agent is VS-6063. In another aspect, the first agent is VS-6063 and the second agent is CH5126766, whereby the combination of VS-6063 and CH5126766 treat a UM synergistically but not any other solid tumor. In a further aspect, the first agent is not VS-6063. In another aspect the first agent is not GSK2256098. In a yet further aspect the first agent is neither VS-6063 nor GSK2256098. In one aspect, the first agent is not IN10018 and the second agent is not cobimetinib. The first and second agents can be combined with a carrier, such as a pharmaceutically acceptable carrier. The amounts in the composition can vary with the subject, the disease progression or the components of the composition.

In one aspect of the disclosure, the subject in need of treatment is identified for treatment by testing a sample (e.g., tumor biopsy) from the subject for one or more of a deficient GTPase, a constitutively active Gαq protein, an increased expression of Yes-Associated Protein (YAP), a nuclear-localized YAP, an increased phosphorylation of YAP at Y357, a decreased phosphorylation of YAP at S127, a reduced expression of BAP1, or an increased expression of FAK protein.

The agents can be administered concurrently or simultaneously. The amounts of each agent can vary with the subject to be treated, the age of the subject and the severity of the disease, which can be determined by the treating veterinarian or physician.

Additional melanoma therapies can be combined with the disclosed method, including surgical resection and chemotherapy. The additional therapies alone or in combination thereof can be first line, second line, third line, fourth line or fifth line therapy.

Non-limiting examples of subject to be treated are animals, mammals, simians, rabbits, bovines, ovines, equines, canines, felines and human patients. In one aspect, the subject to be treated is a human. In a further embodiment, the subject is diagnosed with uveal melanoma (UM, including for example, choroidal melanoma, ciliary body melanoma, posterior uveal melanoma, or iris melanoma as well as any local UM, metastatic UM (such as in liver, lung, and bones as well as subcutaneous metastasis), a non-metastatic UM, a primary UM, an advanced UM, a unresectable melanoma or recurrent UM) or suspected of having any UM. In another embodiment, the subject is diagnosed with or suspected of having primary or metastatic skin cutaneous melanoma (SCM) comprising one or more of the following (which is also referred to herein as a constitutively active Gαq): a GNAQ oncogene, a GNA11 oncogene, a CYSLTR2 oncogene, and a constitutively active Gαq. In yet another embodiment, the subject is diagnosed with or suspected of having primary or metastatic cancer comprising one or more of the following (which is also referred to herein as a constitutively active Gαq): a GNAQ oncogene, a GNA11 oncogene, a CYSLTR2 oncogene, and a constitutively active Gαq.

In one aspect of the disclosure, the subject in need of treatment is identified for treatment by testing a sample from the subject for one or more of a deficient GTPase, a constitutively active Gαq protein, an increased expression of Yes-Associated Protein (YAP), a nuclear-localized YAP, an increased phosphorylation of YAP at Y357, a decreased phosphorylation of YAP at S127, a reduced expression of BAP1, or an increased expression of FAK protein. These methods are generally known in the art, some of which are described herein.

Administration can vary with the subject and purpose of the therapy, e.g., in one aspect as an animal model to test or treat additional or combination therapies, or as a personalized model to treat a patient. Alternatively, the treatment is for veterinarian use. Non-limiting modes of administration include oral, topical, transdermal, intranasal, vaginal, rectal, subcutaneous intravenous, intraarterial, intramuscular, intraosseous, intraperitoneal, intraocular, subconjunctival, sub-Tenon's, intravitreal, retrobulbar, intracameral, intratumoral, epidural and intrathecal. One or modes of administration can be used simultaneously or concurrently.

Also provided is a kit comprising, or consisting essentially of, or yet further consisting of one or more of a first and second agent as identified above, one or more optional naturally-occurring or non-naturally-occurring carrier(s), and optional instructions for use in a method as disclosed herein.

Further provided is a method for selecting a subject having uveal melanoma (UM) or suspected of having uveal melanoma for the therapy as described herein, the method comprising, consisting essentially of, or yet further consisting of, determining if a biological sample isolated from the subject has or is characterized as: a deficient GTPase, a constitutively active Gαq protein, an increased expression of Yes-Associated Protein (YAP), a nuclear-localized YAP, an increased phosphorylation of YAP at Y357, a decreased phosphorylation of YAP at S127, a reduced expression of BAP1, or an increased expression of FAK protein. Methods to perform these methods are known in the art and several are identified herein.

In one aspect, the therapy comprises, or alternatively consists essentially of, or yet further consists of administration of an effective amount of a first agent that inhibits focal adhesion kinase (FAK) in the subject and a second agent that inhibits mitogen-activated protein kinase (MEK) to the subject. In one aspect, the first agent is VS-4718 and the second agent is one or more of trametinib, CH5126766, cobimetinib and selumetinib. In a further aspect, the first agent is VS-4718 and the second agent is trametinib. In another aspect, the first agent is VS-6063 and the second agent is trametinib or CH5126766, whereby the combination of VS-6063 and CH5126766 treat a UM synergistically but not any other solid tumor. In one aspect, the first agent is VS-4718. In another aspect, the first agent is VS-4718 and the second agent is trametinib. In a further aspect the first agent is CH5126766. In another aspect, the first agent is VS-6063. In another aspect, the first agent is VS-6063 and the second agent is CH5126766, whereby the combination of VS-6063 and CH5126766 treat a UM synergistically but not any other solid tumor. In a further aspect, the first agent is not VS-6063. In another aspect the first agent is not GSK2256098. In a yet further aspect the first agent is neither VS-6063 nor GSK2256098. In one aspect, the first agent is not IN10018 and the second agent is not cobimetinib. Additional melanoma therapies can be combined with the disclosed method, including surgical resection and chemotherapy. The additional therapies alone or in combination thereof can be first line, second line, third line, fourth line or fifth line therapy.

Yet further provided is kit for treating uveal melanoma (primary or metastatic) in a subject, the kit comprising, or consisting essentially of, or yet further consisting of, a first agent reduces or inhibits activity or expression of focal adhesion kinase (FAK) protein, a second agent that reduces or inhibits activity or expression of MEK, one or more optional naturally-occurring or non-naturally-occurring carrier(s), and instructions for use. In one aspect, the first agent is VS-4718 and the second agent is one or more of trametinib, CH5126766, cobimetinib and selumetinib. In a further aspect, the first agent is VS-4718 and the second agent is trametinib. In another aspect, the first agent is VS-6063 and the second agent is trametinib or CH5126766, whereby the combination of VS-6063 and CH5126766 treat a UM synergistically but not any other solid tumor. In one aspect, the first agent is VS-4718. In another aspect, the first agent is VS-4718 and the second agent is trametinib. In a further aspect the first agent is CH5126766. In another aspect, the first agent is VS-6063. In another aspect, the first agent is VS-6063 and the second agent is CH5126766, optionally whereby the combination of VS-6063 and CH5126766 treat a UM synergistically but not any other solid tumor. In a further aspect, the first agent is not VS-6063. In another aspect the first agent is not GSK2256098. In a yet further aspect the first agent is neither VS-6063 nor GSK2256098. In one aspect, the first agent is not IN10018 and the second agent is not cobimetinib. Additional melanoma therapies can be combined with the disclosed method, including surgical resection and chemotherapy. The additional therapies alone or in combination thereof can be first line, second line, third line, fourth line or fifth line therapy.

BRIEF DESCRIPTION OF THE DRAWINGS

(FIG. 2A) Pipeline to discover druggable therapeutic targets in UM: molecular screen, survival screen, in vitro screen and druggable screen. (FIG. 2B) Summary of the final 7 gene hits. Molecular, clinical, phenotypic, and synthetic lethal (SL) scores were calculated as in (Lee et al., 2018). Cell viability was assessed in vitro in UM cells (OMM1.3) following siRNA-mediated inhibition of each gene (cell viability normalized to OMM1.3 treated with non-targeting siRNA, siRNA-GNAQ used as positive control, mean, n=3). FIGS. 2C and 2D provide the genomic landscape of OM: FAK (PTK2) is overexpressed in OM. (FIG. 2C) Oncoprint depicting the genomic landscape (genetic alteration) of TCGA UM cohort (Robertson et al., 2017) downloaded from cBioPortal (Gao et al., 2013). Each bar represents one sample and their respective gene mutation or expression status. Percentage of gene alterations (the percentages provided on the right of the bars) and MutSig (the numbers on the right of the percentages for the top 7 genes) or Gistic Q value (the numbers on the right of the percentages for the bottom 2 genes) is listed on the right. (FIG. 2D) Kaplan-Meier plot depicting overall survival for UM patients stratified against PTK2 expression in their tumors. PTK2-High and PTK2-Low groups are defined as top and bottom 50% of PTK2 expression. OM patients with high PTK2 expression (top 50-percentile; lower line) shows poorer survival than the patients with low PTK2 expression (bottom 50-percentile; upper line). (Data from OM TCGA[4], N=80). p value=0.002. (FIG. 2E) UM cell lines (Mel270, 92.1, OMM1.3, OMM1.5 and MEL202 with GNAQ active mutation) cell viability assay after treatment with FAK inhibitor (VS-4718), SKCM cells (SK-MEL-28) served as control. Data are the percent viability normalized to vehicle treatment mean±SEM, n=3). (FIG. 2F) Immunoblot of OMM1.3 cells treated with VS-4718 (decrease in pY397-FAK, left and increased cleaved PARP, 36 hr VS-4718, right). (FIG. 2G) Colony formation assay of OMM1.3 cells with VS-4718 treatment in semisolid media (images of colonies, left and number of colonies, right, mean±SEM, n=3; ***, p<0.001, DMSO treatment as control). See also FIG. 3.

(FIG. 3A) Pan-cancer analysis of FAK alteration frequency. Uveal melanoma exhibits the highest alteration frequency among all tested cancer datasets (76%). Data on genomic alterations (copy number gain and amplification) were downloaded from each indicated TCGA cancer cohort from cBioPortal (Gao et al., 2013). (FIG. 3B) Cell viability assay in UM cell lines (OMM1.3 and Mel270) after treatment with PF562771 (FAK inhibitor), percent viability is normalized to vehicle treatment (mean±SEM, n=3). (FIG. 3C) Mel270 and OMM1.3 cell viability in response to siRNA mediated FAK and Gαq knockdown (mean±SEM, n=3). (FIG. 3D) Immunoblot showing siRNA mediated Gαq knockdown in OMM1.3 cells, and impact on FAK and ERK activation status. (FIG. 3E) Immunoblot showing total and phosphorylated FAK after siRNA mediated FAK knockdown in OMM1.3 cells. (FIG. 3F) Immunoblot showing levels of Gαq and FAK after siRNA mediated FAK and Gαq knockdown in Mel270 cells. (FIG. 3G) Immunoblot showing impact on FAK phosphorylation after a time course of 1 µM VS-4718 treatment (FAK inhibitor) in Mel270 cells.

(FIG. 4A) Immunoblot depicting phosphorylation of FAK after transfection with HA-GαqQL and control expression vectors in HEK293 cells. (FIG. 4B) Immunoblot showing FAK phosphorylation in Gαq-DREADD expressing HEK293 cells stimulated with clozapine N-oxide (CNO) over a time course analysis. (FIG. 4C) Immunoblot depicting FAK and ERK phosphorylation after 2 hr FR900359 (FR) treatment (1 μM) in OMM1.3 cells. FR inhibits Gαq. (FIG. 4D) UM cell viability assay after treatment with FR900359 (FR), SK-MEL-28 BRAF SKCM served as control, percent viability is normalized to vehicle treatment (mean±SEM, n=3). (FIG. 4E) Immunoblot showing phosphorylation of ERK and FAK after stimulation of Gαq-DREADD expressing HEK293 cells with CNO at 5 min in combination with 1 hr U73122 pre-treatment (1 μM). (FIG. 4F) Immunoblot showing phosphorylation of ERK and FAK during a time course of treatment with U73122 (1 μM) in OMM1.3 cells. (FIG. 4G) Immunoblot showing FAK phosphorylation in Gαq-DREADD expressing HEK293 cells after 5 min of CNO stimulation in combination with siRNA mediated TRIO, RhoA or Rac1 knockdown (top), and immunoblot to show efficiency of siRNA mediated TRIO, RhoA or Rac1 knockdown (bottom). (FIG. 4H) Immunoblot showing FAK phosphorylation after siRNA mediated RhoA knockdown in OMM1.3 cells. (FIG. 4I) Immunoblot showing FAK phosphorylation in Gαq-DREADD expressing HEK293 cells after 5 min of CNO stimulation in combination with 1 hr Y-27632 pre-treatment (10 μM) (top), and in combination with 1 hr blebbistatin pre-treatment (20 μM) (bottom). (FIG. 4J) Immunoblot showing FAK phosphorylation during a time course of treatment with Y-27632 (top) and blebbistatin (bottom) in OMM1.3 cells. (FIG. 4K) Cartoon depicting the non-canonical signaling pathway regulating FAK activation by Gαq. G protein βγ subunits are depicted in addition to Gαq. DAG, diacylglycerol; MLC, myosin light chain; see other abbreviations in Example 1.

(FIG. 5A) The top 10 down-regulated oncogenic signatures gene sets from RNA-seq analysis of OMM1.3 cells treated with VS-4718 (1 μM, 2 hr. vehicle treatment as control). FAKi regulates the YAP expression signature in OM. (FIG. 5B) Heatmap depicting the most down-regulated genes by VS-4718 treatment (as A), *=YAP signature genes. The heatmap is shown as grey scale: all controls showed a positive standardized value, while the VS-4718 group was detected with negative standardized values. (FIG. 5C) mRNA expression level of YAP signature genes from RNA-seq data (mean±SEM, n=3). (FIG. 5D) Enrichment plot for YAP Conserved Signature gene set (GSEA, software.broadinstitute.org/gsea/index.jsp). (FIG. 5E) mRNA expression of CTGF and CYR61 measured by qPCR in UM cells OMM1.3 with 2 hr VS-4718 treatment (1 μM, vehicle treatment as control, mean±SEM, n=3). (FIG. 5F) Immunofluorescent staining of endogenous YAP (middle panels) and Hoeschst staining for nuclear DNA (bottom panel) in OMM1.3 cells after 4 hr VS-4718 treatment (1 μM, vehicle treatment as control). (FIG. 5G) Immunoblot showing YAP nuclear and cytoplasmic localization after 2 hr VS-4718 (1 μM) treatment in OMM1.3 cells, using lamin A/C and α-tubulin as nuclear and cytoplasmic markers, respectively. (FIG. 5H) YAP/TAZ Luciferase reporter assay measuring YAP activity after siRNA mediated FAK and Gαq knockdown in OMM1.3 cells (mean±SEM, n=3). (FIG. 5I) Immunoblot showing YAP phosphorylation after siRNA mediated FAK knockdown in OMM1.3 cells. (FIG. 5J) YAP/TAZ Luciferase reporter assay measuring YAP activity after 2 hr treatment with FR900359 (FR), VS-4718 or Dasatinib (1 μM) in OMM1.3 cells (mean±SEM, n=3). (FIG. 5K) Immunoblot showing YAP phosphorylation after 2 hr FR900359 (FR), 709 VS-4718 or Dasatinib (1 μM) treatment in OMM1.3 cells. (In all cases, , p<0.01; *, p<0.001). See also FIGS. 3, 6 and 7.

FIGS. 6A-6E show that FAK inhibition regulates the Hippo-YAP pathway. (FIG. 6A) The top 20 down-regulated oncogenic signatures gene sets from RNA-seq analysis of OMM1.3 cells treated with VS-4718 (1 μM, 2 hr, vehicle treatment as control, with original gene set names). (FIG. 6B) Enrichment plot for IPA YAP1 upregulate gene set. (GSEA, software.broadinstitute.org/gsea/index.jsp). (FIG. 6C) mRNA expression of CTGF and CYR61 measured by qPCR in Mel270 cells after 2 hr, 1 μM VS-4718 treatment (vehicle treatment as control, mean±SEM, n=3). (FIG. 6D) mRNA expression of CTGF and CYR61 measured by qPCR after siRNA mediated knockdown of FAK and Gαq in Mel270 cells (mean±SEM, n=3). (FIG. 6E) Nuclear and cytoplasmic YAP quantification from FIG. 5F, cytoplasm (C) and nucleus (N) (mean±SEM, n=3).

(FIG. 7A) Immunoblot showing phosphorylation of YAP after stimulation of Gαq-DREADD expressing HEK293 cells with 1 μM CNO in combination with 1 μM VS-4718 treatment. (FIG. 7B) mRNA expression of CTGF and CYR61 measured by qPCR (mean±SEM, n=3), and YAP/TAZ Luciferase reporter assay measuring YAP activity (mean±SEM, n=3) with the same treatment in the same cells as FIG. 7A. (FIG. 7C) Immunoblot showing phosphorylation of YAP after transient transfection of GαqQL and control expression vectors in HEK293 cells in combination with 1 μM VS-4718 treatment. (FIG. 7D) Immunoblot showing phosphorylation of YAP after transient transfection of GαqQL and control expression vectors in HEK293 cells in combination with siRNA mediated FAK knockdown. (FIG. 7E) mRNA expression of CTGF and CYR61 measured by qPCR with the same treatment in the same cells as FIG. 7D (mean±SEM, n=3).

(FIG. 8A) Fold-change induction of YAP activity measured by YAP/TAZ Luciferase reporter assay after transient transfection of FAK and control expression vectors in HEK293 cells (mean±SEM, n=3; ***, p<0.001). (FIG. 8B) Immunoblot showing phosphorylation status of YAP after transfection of HA-GαqQL and control expression vectors in HEK293 cells. (FIG. 8C) Immunoblot showing phosphorylation status of YAP after transfection of FAK and control expression vectors in HEK293 cells. (FIG. 8D) Immunoblot against phospho-tyrosine after immunoprecipitation (IP) of tagged Hippo signaling core components (myc-MST1, flag-SAV1, flag-LATS1 or HA-MOB1) transfected with or without FAK in HEK293 cells. Total cell lysates (input) and IP by the indicated antibodies are shown. Western blot for FAK and each of the epitope tags are also shown. (FIG. 8E) Immunoblot showing phosphorylation of MOB1 and association with MST1 and LATS1 after HA or pY immunoprecipitation (IP) in HEK293 cells transfected with or without FAK and wildtype HA-MOB1. (FIG. 8F) Immunoblot showing phosphorylation of MOB1 and association with MST1 and LATS1 after HA or pY immunoprecipitation in HEK293 cells transfected with or without FAK and mutant HA-Y26F-MOB1. See also FIG. 9.

(FIG. 9A) MOB1A and MOB1B phosphorylation sites from PhophoSitePlus (Cell Signaling Technology, www.phosphosite.org, top), and amino acid sequence of MOB1A and MOB1B from human, mouse and rat including tyrosine 26 (Y, pointed by arrowheads) site (bottom). Human MOB1A: SEQ ID NO: 1, mouse MOB1A: SEQ ID NO: 2, rat MOB1A: SEQ ID NO: 3, Human MOB1B: SEQ ID NO: 4, mouse MOB1B: SEQ ID NO: 5, rat MOB1B: SEQ ID NO: 6. (FIG. 9B) Y26 phosphorylation of GST-MOB1 or GST-Y26F-MOB1 (GST used as control) after in vitro kinase reaction using active recombinant human FAK (catalytic domain, FAK-C). (FIG. 9C) Fold-change induction of YAP activity measured by YAP/TAZ Luciferase reporter assay after transient transfection of HA-MOB1 or HA-MOB-Y26F, with or without FAK transfection in HEK293 cells (mean±SEM, n=3; ***, p<0.001, ns: not significant).

FIGS. 10A-10E provide that inhibition of FAK causes YAP inhibition in UM by unleashing Hippo pathway signaling, and inducing inhibitory YAP phosphorylation and degradation. (FIG. 10A) Immunoblot of total and phosphorylated core Hippo pathway members in OMM1.3 cells after VS-4718 treatment (1 μM) for 0, 1 and 2 hours. (FIG. 10B) Immunoblot showing the association of MOB1 with LATS1 after HA or pY immunoprecipitation of OMM1.3 cells transfected with HA-MOB1 with or without 1 hr VS-4718. (FIG. 10C) Immunoblot showing levels of total YAP over a time course of VS-4718 treatment (1 μM) in OMM1.3 cells. (FIG. 10D) Immunoblot showing LATS1/2 knockdown in OMM1.3 cells (top). Cell viability assay in OMM1.3 cells with LATS1/2 knockdown in combination with VS-4718 treatment (bottom, mean±SEM, n=3; , p<0.01, *, p<0.001, ns; not significant). (FIG. 10E) Cartoon depicting the signaling pathway by which FAK mediates YAP activation downstream from constitutively active Gαq mutant in UM. See Example 1 for details. See also FIG. 11.

(FIG. 11A) Immunoblot showing pY397-FAK and pY26-MOB1 with 2 hr treatment of VS-4718 at different doses in OMM1.3 cells (0-10 μM). (FIG. 11B) Immunoblot showing phosphorylation of HA-MOB1 and association with LATS1 after HA immunoprecipitation in OMM1.3 cells with siRNA mediated FAK knockdown. (FIG. 11C) Immunoblot showing phosphorylation of HA-MOB1 or HA-MOB1-Y26F and association with LATS1 after HA immunoprecipitation in OMM1.3 cells with or without VS-4718treatment (1 μM, 2 hr). (FIG. 11D) Immunoblot showing HA-MOB1 and HA-Y26F-MOB1 expression in OMM1.3 (left), HA-Y26F-MOB1 expressing OMM1.3 cells phenocopy the effect of VS-4718 treatment in HA-MOB1 expressing OMM1.3 cells measured by cell viability assay (right, mean±SEM, n=3; ***, p<0.001; ns, not significant). (FIG. 11E) Immunoblot showing YAP phosphorylation after in vitro kinase reaction with active recombinant human FAK (catalytic domain, FAK-C).

(FIG. 12A) Immunoblot showing CRISPR/Cas9-mediated PTK2 knockout in Mel270 cells (wildtype as control). (FIG. 12B) Tumor volume of Mel270 cells in vivo with CRISPR/Cas9-mediated PTK2 knockout (wildtype as control), tumor size at the end of the study were measured (mean±SEM, n=4) (left), and hematoxylin and eosin (H&E)-stained sections of representative tumors from each group are shown (right). (FIG. 12C) Tumor volume of Mel270 cells in vivo with or without VS-4718 treatment, tumor size at the end of the study were measured (mean±SEM, n=8) (left), and hematoxylin and eosin (H&E)-stained sections of representative tumors from each group are shown (right). (FIG. 12D) Ki67 immunohistochemistry staining in Mel270 tumors with or without VS-4718 treatment. (FIG. 12E) Tumor volume of OMM1.3 cells in vivo with or without VS-4718 treatment, tumor size at the end of the study were measured (mean±SEM, n=4) (left), and hematoxylin and eosin (H&E)-stained sections of representative tumors from each group are shown (right). (FIG. 12F) Ki67 immunohistochemistry staining of OMM1.3 tumors with or without VS-4718 treatment. (FIG. 12G) Representative YAP immunohistochemistry staining of Mel270 tumors with or without VS-4718 treatment. (FIG. 12H) Quantification of FIG. 6G, showing fraction of cells with nuclear YAP localization (mean±SEM, n=3). In all cases ***, p<0.001. See also FIG. 13.

FIGS. 13A and 13B provide impacts of siRNA mediated knockdown and doxycycline-induced FAK re-expression. (FIG. 13A) Immunoblot showing siRNA mediated FAK knockdown and doxycycline-induced FAK re-expression in OMM1.3 cells. (FIG. 13B) Impact of siRNA mediated knockdown and doxycycline-induced FAK re-expression in OMM1.3 cells as measured by cell viability assay (mean±SEM, n=3; **, p<0.01; ns, not significant).

(FIG. 14A) Panel of lentiviruses encoding signaling components aberrantly activated in cancer. (FIG. 14B) Maximal inhibition of cell growth determined by FAKi dose-response curves. FAKi-induced cell death is reduced in OM cells (92.1) transduced with PI3K/AKT/mTOR (mTOR S2215Y and PTEN R130Q), ERK-MAPK (BRAF V600E and HRAS G12V) or cell survival (p53 R175H and BCL2) activating mutants. Data are mean±SEM of triplicates.

(FIG. 16A) Left, 92.1 cell viability 72 h after treatment. Percentage of control gradually decreases from the box at let top corner (control) to the bottom right corner. Right, Combination Index values (CI) determined using the Chou-Talalay method. (FIG. 16B) CI at relevant doses (viability=50±5%) using various combinations of FAKi/MEKi. (FIG. 16C) Delta score (ΔBliss), assessing synergism between MEKi (Trametinib, 10 nM) and FAKi (VS-4718, 1 μM) in a panel of OM cells with distinct BAP1 status. 92.1 stable cell lines were generated using the CSTK library (see FIG. 14). See Example 2 for details.

(FIG. 17A) Change in 92.1 xenograft tumor volume in mice treated with vehicle (control), MEKi (trametinib, 1 mg/kg, QD, i.p.), FAKi (VS-4718, 50 mg/kg, BID, p.o.) or both. (FIG. 17B) Quantification of IHC tumor sections stained for BrdU, cleaved-caspase3 (Cl-Casp3), pERK1/2, and YAP. For each panel, the bars from left to right are control, MEKi, FAKi and MEKi+FAKi. Data are mean±SEM (7 mice/group), *p<0.05;p<0.01; *p<0.001; n. s. not significant.

(FIG. 18A) Schematic of the in vivo model of hematogeneous dissemination for OM liver metastasis using 92.1 GFP-Luc cells.

(FIG. 18B) Macroscopic view of liver metastasis (8 weeks post-splenic injection). (FIG. 18C) H&E staining of liver and lung. (FIG. 18D) Fluorescent imaging of the liver showing GFP positive metastasis. (FIG. 18E) Hepatic tumor burden tracked by luciferase imaging in SCID/NOD mice treated with vehicle (control) or MEKi (trametinib, 1 mg/kg, QD, i.p.)+FAKi (VS-4718, 50 mg/kg, BID, p.o.), 6 mice/group. (FIG. 18F) Representative mice of FIG. 18E. (FIG. 18G) Left, Macroscopic and CT imaging of human mOM PDX grown in the liver (arrows indicate tumor). Right, Hepatic tumor burden by in vivo dTomato imaging 7 weeks post splenic injection of PDX cells and 20 days of treatment, 5 mice/group. Data are mean±SEM, ***p<0.001.

DETAILED DESCRIPTION

Definitions

Figure 1:
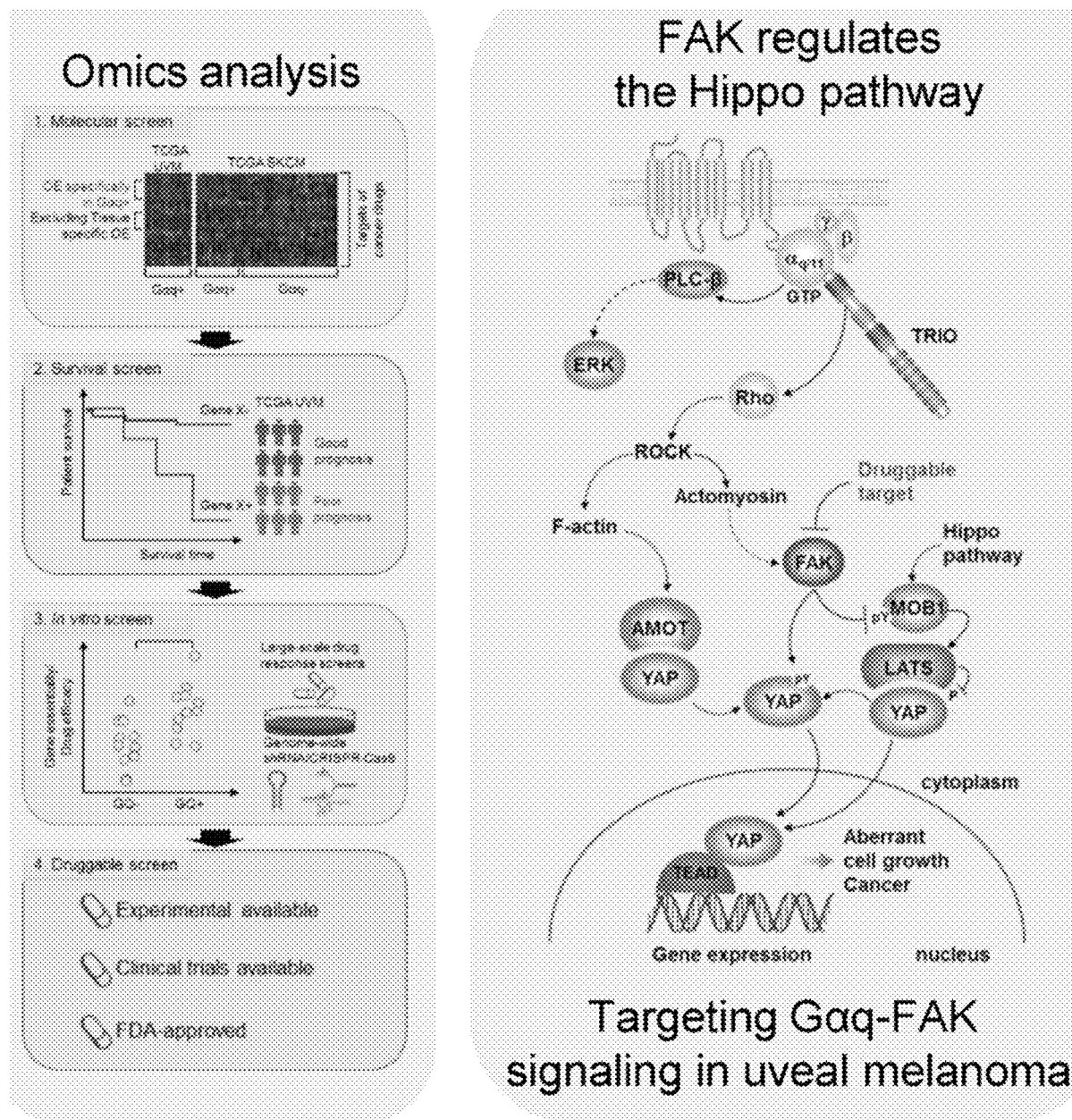
FIG. 1 is a graphical abstract of Example 1. An integrated bioinformatics analysis of predicted synthetic lethality and gene interaction networks reveals FAK as a key mediator of the cancer-promoting signaling circuitry initiated by GNAQ, the uveal melanoma oncogene. Gαq, encoded by GNAQ, activates FAK by a non-canonical signaling pathway, and in turn FAK activates YAP by a novel mechanism suppressing the Hippo kinase cascade. Further in vivo analysis establishes FAK as a viable precision therapeutic target for the treatment of uveal melanoma, a cancer that lacks effective targeted therapies.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

The practice of the present technology will employ, unless otherwise indicated, conventional techniques of tissue culture, immunology, molecular biology, microbiology, cell biology, and recombinant DNA, which are within the skill of the art.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Throughout this disclosure, various publications, patents and published patent specifications are referenced by an identifying citation or by an Arabic numeral. The full citation for the publications identified by an Arabic numeral are found immediately preceding the claims. The disclosures of these publications, patents and published patent specifications are hereby incorporated by reference into the present disclosure in their entirety to more fully describe the state of the art to which this invention pertains.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2nd edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (R. I. Freshney, ed. (1987)).

As used in the specification and claims, the singular form "a", "an", and "the" include plural references unless the context clearly dictates otherwise. For example, the term "a cell" includes a plurality of cells, including mixtures thereof.

As used herein, the term "comprising" is intended to mean that the compositions or methods include the recited steps or elements, but do not exclude others. "Consisting essentially of" shall mean rendering the claims open only for the inclusion of steps or elements, which do not materially affect the basic and novel characteristics of the claimed compositions and methods. "Consisting of" shall mean excluding any element or step not specified in the claim. Embodiments defined by each of these transition terms are within the scope of this disclosure.

As used herein, the term "about" is used to indicate that a value includes the standard deviation of error for the device or method being employed to determine the value. The term "about" when used before a numerical designation, e.g., temperature, time, amount, and concentration, including range, indicates approximations which may vary by (+) or (−) 15%, 10%, 5%, 3%, 2%, or 1%.

As used herein, "and/or" refers to and encompasses any and all possible combinations of one or more of the associated listed items, as well as the lack of combinations when interpreted in the alternative ("or").

As used herein, the term "animal" refers to living multi-cellular vertebrate organisms, a category that includes, for example, mammals and birds. The term "mammal" includes both human and non-human mammals.

The term "subject," "host," "individual," and "patient" are as used interchangeably herein to refer to animals, typically mammalian animals. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs)

and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. A mammal can be a pregnant female. In some embodiments a subject is a human.

In some embodiments, a subject has or is suspected of having a disease such cancer or neoplastic disorder, e.g., as UM. In a further embodiment, the subject is free of skin cutaneous melanoma (SKCM). In some embodiment, a subject is diagnosed with UM or is diagnosed as having a high probability of developing a UM. Such diagnostic methods are disclosed in, for example, Onken et al., Collaborative Ocular Oncology Group report number 1: prospective validation of a multi-gene prognostic assay in uveal melanoma. Ophthalmology 2012; 119: 1596-1603; and Field MG, Harbour J W. Recent developments in prognostic and predictive testing in uveal melanoma. Curr Opin Ophthalmol 2014; 25: 234-239.

In one embodiment, the term "disease" or "disorder" as used herein refers to uveal melanoma (UM), a status of being diagnosed with UM, or a status of being suspect of having UM. In a further embodiment, UM includes (but is not limited to) choroidal melanoma, ciliary body melanoma, posterior uveal melanoma, or iris melanoma. Additionally or alternatively, UM may refer to a local UM, a metastatic UM (such as in liver, lung, and bones as well as subcutaneous metastasis), a non-metastatic UM, a primary UM, an advanced UM, an unresectable melanoma, or a recurrent UM. As used herein, an advanced UM refers to a UM which had progressed after receiving one or more of: the first line therapy, the second line therapy, or the third line therapy. In certain embodiment, the term "disease" or "disorder" as used herein refers to skin cutaneous melanoma (SCM), a status of being diagnosed with SCM, or a status of being suspect of having SCM. In a further embodiment, the SCM comprises a constitutively active Gαq. In certain embodiment, the term "disease" or "disorder" as used herein also refers to any other cancer comprising a constitutively active Gαq.

The term "cell" as used herein may refer to either a prokaryotic or eukaryotic cell, optionally obtained from a subject or a commercially available source.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multistranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

As used herein, the term "isolated cell" generally refers to a cell that is substantially separated from other cells of a tissue. The term includes prokaryotic and eukaryotic cells.

The terms or "acceptable," "effective," or "sufficient" when used to describe the selection of any components, ranges, dose forms, etc. disclosed herein intend that said component, range, dose form, etc. is suitable for the disclosed purpose. An "effective amount" or "efficacious amount" refers to the amount of an agent or combined amounts of two or more agents, that, when administered for the treatment of a mammal or other subject, is sufficient to effect such treatment for the disease. The "effective amount" will vary depending on the agent(s), the disease and its severity and the age, weight, etc., of the subject to be treated.

As used herein, a "cancer" is a disease state characterized by the presence in a subject of cells demonstrating abnormal uncontrolled replication and may be used interchangeably with the term "tumor."

A "solid tumor" is an abnormal mass of tissue that usually does not contain cysts or liquid areas. Solid tumors can be benign or malignant. Different types of solid tumors are named for the type of cells that form them. Examples of solid tumors include sarcomas, carcinomas, and lymphomas.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. Accordingly, a "gene product" as used herein, refers to transcribed mRNA, pre-splicing transcribed RNA (for example, RNA which still comprises non-coding region), translated polypeptide (for example, those with or without signal peptide or other region not present in the mature protein), and protein. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

The term "isolated" as used herein refers to molecules or biologicals or cellular materials being substantially free from other materials. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this technology that is a polynucleotide encompasses both the double-stranded form and each of two complementary single-stranded forms known or predicted to make up the double-stranded form.

As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. When the disease is cancer, the following clinical end points are non-limiting examples of treatment: reduction in tumor burden, slowing of tumor growth, longer overall survival, longer time to tumor progression, inhibition of metastasis or a reduction in metastasis of the tumor. In one aspect, treatment excludes prophylaxis. In some embodiments, treating a UM refers to any one or more of the following: (1) reducing tumor size and/or density of UM; (2) eliminating a UM; (3) slowing down the progression of UM; (4) preventing, inhibiting, reducing or eliminating UM metastasis (for example, hepatic metastasis); and (5) postponing or preventing UM relapse or recurrence.

A "complete response" (CR) to a therapy defines patients with evaluable but non-measurable disease, whose tumor and all evidence of disease had disappeared.

A "partial response" (PR) to a therapy defines patients with anything less than complete response that were simply categorized as demonstrating partial response.

"Stable disease" (SD) indicates that the patient is stable.

"Progressive disease" (PD) indicates that the tumor has grown (i.e. become larger), spread (i.e. metastasized to another tissue or organ) or the overall cancer has gotten worse following treatment. For example, tumor growth of more than 20 percent since the start of treatment typically indicates progressive disease.

"Disease free survival" (DFS) indicates the length of time after treatment of a cancer or tumor during which a patient survives with no signs of the cancer or tumor.

"Non-response" (NR) to a therapy defines patients whose tumor or evidence of disease has remained constant or has progressed.

"Overall Survival" (OS) intends a prolongation in life expectancy as compared to naïve or untreated individuals or patients.

"Progression free survival" (PFS) or "Time to Tumor Progression" (TTP) indicates the length of time during and after treatment that the cancer does not grow. Progression-free survival includes the amount of time patients have experienced a complete response or a partial response, as well as the amount of time patients have experienced stable disease.

"No Correlation" refers to a statistical analysis showing no relationship between the allelic variant of a polymorphic region or gene expression levels and clinical parameters.

"Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer.

"Time to Tumor Recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up.

"Relative Risk" (RR), in statistics and mathematical epidemiology, refers to the risk of an event (or of developing a disease) relative to exposure. Relative risk is a ratio of the probability of the event occurring in the exposed group versus a non-exposed group.

As used herein, the terms "stage I cancer," "stage II cancer," "stage III cancer," and "stage IV" refer to the TNM staging classification for cancer. Stage I cancer typically identifies that the primary tumor is limited to the organ of origin. Stage II intends that the primary tumor has spread into surrounding tissue and lymph nodes immediately draining the area of the tumor. Stage III intends that the primary tumor is large, with fixation to deeper structures. Stage IV intends that the primary tumor is large, with fixation to deeper structures. See pages 20 and 21, CANCER BIOLOGY, $2^{nd}$ Ed., Oxford University Press (1987).

The term "blood" refers to blood which includes all components of blood circulating in a subject including, but not limited to, red blood cells, white blood cells, plasma, clotting factors, small proteins, platelets and/or cryoprecipitate. This is typically the type of blood which is donated when a human patent gives blood.

The term "contacting" means direct or indirect binding or interaction between two or more. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

"Cryoprotectants" are known in the art and include without limitation, e.g., sucrose, trehalose, and glycerol. A cryoprotectant exhibiting low toxicity in biological systems is generally used.

A "composition" typically intends a combination of the active agent, e.g., VS-4718, GSK2256098, NVP-TAC544, PF 573,228, TAE226, VS-4718, VS-6062, VS-6063, 1H-Pyrrolo(2,3-b)pyridine, Y15, chloropyramine hydrochloride and/or R2 Y11 and/or any one or more of the first agent and/or second agent as disclosed herein, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol. Compositions may comprise or alternatively consist essentially of, or yet further consist of a prodrug of the pharmacologically active agent, e.g., VS-4718, GSK2256098, NVP-TAC544, PF 573,228, TAE226, VS-4718, VS-6062, VS-6063, 1H-Pyrrolo(2,3-b)pyridine, Y15, chloropyramine hydrochloride and/or R2 Y11 and/or any one or more of the first agent and/or second agent as disclosed herein. Prodrugs are chemically modified versions of a pharmacologically active agent, which have poor biological activity and must undergo transformation in vivo to release the active drug. Prodrugs are designed to improve the physicochemical, biopharmaceutical and/or pharmacokinetic properties of pharmacologically potent compounds. Functional groups that can be modified for prodrug design are well-known and non-limiting examples of such groups are described in Zawilska et al. (2013) Pharmacol Rep. 65(1):1-14.

The compositions used in accordance with the disclosure, including agents, drugs and pharmaceutical formulations can be packaged in dosage unit form for ease of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described herein.

In one embodiment, the term "siRNA" stands for small interfering RNA which is a non-coding RNA used to interfere with the translation of proteins by binding to and promoting the degradation of messenger RNA (mRNA). In one embodiment, the siRNA is a double strand RNA. The term siRNA also intends short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. Non-limiting examples of a suitable siRNA can be found at thermofisher.com/us/en/home/life-science/rnai/synthetic-rnai-analysis.html, sigmaaldrich.com/life-science/functional-genomics-and-rnai/sirna/mission-predesigned-sirna.html and horizondiscovery.com/en/products/gene-modulation/knockdown-reagents/sirna/sirna, as well as in the Table 1.

The term microRNAs (miRNAs) intends a class of small noncoding RNAs of about 22 nucleotides in length which are involved in the regulation of gene expression at the posttranscriptional level by degrading their target mRNAs and/or inhibiting their translation.

One of skill in the art can monitor expression of genes using methods such as RNA-sequencing, DNA microarrays, Real-time PCR, or Chromatin immunoprecipitation (ChIP) etc. Protein expression can be monitored using methods such as flow cytometry, Western blotting, 2-D gel electrophoresis or immunoassays etc.

One of skill in the art can use methods such as RNA interference (RNAi), CRISPR, TALEN, ZFN or other methods that target specific sequences to reduce or eliminate expression and/or function of proteins. CRISPR, TALEN, ZFN or other genome editing tools can also be used to increase expression and/or function of genes.

As used herein, "RNAi" (RNA interference) refers to the method of reducing or eliminating gene expression in a cell by targeting specific mRNA sequences for degradation via introduction of short pieces of double stranded RNA (dsRNA) and small interfering RNA (such as siRNA, shRNA or miRNA etc.) (Agrawal, N. et al.; Microbiol Mol Biol Rev. 2003; 67:657-685, Arenz, C. et al.; Naturwissenschaften. 2003; 90:345-359, Hannon G J.; Nature. 2002; 418:244-251).

As used herein, the term "CRISPR" refers to a technique of sequence specific genetic manipulation relying on the clustered regularly interspaced short palindromic repeats pathway. CRISPR can be used to perform gene editing and/or gene regulation, as well as to simply target proteins to a specific genomic location. "Gene editing" refers to a type of genetic engineering in which the nucleotide sequence of a target polynucleotide is changed through introduction of deletions, insertions, single stranded or double stranded breaks, or base substitutions to the polynucleotide sequence. In some aspects, CRISPR-mediated gene editing utilizes the pathways of non-homologous end-joining (NHEJ) or homologous recombination to perform the edits. Gene regulation refers to increasing or decreasing the production of specific gene products such as protein or RNA.

The term "gRNA" or "guide RNA" as used herein refers to guide RNA sequences used to target specific polynucleotide sequences for gene editing employing the CRISPR technique. Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRISPR RNA (tracrRNA); or a polynucleotide comprising CRISPR RNA (crRNA) and trans-activating CRISPR RNA (tracrRNA). In some aspects, a gRNA is synthetic (Kelley, M. et al. (2016) J of Biotechnology 233 (2016) 74-83).

The term "Cas9" refers to a CRISPR associated endonuclease referred to by this name. Non-limiting exemplary Cas9s include *Staphylococcus aureus* Cas9, nuclease dead Cas9, and orthologs and biological equivalents each thereof. Orthologs include but are not limited to *Streptococcus pyogenes* Cas9 ("spCas9"), Cas 9 from *Streptococcus thermophiles, Legionella pneumophilia, Neisseria lactamica, Neisseria meningitides, Francisella novicida*; and Cpf1 (which performs cutting functions analogous to Cas9) from various bacterial species including *Acidaminococcus* spp. and *Francisella novicida* U112.

As used herein, "TALEN" (transcription activator-like effector nucleases) refers to engineered nucleases that comprise a non-specific DNA-cleaving nuclease fused to a TALE DNA-binding domain, which can target DNA sequences and be used for genome editing. Boch (2011) Nature Biotech. 29: 135-6; and Boch et al. (2009) Science 326: 1509-12; Moscou et al. (2009) Science 326: 3501. TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence. To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) Nucl. Acids Res. 39: e82; Miller et al. (2011) Nature Biotech. 29: 143-8; Hockemeyer et al. (2011) Nature Biotech. 29: 731-734; Wood et al. (2011) Science 333: 307; Doyon et al. (2010) Nature Methods 8: 74-79; Szczepek et al. (2007) Nature Biotech. 25: 786-793; and Guo et al. (2010) J. Mol. Bio. 200: 96. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) Nature Biotech. 29: 143-8. TALENs specific to sequences in immune cells can be constructed using any method known in the art, including various schemes using modular components. Zhang et al. (2011) Nature Biotech. 29: 149-53; Geibler et al. (2011) PLoS ONE 6: e19509.

As used herein, "ZFN" (Zinc Finger Nuclease) refers to engineered nucleases that comprise a non-specific DNA-cleaving nuclease fused to a zinc finger DNA binding domain, which can target DNA sequences and be used for genome editing. Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) Genetics Society of America 188: 773-782; and Kim et al. (1996) Proc. Natl. Acad. Sci. USA 93: 1156-1160. A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells. Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) Proc. Natl. Acad. Sci. USA 95: 10570-5. ZFNs specific to sequences in immune cells can be constructed using any method known in the art. See, e.g., Provasi (2011) Nature Med. 18: 807-815; Torikai (2013) Blood 122: 1341-1349; Cathomen et al. (2008) Mol. Ther. 16: 1200-7; Guo et al. (2010) J. Mol. Biol. 400: 96; U.S. Patent Publication 201110158957; and U.S. Patent Publication 2012/0060230.

The term "introduce" refers to the process whereby a foreign (i.e. extrinsic or extracellular) agent (for example, a siRNA and/or any other gene editing agent) is introduced into a cell thereby producing a cell comprising the foreign agent. Methods of introducing nucleic acids include but are not limited to transduction, retroviral gene transfer, transfection, electroporation, transformation, viral infection, and other recombinant DNA techniques known in the art. In some embodiments, transduction is done via a vector (e.g., a viral vector or a non-viral vector). Some non-limiting viral vector includes a retrovirus, a lentivirus, an adenovirus, an adeno-associated virus (AAV), or a herpes simplex virus (HSV In some embodiments, transfection is done via a non-viral vector, for example, a siRNA-lipid complex, a nanoparticle (non-limiting examples of which includes a gold nanoparticle, a lipid nanoparticle and a polymer-based nanoparticle), an antibody conjugate, a chemical carrier, DNA/liposome complex, micelle (e.g., Lipofectamine (Invitrogen)) or any small molecules that improving oligonucleotide delivery. In some embodiments, viral infection is done via infecting the cells with a viral particle comprising the polynucleotide of interest (e.g., AAV). In some embodiments, introduction further comprises CRISPR mediated gene editing or Transcription activator-like effector nuclease (TALEN) mediated gene editing. Methods of introducing non-nucleic acid foreign agents (e.g., soluble factors, cytokines, proteins, peptides, enzymes, growth factors, signaling molecules, small molecule inhibitors) include but are not limited to culturing the cells in the presence of the foreign agent, contacting the cells with the agent, contacting the cells with a composition comprising the agent and an excipient, and contacting the cells with vesicles or viral particles comprising the agent.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at cancer.gov, last visited on May 1, 2008. Typically, a patient is given a subsequent chemotherapy regimen because the patient did not show a positive clinical or sub-clinical response to the first line therapy or the first line therapy has stopped.

As used herein, the term "administer" and "administering" are used to mean introducing the therapeutic agent (e.g. polynucleotide, vector, cell, modified cell, population) into a subject. The therapeutic administration of this substance serves to attenuate any symptom, or prevent additional symptoms from arising. When administration is for the purposes of preventing or reducing the likelihood of developing an autoimmune disease or disorder, the substance is provided in advance of any visible or detectable symptom. Routes of administration include, but are not limited to, oral (such as a tablet, capsule or suspension), topical, transdermal, intranasal, vaginal, rectal, subcutaneous intravenous, intraarterial, intramuscular, intraosseous, intraperitoneal, intraocular, subconjunctival, sub-Tenon's, intravitreal, retrobulbar, intracameral, intratumoral, epidural and intrathecal.

As used herein, the term "gene expression profile" refers to measuring the expression level of multiple genes to establish an expression profile for a particular sample.

The term "FAK" is an abbreviation for Focal Adhesion Kinase, which is also known as Protein Tyrosine Kinase 2, PTK2. In certain embodiment, PTK2 is used to refer to the gene or polynucleotide encoding a FAK protein while FAK specifies the encoded protein or polypeptide. More technical features of a human FAK protein can be found at www.uniprot.org/uniprot/Q05397. Seven isoforms are identified, including isoforms 1 to 7 with UniProt Identifiers Q05397-1 to -7, respectively, each of the sequences is incorporated herein in its entirety by reference.

As used herein, the term "inhibit expression of FAK" or "inhibit FAK" or any grammatical variation thereof refers to reducing or eliminating the transcription of the polynucleotide encoding FAK into mRNA, or reducing stability of the transcribed mRNA, or alternatively reducing or eliminating the translation of the mRNA into FAK protein, or reducing or eliminating the functioning of the FAK protein.

The term "increased expression of FAK protein" or any grammatical variation thereof refers to an increased transcription of the polynucleotide encoding FAK into mRNA, or increased stability of the transcribed FAK mRNA, or increased the translation of the mRNA into FAK protein, or increased functioning of the FAK protein. In one embodiment, such increase is compared to a non-cancer cell, a cell which is not a UM cell, a biological sample from a healthy subject, a biological sample from a subject who is free of UM, or a biological sample from a subject who has a melanoma other than UM, for example, a skin cutaneous melanoma (SKCM). In one embodiment, a subject which is suitable for the therapies or methods as disclosed herein has an increased expression of FAK protein. In a further embodiment, a biological sample of the subject has an increased expression of FAK protein.

As used herein, a biological sample, or a sample, is obtained from a subject. Exemplary samples include, but are not limited to, cell sample, tissue sample, tumor biopsy, liquid samples such as blood and other liquid samples of biological origin (including, but not limited to, ocular fluids (aqueous and vitreous humor), peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In some instances, the sample is a tumor biopsy, for example, from a melanoma or a UM.

Such FAK functions include but are not limited to one or more of the following: autophosphorylating tyrosine at position 397 of the FAK (also referred to herein as Y397 or Tyr397, i.e., tyrosine at position 397 of the human FAK isoform 1 or an equivalent position); phosphorylating SRC Proto-Oncogene, Non-Receptor Tyrosine Kinase (SRC); thereby increasing SRC kinase activity; phosphorylating any one or more of Actinin Alpha 1 (ACTN1), Rho Guanine Nucleotide Exchange Factor 7 (ARHGEF7), Growth Factor Receptor Bound Protein 7 (GRB7), Ret Proto-Oncogene (RET) and WASP Like Actin Nucleation Promoting Factor (WASL); promoting phosphorylation of Paxillin (PXN) and Signal Transducer And Activator Of Transcription 1 (STAT1, optionally via a SRC family kinase); promoting phosphorylation of BCAR1 Scaffold Protein, Cas Family Member (BCAR1), GIT ArfGAP 2 (GIT2) and Src Homology 2 Domain Containing (SHC) Adaptor Protein 1 (SHC1); promoting phosphorylation of BMX Non-Receptor Tyrosine Kinase (BMX) and Phosphoinositide-3-Kinase Regulatory Subunit 1 (PIK3R1). Such inhibition may be achieved by a gene editing agent, a small molecular compound, or any molecular (large or small) recognizing and binding to a PTK gene, or a regulatory sequence thereof, or a FAK protein (such as a transcription factor or an antibody). In one embodiment, the activity or function of a FAK protein refers to its capability of autophosphorylating Tyr397 and/or phosporylating YAP at Y357 and/or MOB1.

Methods of evaluating and/or measuring FAK functions are available to one of skill in the art, for example, via kinase activity assays, using a phosphor-specific antibody, western blot, enzyme-linked immunosorbent assay (ELISA), intracellular flow cytometry, immunocytochemistry (ICC), immunohistochemistry (IHC), mass spectrometry, or multianalyte profiling. Also, see, the Examples as well as www.rndsystems.com/resources/articles/methods-detecting-protein-phosphorylation.

In a further embodiment, the agent inhibiting FAK blocks fibronectin-stimulated FAK autophosphorylation of Tyr397, such as VS-4718, which is also known as PND-1186. In another embodiment, the agent inhibiting FAK is any one or more of VS-6063, which is also known as defactinib, BI-4464, PF-562271, IN10018, GSK2256098, NVP-TAC544, PF 573,228, TAE226, VS-6062, 1H-Pyrrolo(2,3-b)pyridine, Y15 (1,2,4,5-benzenetetraamine tetrahydrochloride), chloropyramine hydrochloride, R2 Y11, PF-562,271, or NVP-226.

In one embodiment, the agent is a reversible inhibitor of FAK with IC50 of about 0.1 nM to about 100 nM, about 0.1 nM to about 50 nM, about 0.1 nM to about 20 nM, about 0.1 nM to about 10 nM, about 0.1 nM to about 5 nM, about 0.1 nM to about 2.5 nM, about 0.5 nM to about 100 nM, about 0.5 nM to about 50 nM, about 0.5 nM to about 20 nM, about 0.5 nM to about 10 nM, about 0.5 nM to about 5 nM, about 0.5 nM to about 2.5 nM, about 1 nM to about 100 nM, about 1 nM to about 50 nM, about 1 nM to about 20 nM, about 1 nM to about 10 nM, about 1 nM to about 5 nM, about 1 nM to about 2.5 nM, about 0.4 nM, about 0.8 nM, about 1.5 nM, about 4 nM, about 5 nM, about 5.5 nM, or about 17 nM.

As used herein, a regulatory sequence refers to a segment of a nucleic acid molecule (for example, a DNA) which is capable of control or change the expression of a specific gene (for example, PTK2 or MEK).

As used herein, IC50 is short for half maximal inhibitory concentration, which is a measure of the effectiveness of a substance (such as an agent disclosed herein) in inhibiting a specific biological or biochemical function (for example, of FAK or of MEK). In one embodiment, the IC50 is measured via cell-free assays. In another embodiment, the IC50 is measured via a cellular assay. Examples can be found at, such as, Tomita N et al, Structure-based discovery of cellular-active allosteric inhibitors of FAK. Bioorg Med Chem Lett. 2013 Mar. 15:23(6):1779-85.

The term "MEK" is short for mitogen-activated protein kinases (MAPK) kinase. In certain embodiment, MEK refers to MAPK kinase 1 (MEK1) and/or MAPK kinase 2 (MEK2). The amino acid sequence, structure and other information relating to a *Homo sapiens* (human) MEK1 protein can be found at www.uniprot.org/uniprot/Q02750, which is incorporated herein in its entirety by reference. Two isoforms of MEK1 have been identified: isoform 1 has an amino acid sequence with a UniProt identifier Q02750; while isoform 2 lacks amino acid 147 to amino acid 172 of the isoform 1 and has an amino acid sequence with a UniProt identifier Q02750-2. Each of the sequence is also incorporated herein by reference in its entirety. The amino acid sequence, structure and other information relating to a human MEK2 can be found at the website uniprot.org/uniprot/P36507, which is incorporated herein in its entirety by reference. UniProt identifier P36807 provides an amino acid sequence of a human MEK2.

Inhibiting MEK or any grammatical variation thereof, as used herein, refers to reducing or eliminating the transcription of the polynucleotide encoding MEK into mRNA, or reducing stability of the transcribed mRNA, or reducing or eliminating the translation of the mRNA into MEK protein, or reducing or eliminating the functioning of the MEK protein. Examples of such MEK function are catalyzing the concomitant phosphorylation of a threonine and a tyrosine residue in a Thr-Glu-Tyr sequence located in the extracellular signal-regulated kinases MAPK 3/extracellular signal-regulated kinases (ERK) 1 and MAPK 1/ERK 2, leading to their activation and further transduction of the signal within the MAPK/ERK cascade; activating the ERK 1 and ERK 2; activating B-Raf Proto-Oncogene, Serine/Threonine Kinase (BRAF) in a Kinase Suppressor Of Ras 1 (KSR1) or Kinase Suppressor Of Ras 2 (KSR2)-dependent manner; by binding to KSR1 or KSR2 releasing the inhibitory intramolecular interaction between KSR1 or KSR2 protein kinase and N-terminal domains which promotes KSR1 or KSR2-BRAF dimerization and BRAF activation.

Methods of evaluating and/or measuring an MEK function are available to one of skill in the art, for example, via kinase activity assays, using a phosphor-specific antibody, western blot, enzyme-linked immunosorbent assay (ELISA), intracellular flow cytometry, immunocytochemistry (ICC), immunohistochemistry (IHC), mass spectrometry, or multi-analyte profiling. Also, see, the Examples as well as rndsystems.com/resources/articles/methods-detecting-protein-phosphorylation.

In a further embodiment, the agent inhibiting MEK inhibits RAF-dependent phosphorylation of MEK1 on S217 and thus prevents the dual phosphorylation of MEK (S217 or Ser217, Serine at position 217 of the polypeptide of MEK, i.e., position 218 of MEK1 isoform 1 or an equivalent position; and S221 or Ser 221, Serine at position 221 of the polypeptide of MEK, i.e., position 222 of MEK1 isoform 1 or an equivalent position) required for MEK activation, such as trametinib. In another embodiment, the agent inhibiting MEK inhibits phosphorylation of MEK at S217, S221 or both. In yet another embodiment, the agent inhibiting MEK binds to MEK causing MEK to adopt a conformation in which it cannot be phosphorylated by and released from RAF, such as CH5126766. In certain embodiment, the agent inhibiting MEK is one or more of selumetinib, trametinib, cobimetinib, CH5126766, Binimetinib, AZD-8330, PD-325901, CI-1040, PD035901 or TAK-733.

In one embodiment, the agent is a reversible inhibitor of MEK with IC50 of about 0.1 nM to about 1000 nM, about 0.1 nM to about 500 nM, about 0.1 nM to about 200 nM, about 0.1 nM to about 100 nM, about 0.1 nM to about 50 nM, about 0.1 nM to about 20 nM, about 0.1 nM to about 10 nM, about 0.1 nM to about 5 nM, about 0.1 nM to about 2.5 nM, about 0.1 nM to about 2 nM, about 0.1 nM to about 1 nM, about 0.5 nM to about 1000 nM, about 0.5 nM to about 500 nM, about 0.5 nM to about 200 nM, about 0.5 nM to about 100 nM, about 0.5 nM to about 50 nM, about 0.5 nM to about 20 nM, about 0.5 nM to about 10 nM, about 0.5 nM to about 5 nM, about 0.5 nM to about 2.5 nM, about 0.5 nM to about 2 nM, about 0.5 nM to about 1 nM, about 1 nM to about 1000 nM, about 1 nM to about 500 nM, about 1 nM to about 200 nM, about 1 nM to about 100 nM, about 1 nM to about 50 nM, about 1 nM to about 20 nM, about 1 nM to about 10 nM, about 1 nM to about 5 nM, about 1 nM to about 2.5 nM, about 1 nM to about 2 nM, about 0.3 nM, about 0.33 nM, about 0.92 nM, about 1.8 nM, about 3.2 nM, about 4.2 nM, about 7 nM, about 12 nM, about 14 nM, or about 160 nM.

As used herein, an equivalent position of a sequence in a polypeptide/protein or a polynucleotide can be determined via aligning the sequence with the reference sequence (for example, the amino acid sequence of FAK isoform 1 or MEK1 isoform 1) and the position of the sequence aligned to the reference position in the reference sequence is thereby determined as the equivalent position. Publically or commercially available software or website may be used to perform the sequence alignment, such as www.ebi.ac.uk/Tools/msa/clustalo/, www.ebi.ac.uk/Tools/psa/emboss_needle/, www.ebi.ac.uk/Tools/psa/emboss_stretcher/, www.ebi.ac.uk/Tools/psa/emboss water/, www.ebi.ac.uk/Tools/psa/emboss matcher/, ebi.ac.uk/Tools/psa/lalign/, www.ebi.ac.uk/Tools/psa/genewise/, ncbi.nlm.nih.gov/tools/cobalt/cobalt.cgi?LINK LOC=BlastHomeLink, or blast.ncbi.nlm.nih.gov/Blast.cgi?PAGE_TYPE=BlastSearch&PROG_DEF=blastn&BLAST_PROG_DEF=blastn&BLAST SPEC=GlobalAln&LINK LOC=BlastHomeLink. Default setting may be used when performing the alignment. Alternatively, one of skill in the art may select an appropriate setting.

As used herein, the term GTPase refers to a hydrolase enzyme that binds to the nucleotide guanosine triphosphate (GTP) and hydrolyzes it to guanosine diphosphate (GDP). Accordingly, a deficient GTPase is a GTPase variant or mutant which is not able to hydrolyze a GTP to GDP, or hydrolyzes GTP at a reduced speed, or requires a higher concentration of GTP for hydrolysis. A non-limiting example of measuring the GTPase activity and/or determining a deficient GTPase can be found in the Examples as well as Choudhury S. R., Westfall C. S., Hackenberg D., Pandey S. (2013) Measurement of GTP-Binding and GTPase Activity of Heterotrimeric Gα Proteins. In: Running M. (eds) G Protein-Coupled Receptor Signaling in Plants. Methods in Molecular Biology (Methods and Protocols), vol 1043. Humana Press, Totowa, N.J. In one embodiment, a subject which is suitable for the therapies or methods as disclosed herein has a deficient GTPase. In a further embodiment, a biological sample of the subject has a deficient GTPase. In yet a further embodiment, such deficiency, for example, reduction in hydrolysis activity and/or higher concentration of GTP required, is compared to a non-cancer cell, a cell which is not a UM cell, a biological sample from a healthy subject, a biological sample from a subject who is free of UM, or a biological sample from a subject who has a melanoma other than UM, for example, a skin cutaneous melanoma (SKCM).

The term "YAP" as used herein is short for yes-associated protein, which is also known as transcriptional coactivator YAP. It can an act both as a coactivator and a corepressor and is the critical downstream regulatory target in the Hippo signaling pathway that plays a pivotal role in organ size control and tumor suppression by restricting proliferation and promoting apoptosis. The core of this pathway is composed of a kinase cascade wherein Serine/Threonine Kinase 3 (STK3/MST2) and Serine/Threonine Kinase 4 (STK4/MST1), in complex with its regulatory protein Salvador Family WW Domain Containing Protein 1 (SAV1), phosphorylates and activates Large Tumor Suppressor Kinase 1/2 (LATS1/2) in complex with its regulatory protein Mps One Binder Kinase Activator-Like 1 (MOB1), which in turn phosphorylates and inactivates YAP1 oncoprotein and WW Domain Containing Transcription Regulator 1 (WWTR1/TAZ). Nine YAP1 isoforms are identified. The corresponding amino acid sequences have UniProt Identifiers P46937-1 to -9, each of which is incorporated herein by reference in its entirety. The tyrosine (Tyr or Y) at position 357 of YAP1 isoform 1, or an equivalent position, may be phosphorylated. Phosphorylation sequesters YAP in the cytoplasm by inhibiting its translocation into the nucleus. At low density, YAP is predominantly in the cell nuclear and is translocated to the cytoplasm at high density. See, for example, Hao et al., Tumor suppressor LATS1 is a negative regulator of oncogene YAP. J. Biol. Chem. 283:5496-5509 (2008); and Zhao et al., A coordinated phosphorylation by Lats and CK1 regulates YAP stability through SCF (beta-TRCP). Genes Dev. 24:72-85(2010). In certain embodiment, the terms YAP and YAP1 are used interchangeably.

The term "increased expression of YAP protein" or any grammatical variation thereof refers to an increased transcription of the polynucleotide encoding YAP into mRNA, or increased stability of the transcribed YAP mRNA, or increased the translation of the mRNA into YAP protein, or increased functioning of the YAP protein.

In one embodiment, a subject which is suitable for the therapies or methods as disclosed herein has an increased expression of YAP and/or a nuclear-localized YAP. In a further embodiment, a biological sample of the subject has an increased expression of YAP and/or a nuclear-localized YAP. As tested in the Examples, YAP may be phosphorylated on tyrosine 357 (Tyr 357 or Y357, i.e., Y at position 407 of YAP1 isoform 1 or an equivalent position) and/or serine 127 (Ser 127 or S127, i.e., S at position 127 of YAP1 isoform 1 or an equivalent position). In certain embodiment, a subject which is suitable for the therapies or methods as disclosed herein has an increased phosphorylation at Y357 and a decreased phosphorylation at S127. In a further embodiment, a biological sample of the subject has one of more of the following: an increased expression of YAP, a nuclear-localized YAP, an increased phosphorylation at Y357 and/a decreased phosphorylation at S127. In yet a further embodiment, such difference, such as an increased expression of YAP, a nuclear-localized YAP, an increased phosphorylation at Y357 and a decreased phosphorylation at S127, is compared to a non-cancer cell, a cell which is not a UM cell, a biological sample from a healthy subject, a biological sample from a subject who is free of UM, or a biological sample from a subject who has a melanoma other than UM, for example, a skin cutaneous melanoma (SKCM).

The term "BAP1" is short for BRCA1 Associated Protein 1, which is also known as Ubiquitin carboxyl-terminal hydrolase BAP1. The amino acid sequence, structure and other information relating to a *Homo sapiens* (human) BAP1 protein can be found at uniprot.org/uniprot/Q92560, which is incorporated herein in its entirety by reference. See UniProt Identifier Q92560-1 for an amino acid sequence of the BAP1 protein. In certain embodiment, a subject which is suitable for the therapies or methods as disclosed herein has a reduced expression of BAP1. In a further embodiment, a biological sample of the subject has a reduced expression of BAP1. In yet a further embodiment, such reduced expression of BAP1, is compared to a non-cancer cell, a cell which is not a UM cell, a biological sample from a healthy subject, a biological sample from a subject who is free of UM, or a biological sample from a subject who has a melanoma other than UM, for example, a skin cutaneous melanoma (SKCM).

A reduced expression of BAP1 or any grammatical variation thereof, as used herein, refers to reduced or eliminated transcription of the polynucleotide encoding BAP1 into mRNA, or reduced stability of the BAP1 mRNA, or reduced or eliminated translation of the mRNA into BAP1 protein, or reduced or eliminated functioning of the BAP1 protein.

As used herein, a Gαq protein is a guanine nucleotide-binding protein G(1) subunit alpha, a subunit of one of the heterotrimeric guanine nucleotide binding proteins (G proteins). As disused herein, a GNAQ and/or GNA11 oncogene renders a Gα subunit constitutively activated. See, for example, Van Raamsdonk et al., 2009; Van Raamsdonk et al., 2010. In one embodiment, a subject which is suitable for the therapies or methods as disclosed herein has one or more of the following (which is also referred to herein as a constitutively active Gαq): a GNAQ oncogene, a GNA11 oncogene, a CYSLTR2 oncogene, and a constitutively active Gαq. In a further embodiment, a biological sample of the subject has a constitutively active Gαq. In yet a further embodiment, such constitutively activated Gαq, is compared to a non-cancer cell, a cell which is not a UM cell, a biological sample from a healthy subject, a biological sample from a subject who is free of UM, or a biological sample from a subject who has a melanoma other than UM, for example, a skin cutaneous melanoma (SKCM). In one embodiment, a subject which is suitable for the therapies or methods as disclosed herein has or is diagnosed with or is suspected of having skin cutaneous melanomas (SCM). In a further embodiment, the SCM comprises one or more of the following (which is also referred to herein as a constitutively active Gαq): a GNAQ oncogene, a GNA11 oncogene, a CYSLTR2 oncogene, and a constitutively active Gαq. In one embodiment, a subject which is suitable for the therapies or methods as disclosed herein has or is diagnosed with or is suspected of having another cancer comprising one or more of the following (which is also referred to herein as a constitutively active Gαq): a GNAQ oncogene, a GNA11 oncogene, a CYSLTR2 oncogene, and a constitutively active Gαq.

As used herein, the term "synergistically" or any grammatical variation thereof refers to that two factors (such as inhibiting FAK and inhibiting MEK) taken together achieves an effect greater than the sum of their separate effect under the same condition (i.e., an additive effect).

As used herein, the term "GNAQ" refers to Guanine nucleotide-binding protein G(q) subunit alpha. Its amino acid sequence of homosapiens is available at UniProtKB—P50148 while its transcript and other information is available at www.genecards.org/cgi-bin/carddisp.pl?gene=GNAQ. Activating mutations in GNAQ which encode GTPase deficient and constitutively active Gαq proteins, were identified in ~93% of UM and 4% of SKCM, respectively, where they act as driver oncogenes (Azab et al., 2004). Such mutated GNAQ gene or polynucleotide sequence is referred to herein as a GNAQ oncogene. Non-limiting examples of a GNAQ oncogene includes a gene encoding a GNAQ protein variant having one or both of the following: R183Q or Q209L.

As used herein, the term "GNA11" stands for Guanine nucleotide-binding protein subunit alpha-11. Its amino acid sequence of Homo sapiens is available at UniProtKB—P2992 while its transcript and other information is available at www.genecards.org/cgi-bin/carddisp.pl?gene=GNA11. Activating mutations in GNA11 which encode GTPase deficient and constitutively active Gαq proteins, were identified in ~93% of UM and 4% of SKCM, respectively, where they act as driver oncogenes (Azab et al., 2004). Such mutated GNA11 gene or polynucleotide sequence is referred to herein as a GNA11 oncogene.

As used herein, the term "CYSLTR2" is an abbreviation of Cysteinyl Leukotriene Receptor 2. About 4% of UM harbor activating mutations in CYSLTR2, a Gαq-linked G protein coupled receptor (GPCR) (Moore et al., 2016). Such mutated CYSLTR2 gene or polynucleotide sequence is referred to herein as a CYSLTR2 oncogene.

The terms "equivalent" or "biological equivalent" are used interchangeably when referring to a particular molecule, biological, or cellular material and intend those having minimal homology while still maintaining desired structure or functionality. Non-limiting examples of equivalent polypeptides, include a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, or a polypeptide which is encoded by a polynucleotide or its complement that hybridizes under conditions of high stringency to a polynucleotide encoding such polypeptide sequences. Conditions of high stringency are described herein and incorporated herein by reference. Alternatively, an equivalent thereof is a polypeptide encoded by a polynucleotide or a complement thereto, having at least 70%, or alternatively at least 75%, or alternatively 80%, or alternatively at least 85%, or alternatively at least 90%, or alternatively at least 95% identity, or at least 97% sequence identity to the reference polynucleotide, e.g., the wild-type polynucleotide.

Non-limiting examples of equivalent polypeptides, include a polynucleotide having at least 60%, or alternatively at least 65%, or alternatively at least 70%, or alternatively at least 75%, or alternatively 80%, or alternatively at least 85%, or alternatively at least 90%, or alternatively at least 95%, or alternatively at least 97%, identity to a reference polynucleotide. An equivalent also intends a polynucleotide or its complement that hybridizes under conditions of high stringency to a reference polynucleotide.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity can be determined by incorporating them into clustalW (available at the web address: genome.jp/tools/clustalw/, last accessed on Jan. 13, 2017).

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

MODES OF CARRYING OUT THE DISCLOSURE

Activating mutations in GNAQ and GNA11 (known as GNAQ oncogenes), which encode constitutively active Gαq proteins, occur in ~90% of uveal melanoma (UM) and 4% of skin cutaneous melanoma (SKCM) respectively. UM is the most common primary cancer of the eye in adults, diagnosed in about 2,500 adults in the US every year. Approximately 50% of UM patients develop liver metastasis within 5-10 years after diagnosis, independently of the successful treatment of the primary lesions. There are effective therapeutic strategies for primary UM lesions, but UM metastatic disease is refractory to current chemotherapies and immune checkpoint inhibitors, and most patients with UM metastasis die within a year. The MEK inhibitor selumetinib has been recently approved for UM treatment, but MEK inhibition has nearly no impact on UM patient overall survival. To date, there are no effective treatment options for metastatic UM. Applicants used bioinformatics approaches to identify systems vulnerabilities that can be exploited for UM treatment.

Using the TCGA UM dataset (N=80) and SKCM samples that do not harbor Gαq genomic alterations (N=209) as control, Applicants first identified genes that are highly overexpressed in UM. Applicants validated this approach by confirming that the genes over- and under-expressed in UM and Gαq-altered SKCM are highly overlapping (hypergeometric p<1E-198 and p<1E-232 respectively). Applicants then filtered the genes for those whose inactivation leads to better patient survival in UM based on TCGA survival data. Applicants finally used large datasets of gene essentiality and drug response screens in cancer cells to identify genes that are predicted to reduce cell viability when targeted in Gαq-expressing tumors. By filtering these genes for those that can be targeted by approved and experimental drugs (N=756), Applicants identified 7 candidate druggable genes. Among them, the top was PTK2, which encodes a non-receptor tyrosine kinase known as FAK (focal adhesion kinase). By dissecting the Gαq signaling pathway, Applicants found that Gαq actives FAK (p379-FAK) through a Trio-RhoA signaling pathway, independent of PLC-β regulated second messenger systems. RNA-seq of UM cells treated with a FAK inhibitor (FAKi, VS-4718) revealed that YAP gene-expression signatures were highly sensitive to FAKi. Of interest, YAP is a key regulator of cancer growth, and Applicants have shown that YAP is highly activated by Gαq in UM, contributing to tumor growth (Cancer Cell. 2014). Applicants found FAK regulates YAP activation by Gαq through a mechanism that involves YAP tyrosine phosphorylation on Y357. Interestingly, CRISPR-Cas9 KO of FAK and clinically relevant FAKi showed strong inhibition of UM growth in vitro and in vivo, concomitant with repression of YAP-regulated gene programs. Overall, our computational biology approach revealed that FAK may represent a novel precision therapeutic target human diseases initiated by aberrant Gαq signaling, including UM, the first identified Gαq-driven human malignancy.

Compositions and Methods of Treatment

Provided herein are compositions comprising, or consisting essentially of, or yet further consisting of an agent that inhibits expression of FAK protein in the subject. Further provided herein is a composition comprising, or alternatively consisting essentially of, or yet further consisting of a carrier and one or more of: VS-4718, GSK2256098, NVP-TAC544, PF 573,228, TAE226, VS-4718, VS-6062, VS-6063, 1H-Pyrrolo(2,3-b)pyridine, Y15, chloropyramine hydrochloride and/or R2 Y11, a solvate or prodrug thereof.

In one embodiment, the agent that inhibits expression of FAK protein comprises a gene editing agent, or an inhibitor such as VS-4718. In a further embodiment, the gene editing agent comprises, or consists essentially of, or yet further consists of RNA interference (RNAi), CRISPR/Cas, ZFN, or TALEN. In one aspect, the gene editing agent is a small interfering RNA (siRNA) targeting transcripts of PTK2 or MEK. In a further aspect, the siRNA targeting PTK2 is s11485 available from ThermoFisher Scientific. In yet a further aspect, the siRNA is delivered to a cell of the subject via a vector, including but not limited to, a viral vector, such as a retrovirus, a lentivirus, an adenovirus, an adeno-associated virus (AAV), or a herpes simplex virus (HSV); or a non-viral vector such as a siRNA-lipid complex, a nanoparticle (non-limiting examples of which includes a gold nanoparticle, a lipid nanoparticle and a polymer-based nanoparticle), an antibody conjugate, a chemical carrier, DNA/liposome complex, or micelle (e.g., Lipofectamine (Invitrogen)), or any small molecules that improving oligonucleotide delivery.

Further provided is a composition or therapy comprising, or alternatively consisting essentially of, or yet further consisting of, an effective amount of a first agent that inhibits focal adhesion kinase (FAK) and a second agent that inhibits mitogen-activated protein kinase (MEK).

In one aspect, the first agent is one or more of: PF-562271, IN10018, VS-4718, GSK2256098, NVP-TAC544, PF 573, 228, TAE226, VS-6062, VS-6063, 1H-Pyrrolo(2,3-b)pyridine, Y15 (1,2,4,5-benzenetetraamine tetrahydrochloride), chloropyramine hydrochloride, R2 Y11, PF-562,271, NVP-226, PND-1186, GSK2256098, or a solvate or prodrug thereof. In one embodiment, the first agent that inhibits expression of FAK protein comprises a gene editing agent, or an inhibitor such as VS-4718.

In a second aspect, the second agent is one or more of: selumetinib, trametinib, cobimetinib, CH5126766, Binimetinib, AZD-8330, PD-325901, CI-1040, PD035901, TAK-733, or a solvate or prodrug thereof.

In a further embodiment, the gene editing agent comprises, or consists essentially of, or yet further consists of RNA interference (RNAi), CRISPR/Cas, ZFN, or TALEN. In one aspect, the gene editing agent is a small interfering RNA (siRNA) targeting transcripts of PTK2 or MEK. In a further aspect, the siRNA targeting PTK2 is s11485 available from ThermoFisher Scientific. In yet a further aspect, the siRNA is delivered to a cell of the subject via a vector, including but not limited to, a viral vector, such as a retrovirus, a lentivirus, an adenovirus, an adeno-associated virus (AAV), or a herpes simplex virus (HSV); or a non-viral vector such as a siRNA-lipid complex, a nanoparticle (non-limiting examples of which includes a gold nanoparticle, a lipid nanoparticle and a polymer-based nanoparticle), an antibody conjugate, a chemical carrier, DNA/liposome complex, or micelle (e.g., Lipofectamine (Invitrogen)), or any small molecules that improving oligonucleotide delivery.

In one aspect, the first agent is VS-4718 and the second agent is one or more of trametinib, CH5126766, cobimetinib and selumetinib. In a further aspect, the first agent is VS-4718 and the second agent is trametinib. In another aspect, the first agent is VS-6063 and the second agent is trametinib or CH5126766, whereby the combination of VS-6063 and CH5126766 treat a UM synergistically but not any other solid tumor. In one aspect, the first agent is VS-4718. In another aspect, the first agent is VS-4718 and the second agent is trametinib. In a further aspect the first agent is CH5126766. In another aspect, the first agent is VS-6063. In another aspect, the first agent is VS-6063 and the second agent is CH5126766, whereby the combination of VS-6063 and CH5126766 treat a UM synergistically but not any other solid tumor. In a further aspect, the first agent is not VS-6063. In another aspect the first agent is not GSK2256098. In a yet further aspect the first agent is neither VS-6063 nor GSK2256098. In one aspect, the first agent is not IN10018 and the second agent is not cobimetinib. The first and second agents can be combined with a carrier, such as a pharmaceutically acceptable carrier. The amounts in the composition can vary with the subject, the disease progression or the components of the composition.

The composition of the present disclosure may comprise, or alternatively consist essentially of, or yet further consist of one or more naturally-occurring or non-naturally-occurring carrier, inert or active, such as an adjuvant, diluent, binder, stabilizer, buffers, salts, lipophilic solvents, preservative, adjuvant or the like and include pharmaceutically acceptable carriers. The nature of the carrier can be either soluble or insoluble for purposes of the disclosure. Those skilled in the art will know of other suitable carriers, or will be able to ascertain such, using routine experimentation. Compositions of the present disclosure may comprise or alternatively consist essentially of, or yet further consist of a prodrug of the pharmacologically active agent, e.g., VS-4718, GSK2256098, NVP-TAC544, PF 573,228, TAE226, VS-4718, VS-6062, VS-6063, 1H-Pyrrolo(2,3-b)pyridine, Y15, chloropyramine hydrochloride and/or R2 Y11 and/or any of the agent inhibiting FAK and/or MEK. Prodrugs are chemically modified versions of a pharmacologically active agent, which have poor biological activity and must undergo transformation in vivo to release the active drug. Prodrugs are designed to improve the physico-chemical, biopharmaceutical and/or pharmacokinetic properties of pharmacologically potent compounds. Functional groups that can be modified for prodrug design are well-known and non-limiting examples of such groups are described in Zawilska et al. (2013) Pharmacol Rep. 65(1): 1-14.

This disclosure provides that inhibiting FAK, and optionally inhibiting MEK, in uveal melanoma and the activity of small molecule FAK and/or MEK inhibitors provide potential therapeutic treatment of uveal melanoma tumors with FAK and/or MEK small molecule inhibitors that promote tumor cell death and tumor regression. Further provided is a composition or therapy comprising, or alternatively consisting essentially of, or yet further consisting of, an effective amount of a first agent that inhibits focal adhesion kinase (FAK) and a second agent that inhibits mitogen-activated protein kinase (MEK). Disclosed herein are methods for treating a disease such as uveal melanoma (primary or metastatic) in a subject in need thereof comprising, or alternatively consisting essentially of, or yet further consisting of administering an effective amount of a composition described above to the subject.

Further provided herein are methods for treating a disease such as uveal melanoma (primary or metastatic) in a subject in need thereof comprising, or alternatively consisting essentially of, or yet further consisting of administering an effective amount of an agent that inhibits expression of FAK protein in the subject. In one aspect, the agent that inhibits expression of FAK protein comprises, or alternatively consists essentially of, or yet further consists of a gene editing agent. In one particular aspect, the gene editing agent comprises using one or more of: RNA interference (RNAi), CRISPR/Cas, ZFN, and/or TALEN. In another aspect, the agent is VS-4718, a solvate or prodrug thereof. In a further aspect, the agent is one or more of: VS-4718, GSK2256098, NVP-TAC544, PF 573,228, TAE226, VS-4718, VS-6062, VS-6063, 1H-Pyrrolo(2,3-b)pyridine, Y15, chloropyramine hydrochloride and/or R2 Y11, a solvate or prodrug thereof. Further non-limiting examples of agents that inhibit expression of FAK protein can be found in Sulzmaier et al. (2014) Nat Rev Cancer. 14(9): 598-610.

This disclosure also provides a method for treating a disease such as uveal melanoma (primary or metastatic) in a subject in need thereof, the method comprising, or consisting essentially of, or yet further consisting of administering an effective amount of a first agent that inhibits FAK to the subject. In one embodiment, the method further comprising, or consisting essentially of, or yet further consisting of administering an effective amount of a second agent that inhibits MEK to the subject.

In one aspect, the first agent is one or more of: PF-562271, IN10018, VS-4718, GSK2256098, NVP-TAC544, PF 573, 228, TAE226, VS-6062, VS-6063, 1H-Pyrrolo(2,3-b)pyridine, Y15 (1,2,4,5-benzenetetraamine tetrahydrochloride), chloropyramine hydrochloride, R2 Y11, PF-562,271, NVP-226, PND-1186, or GSK2256098. In a second aspect, the second agent is one or more of: selumetinib, trametinib, cobimetinib, CH5126766, Binimetinib, AZD-8330, PD-325901, CI-1040, PD035901 or TAK-733. In one aspect, the first agent is VS-4718 and the second agent is one or more of trametinib, CH5126766, cobimetinib and selumetinib. In a further aspect, the first agent is VS-4718 and the second agent is trametinib. In another aspect, the first agent is VS-6063 and the second agent is trametinib or CH5126766, whereby the combination of VS-6063 and CH5126766 treat a UM synergistically but not any other solid tumor.

In one aspect, the first agent is VS-4718. In another aspect, the first agent is VS-4718 and the second agent is trametinib. In a further aspect the first agent is CH5126766. In another aspect, the first agent is VS-6063. In another aspect, the first agent is VS-6063 and the second agent is CH5126766, whereby the combination of VS-6063 and CH5126766 treat a UM synergistically but not any other solid tumor. In a further aspect, the first agent is not VS-6063. In another aspect the first agent is not GSK2256098. In a yet further aspect the first agent is neither VS-6063 nor GSK2256098. In one aspect, the first agent is not IN10018 and the second agent is not cobimetinib.

Inhibiting expression of FAK, as well as inhibiting FAK, refers to reducing or eliminating the transcription of the polynucleotide encoding FAK into mRNA, or reducing the stability of a FAK mRNA, or alternatively reducing or eliminating the translation of the mRNA into FAK protein, or reducing or eliminating the functioning of the FAK protein. Expression of FAK can be inhibited by at least about 10% or more, or about 20% or more, or about 30% or more, or about 40% or more, or about 50% or more, or about 60% or more, or about 70% or more, or about 75% or more, or about 80% or more, or about 85% or more, or about 90% or more, or about 91% or more, or about 92% or more, or about 93% or more, or about 94% or more, or about 95% or more, or about 96% or more, or about 97% or more, or about 98% or more or about 99% or more as compared to wild-type expression of FAK protein.

Inhibiting expression of MEK, as well as inhibiting MEK, refers to reducing or eliminating the transcription of the polynucleotide encoding MEK into mRNA, or reducing the stability of a MEK mRNA, or alternatively reducing or eliminating the translation of the mRNA into MEK protein, or reducing or eliminating the functioning of the MEK protein. Expression of MEK can be inhibited by at least about 10% or more, or about 20% or more, or about 30% or more, or about 40% or more, or about 50% or more, or about 60% or more, or about 70% or more, or about 75% or more, or about 80% or more, or about 85% or more, or about 90% or more, or about 91% or more, or about 92% or more, or about 93% or more, or about 94% or more, or about 95% or more, or about 96% or more, or about 97% or more, or about 98% or more or about 99% or more as compared to wild-type expression of MEK protein.

One of skill in the art can monitor expression of the genes using methods such as RNA-sequencing, DNA microarrays, Real-time PCR, or Chromatin immunoprecipitation (ChIP) etc. Protein expression can be monitored using methods such as flow cytometry, Western blotting, 2-D gel electrophoresis or immunoassays etc.

In one aspect, the subject on whom the methods of this disclosure are carried out is a mammal. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. A mammal can be a pregnant female. In some embodiments a subject is a human. In some embodiments, a subject has or is suspected of having Uveal melanoma. Uveal melanoma is an intraocular malignancy that arises from melanocytes of the choroid, ciliary body, and iris of the eye. Yang, J. et al. (2018) Ther Adv Med Oncol., 10. Non-limiting examples of subject to be treated are animals, mammals, simians, rabbits, bovines, ovines, equines, canines, felines and human patients. In one aspect, the subject to be treated is a human. In a further embodiment, the subject is diagnosed with uveal melanoma (UM, including for example, choroidal melanoma, ciliary body melanoma, posterior uveal melanoma, or iris melanoma as well as any local UM, metastatic UM (such as in liver, lung, and bones as well as subcutaneous metastasis), a non-metastatic UM, a primary UM, an advanced UM, a unresectable melanoma or recurrent UM) or suspected of having any UM. In another embodiment, the subject is diagnosed with or suspected of having primary or metastatic skin cutaneous melanoma (SCM) comprising one or more of the following (which is also referred to herein as a constitutively active Gαq): a GNAQ oncogene, a GNA11 oncogene, a CYSLTR2 oncogene, and a constitutively active Gαq. In yet another embodiment, the subject is diagnosed with or suspected of having primary or metastatic cancer comprising one or more of the following (which is also referred to herein as a constitutively active Gαq): a GNAQ oncogene, a GNA11 oncogene, a CYSLTR2 oncogene, and a constitutively active Gαq.

In one aspect of the disclosure, the subject in need of treatment is identified for treatment by testing a sample from the subject for one or more of a deficient GTPase, a constitutively active Gαq protein, an increased expression of Yes-Associated Protein (YAP), a nuclear-localized YAP, an increased phosphorylation of YAP at Y357, a decreased phosphorylation of YAP at S127, a reduced expression of BAP1, or an increased expression of FAK protein. These methods are generally known in the art, some of which are described herein.

Treating uveal melanoma in a subject in need thereof refers to (1) preventing the symptoms of uveal melanoma or uveal melanoma from occurring in a subject that is predisposed or does not yet display symptoms of the disease; (2) inhibiting the disease or arresting its development; or (3) ameliorating or causing regression of uveal melanoma or the symptoms of uveal melanoma. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition caused by uveal melanoma (including uveal melanoma itself), stabilized (i.e., not worsening) state of a condition caused by uveal melanoma (including uveal melanoma itself), delay or slowing of condition caused by uveal melanoma (including uveal melanoma itself), progression, amelioration or palliation of condition caused by uveal melanoma (including uveal melanoma itself), states and remission (whether partial or total), whether detectable or undetectable. When the disease is uveal melanoma, the following clinical end points are non-limiting examples of treatment: reduction in tumor burden, slowing of tumor growth, longer overall survival, longer time to tumor progression, inhibition of metastasis or a reduction in metastasis of the tumor. In one aspect, treatment excludes prophylaxis.

For the above methods, an effective amount is administered, and administration of the cell or population serves to treat the disease, attenuate any symptom or prevent additional symptoms of uveal melanoma from arising. When administration is for the purposes of preventing, delaying or reducing the likelihood of uveal melanoma recurrence or metastasis the compositions can be administered in advance of any visible or detectable symptom. Routes of administration include, but are not limited to, oral (such as a tablet, capsule or suspension), topical, transdermal, intranasal, vaginal, rectal, subcutaneous intravenous, intraarterial, intramuscular, intraosseous, intraperitoneal, intraocular, subconjunctival, sub-Tenon's, intravitreal, retrobulbar, intracameral, intratumoral, epidural and intrathecal. In some embodiments, an effective amount may be delivered or administered into a cavity formed by the resection of tumor tissue (i.e. intracavity delivery) or directly into a tumor prior to resection (i.e. intratumoral delivery). In some embodiments, administration can be intravenously, intrathecally, intraperitoneally, intramuscularly, subcutaneously, or by other suitable means of administration. The quantity and frequency of administration of each agent will be determined by such factors as the condition of the patient, and the type and severity of the patient's uveal melanoma, although appropriate dosages may be determined by clinical trials. Administration can vary with the subject and purpose of the therapy, e.g., in one aspect as an animal model to test or treat additional or combination therapies, or as a personalized model to treat a patient. Alternatively, the treatment is for veterinarian use.

The methods provided herein may be administered either alone or in combination with one or more known anti-cancer therapeutics. They may be administered as a first line therapy, a second line therapy, a third line therapy, or further therapy. Non-limiting examples of additional therapies include surgery, chemotherapy and radiation therapy. Appropriate treatment regimens will be determined by the treating physician or veterinarian.

Further provided is a method for selecting a subject having a disease such as uveal melanoma (UM) or suspected of having a disease such as uveal melanoma for the therapy as described herein, the method comprising, consisting essentially of, or yet further consisting of, determining if a biological sample isolated from the subject has or is characterized as: a deficient GTPase, a constitutively active Gαq protein, an increased expression of Yes-Associated Protein (YAP), a nuclear-localized YAP, an increased phosphorylation of YAP at Y357, a decreased phosphorylation of YAP at S127, a reduced expression of BAP1, or an increased expression of FAK protein. Methods to perform these methods are known in the art and several are identified herein.

In one embodiment, the therapy comprises, or alternatively consists essentially of, or yet further consists of administration of an effective amount of a first agent that inhibits focal adhesion kinase (FAK) in the subject and a second agent that inhibits mitogen-activated protein kinase kinase (MEK) to the subject. In one embodiment, the first agent is VS-4718 and the second agent is one or more of trametinib, CH5126766, cobimetinib and selumetinib. In a further embodiment, the first agent is VS-4718 and the second agent is trametinib. In another embodiment, the first agent is VS-6063 and the second agent is trametinib or CH5126766, whereby the combination of VS-6063 and CH5126766 treat a UM synergistically but not any other solid tumor. In one embodiment, the first agent is VS-4718. In another embodiment, the first agent is VS-4718 and the second agent is trametinib. In a further embodiment the first agent is CH5126766. In another embodiment, the first agent is VS-6063. In another embodiment, the first agent is VS-6063 and the second agent is CH5126766, whereby the combination of VS-6063 and CH5126766 treat a UM synergistically but not any other solid tumor. In a further embodiment, the first agent is not VS-6063. In another embodiment the first agent is not GSK2256098. In a yet further embodiment the first agent is neither VS-6063 nor GSK2256098. In one aspect, the first agent is not IN10018 and the second agent is not cobimetinib. Additional melanoma therapies can be combined with the disclosed method, including surgical resection and chemotherapy. The additional therapies alone or in combination thereof can be first line, second line, third line, fourth line or fifth line therapy.

Kits

Also described herein is are kits comprising, or alternatively consisting essentially of, or yet further consisting of one or more of: compositions of this disclosure, agents that inhibit expression of FAK protein, siRNAs, shRNAs, miRNAs, nucleases and/or guide RNA sequences for carrying out the methods of this disclosure, one or more optional naturally-occurring or non-naturally-occurring carrier(s), and optional instructions for use. In a further aspect, the instruction for use provide directions to conduct any of the methods disclosed herein.

Yet further provided is kit for treating a disease such as uveal melanoma (primary or metastatic) in a subject, the kit comprising, or consisting essentially of, or yet further consisting of, a first agent reduces or inhibits activity or expression of focal adhesion kinase (FAK) protein, a second agent that reduces or inhibits activity or expression of MEK, one or more optional naturally-occurring or non-naturally-occurring carrier(s), and instructions for use.

In one aspect, the first agent is VS-4718 and the second agent is one or more of trametinib, CH5126766, cobimetinib and selumetinib. In a further aspect, the first agent is VS-4718 and the second agent is trametinib. In another aspect, the first agent is VS-6063 and the second agent is trametinib or CH5126766, whereby the combination of VS-6063 and CH5126766 treat a UM synergistically but not any other solid tumor. In one aspect, the first agent is VS-4718. In another aspect, the first agent is VS-4718 and the second agent is trametinib. In a further aspect the first agent is CH5126766. In another aspect, the first agent is VS-6063. In another aspect, the first agent is VS-6063 and the second agent is CH5126766, whereby the combination of VS-6063 and CH5126766 treat a UM synergistically but not any other solid tumor. In a further aspect, the first agent is not VS-6063. In another aspect the first agent is not GSK2256098. In a yet further aspect the first agent is neither VS-6063 nor GSK2256098. Additional melanoma therapies can be combined with the disclosed method, including surgical resection and chemotherapy. The additional therapies alone or in combination thereof can be first line, second line, third line, fourth line or fifth line therapy.

Also provided is a kit comprising, or consisting essentially of, or yet further consisting of one or more of a first and second agent as identified above, one or more optional naturally-occurring or non-naturally-occurring carrier(s), and optional instructions for use in a method as disclosed herein.

The kit components, (e.g., reagents) can be packaged in a suitable container. The kit can also comprise, or alternatively consist essentially of, or yet further consist of, e.g., a carrier such as a buffering agent, a preservative or a protein-stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

As amenable, these suggested kit components may be packaged in a manner customary for use by those of skill in the art. For example, these suggested kit components may be provided in solution or as a liquid dispersion or the like.

The following examples are provided to illustrate and not limit the disclosure.

EXAMPLES

Example 1: A Platform of Synthetic Lethal Gene Interaction Networks Reveals that the GNAQ Uveal Melanoma (UM) Oncogene Controls the Hippo Pathway Through FAK The highly distinctive and well-defined genetic landscape of Uveal Melanoma (UM) provides a unique opportunity for the application of unbiased bioinformatics approaches to investigate the precise molecular mechanisms by which prolonged Gαq signaling controls cancer cell growth, and how these pathways can be targeted for precision therapies of Gαq-driven pathophysiologies. Also, a more complete understanding of Hippo/YAP-regulating mechanisms in cancer could identify urgently needed therapeutic opportunities to inhibit YAP-dependent tumors, including UM.

Here, Applicant applied a recently developed Omics computational framework to predict synthetic lethal gene interactions of Gαq activation (that is, synthetic dosage lethalities of Gαq). These studies revealed that the PTK2 gene, encoding the non-receptor tyrosine kinase known as focal adhesion kinase (FAK), is strictly required for UM cell growth and survival, thereby establishing FAK as a potential viable therapeutic target for the treatment of this aggressive human malignancy.

Activating mutations in GNAQ/GNA11, encoding Gαq G-proteins, are initiating oncogenic events in uveal melanoma (UM). Using an integrated bioinformatics pipeline, Applicant found that PTK2, encoding Focal Adhesion Kinase (FAK), represents a candidate synthetic lethal gene with GNAQ activation. Applicant show that Gαq activates FAK through TRIO-RhoA non-canonical Gαq-signaling, and genetic ablation or pharmacological inhibition of FAK inhibits UM growth. Analysis of the FAK-regulated transcriptome demonstrated that GNAQ stimulates YAP through FAK. Dissection of the underlying mechanism revealed that FAK regulates YAP by tyrosine phosphorylation of MOB1, inhibiting core Hippo signaling. Applicant's findings establish FAK as a potential therapeutic target for UM and other Gαq-driven pathophysiologies that involve unrestrained YAP function.

Despite the central role of Hippo/YAP-regulating mechanisms in uveal melanoma (UM), there are no clinically effective therapeutic targets. Dissection of mediators regulating Hippo/YAP-signaling could identify urgently needed therapeutic opportunities to inhibit YAP-dependent tumor growth in UM and other cancers. Coupling the power of an unbiased computational pipeline to the unique genetic landscape of UM, Applicant uncovered a molecular framework regulating YAP and identified FAK as a druggable signaling hub downstream from GNAQ in UM. Gαq activates tyrosine phosphorylation networks through FAK, which activates YAP by a direct mechanism suppressing the Hippo kinase cascade. FAK inhibitors suppress YAP activation in vivo and halt UM growth, exposing a signaling vulnerability that can be targeted for UM treatment.

A Recently Described Bioinformatics Pipeline Identifies PTK2 as a Druggable Candidate Synthetic Lethal Gene with GNAQ.

To identify the specific vulnerabilities of GNAQ-driven tumors, Applicant adapted our recently established bioinformatics pipeline that identifies clinically relevant Synthetic Lethal Interactions (termed ISLE, (Lee et al., (2018) Harnessing synthetic lethality to predict the response to cancer treatment. Nat. Commun 9:2546)). Applicant denote a sample with mutations or gene amplification of GNAQ, GNA11 and CYSLTR2 as Gαq+, while a sample without any of these genetic alterations as Gαq−. Adapting the rationale of the ISLE pipeline to our aim here, a candidate gene was determined to be a synthetic lethal (and thus a druggable vulnerability) of Gαq+ tumors if it satisfies the following four conditions (FIG. 2A): (i) molecular condition: Gαq+ tumor should differentially overexpress the candidate gene vs Gαq− samples, (ii) clinical condition: Overexpression of the candidate gene should be associated poor survival in Gαq+ tumors, (iii) phenotypic condition: The candidate gene is significantly more essential in Gαq+ than in Gαq− cell lines, (iv) druggable condition: Targeting the candidate gene products with inhibitors is significantly more effective in Gαq+ than in Gαq− cell lines.

Figures 2A, 2B, 2C, 2D, 2E, 2F, 2G:
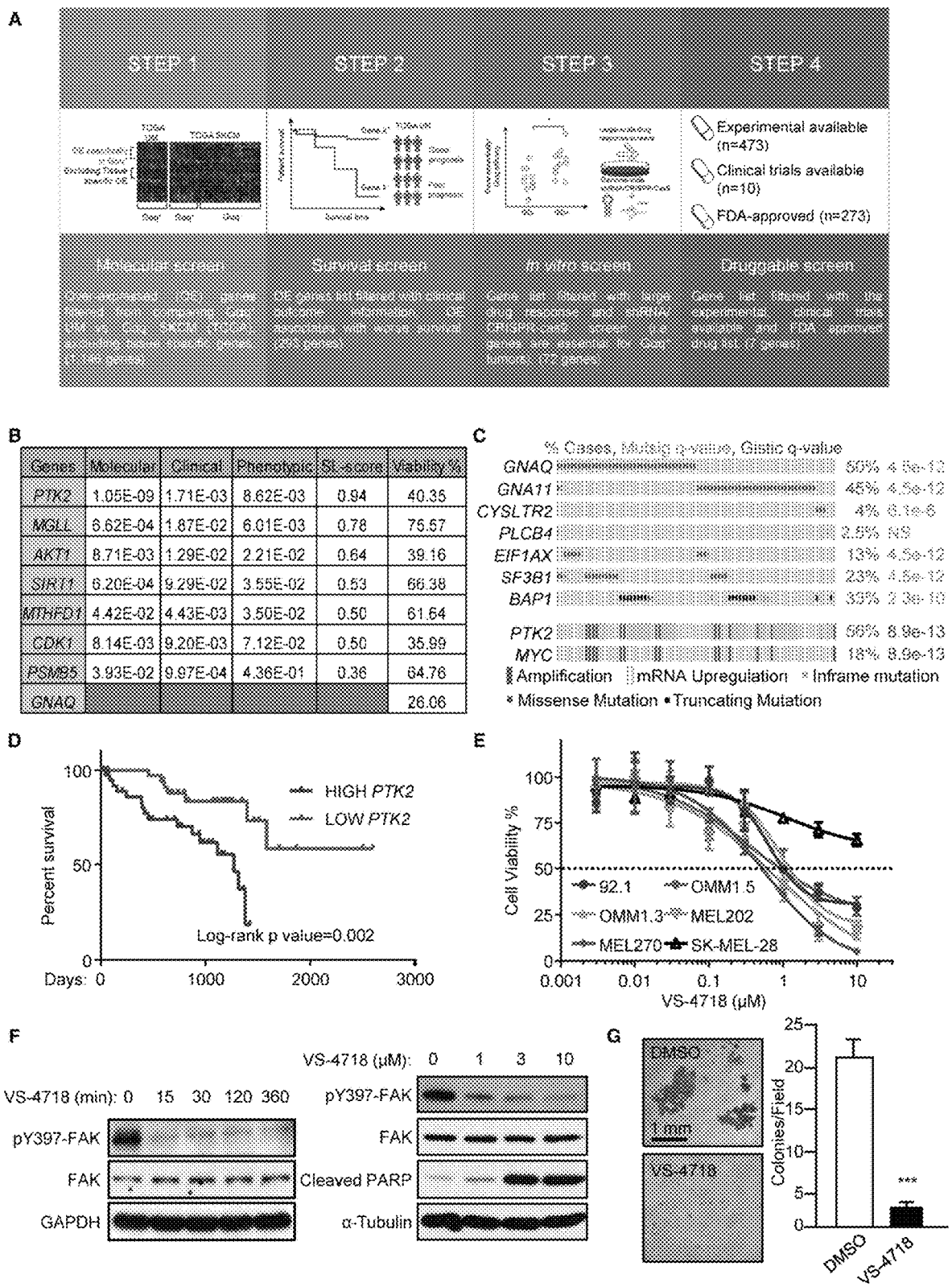
FIGS. 2A-2G show that bioinformatics analysis reveals FAK as critical for UM progression.

Applicants' analysis therefore proceeded along four steps. First, taking advantage of the publicly available Cancer Genome Atlas (TCGA) (Cancer Genome Atlas Research et al., 2013) data, Applicant extracted genes that are differentially overexpressed in Gαq+UM (>96%). Since there are not sufficient UM Gαq− samples, Applicant used Gαq− skin cutaneous melanoma (SKCM) samples as a control. Indeed, Applicant observed significant overlap in the overexpressed genes in Gαq+UM and Gαq+ SKCM samples (hypergeometric p<4.83 e-199, see Methods) compared to Gαq− SKCM samples, justifying the use of Gαq− SKCM samples as a control for Gαq+UM. Applicant excluded genes overexpressed in UM compared to SKCM irrespective of Gαq status to control for cancer type-specific differential expression. Second, among the genes that pass the first filter, Applicant identified those whose expression correlates with poor prognosis of UM patients. Third, Applicant further selected those genes from in vitro functional screens that show significantly higher essentiality (or drug response) in Gαq+ cancer cell lines following the standard procedure to determine cancer cell dependency (Tsherniak et al., 2017). Lastly, Applicant selected only those genes that are druggable, i.e. targets of known cancer drugs (FIG. 2A). Applicant performed cell viability assays after siRNA mediated gene inhibition, confirming the vulnerabilities of our predicted hits in Gαq+ cells (FIG. 2B). This four step Gαq+ synthetic lethal (SL) identification process results in 7 predicted SL genes, which play roles in multiple biological processes, including cell growth, cell survival, lipid metabolism regulation, cell cycle control and the processing of class I MHC peptide, all of which reduced cell growth when knocked down. Among them, the top predicted gene, PTK2, encoding Focal Adhesion Kinase (FAK), reduced cell viability almost 60% after inhibition using PTK2 specific siRNA knockdown (FIG. 2B).

Figures 3A, 3B, 3C, 3D, 3E, 3F, 3G:
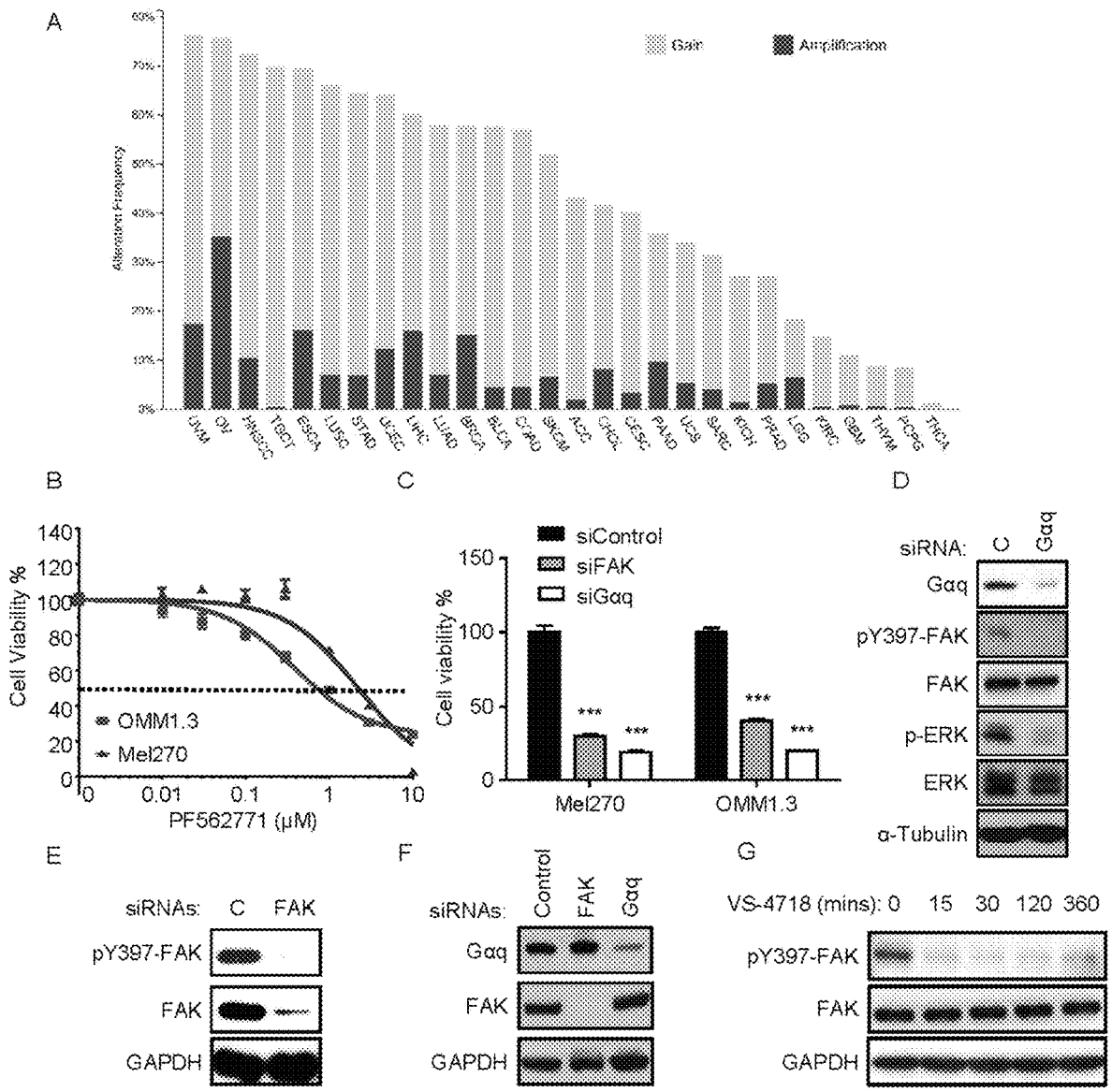
FIGS. 3A-3G provide further analysis relating to FAK.

PTK2 is not mutated in UM, a disease that is characterized by mutations, primarily mutually exclusive activating mutations in GNAQ, GNA11 and CYSLTR2, and mutually exclusive mutations in genes encoding two RNA splicing factors, EIF1AX and SF3B1, or a deubiquitinase BAP1, as depicted in (FIG. 2C) (Moore et al., 2016; Robertson et al., 2017; Van Raamsdonk et al., 2009; Van Raamsdonk et al., 2010). Instead, statistically significant gain of chromosome 8q (Robertson et al., 2017), including PTK2 and MYC, occurs in UM. Interestingly, PTK2 and MYC are amplified in 18% of UM cases (TCGA), and 38% of UM cases also exhibit PTK2 mRNA upregulation independent of amplification (FIG. 2C). In total 56% of UM cases have PTK2 gene amplification or mRNA upregulation (FIG. 2B). Interestingly, Applicant found that expression of PTK2 is significantly correlated with reduced overall patient survival (FIG. 2D). Strikingly, a pan-cancer analysis of alteration frequency of PTK2 reveals that UM has the highest alteration frequency among all available TCGA solid tumor cohorts (FIG. 3A). Applicant next tested the sensitivity of five representative UM cell lines, 92.1, OMM1.3, OMM1.5, Mel270, and Mel202, all of which harbor GNAQ mutations, to FAK inhibition using VS-4718, an orally-bioavailable FAK inhibitor (FAKi) (Sulzmaier et al., 2014), using the SKCM cell line SK-MEK-28 (BRAF 151 mutant) as a control. In vitro, UM cell lines demonstrate a dose-dependent sensitivity to FAK inhibition with an EC50 of around 1 μM (FIG. 2E). Similar results were obtained with PF562771, a chemically distinct FAKi (FIG. 3B). Instead, the SK-MEK-28 cell line was largely insensitive to FAKi, with an EC50>10 µM for VS-4718 (FIG. 2E). siRNA knockdown of FAK reduced cell viability in two representative UM cells nearly as potently as Gαq (encoded by GNAQ) knock down (FIGS. 3C, 3D, 3E and 3F). Gαq knock down reduced the accumulation of FAK in its active, tyrosine 397 phosphorylated form (pY397-FAK) (Sulzmaier et al., 2014) (FIG. 3D), while FAK knock down reduced total FAK and pY397-FAK protein levels, as expected (FIG. 3E). FAKi inhibited FAK rapidly (FIGS. 3F and 3G), and resulted in UM apoptosis as judged by the accumulation of cleaved PARP (FIG. 2F). Applicant further assessed whether inhibition of FAK impacted the oncogenic potential of UM cells by measuring their clonogenic capacity in semisolid media and found that FAKi nearly abolished the colony formation ability of UM cells (FIG. 2G). Together, these findings support that FAK may be required for GNAQ-driven UM cell proliferation, survival, and clonogenic growth, thereby representing a potential therapeutic target for the treatment of UM.

The Canonical Gαq Signaling Pathway is Dispensable but a TRIO-RhoA Non-Canonical Signaling Mechanism is Evident for FAK Activation.

Figures 4A, 4B, 4C, 4D, 4E, 4F, 4G, 4H, 4I, 4J, 4K:
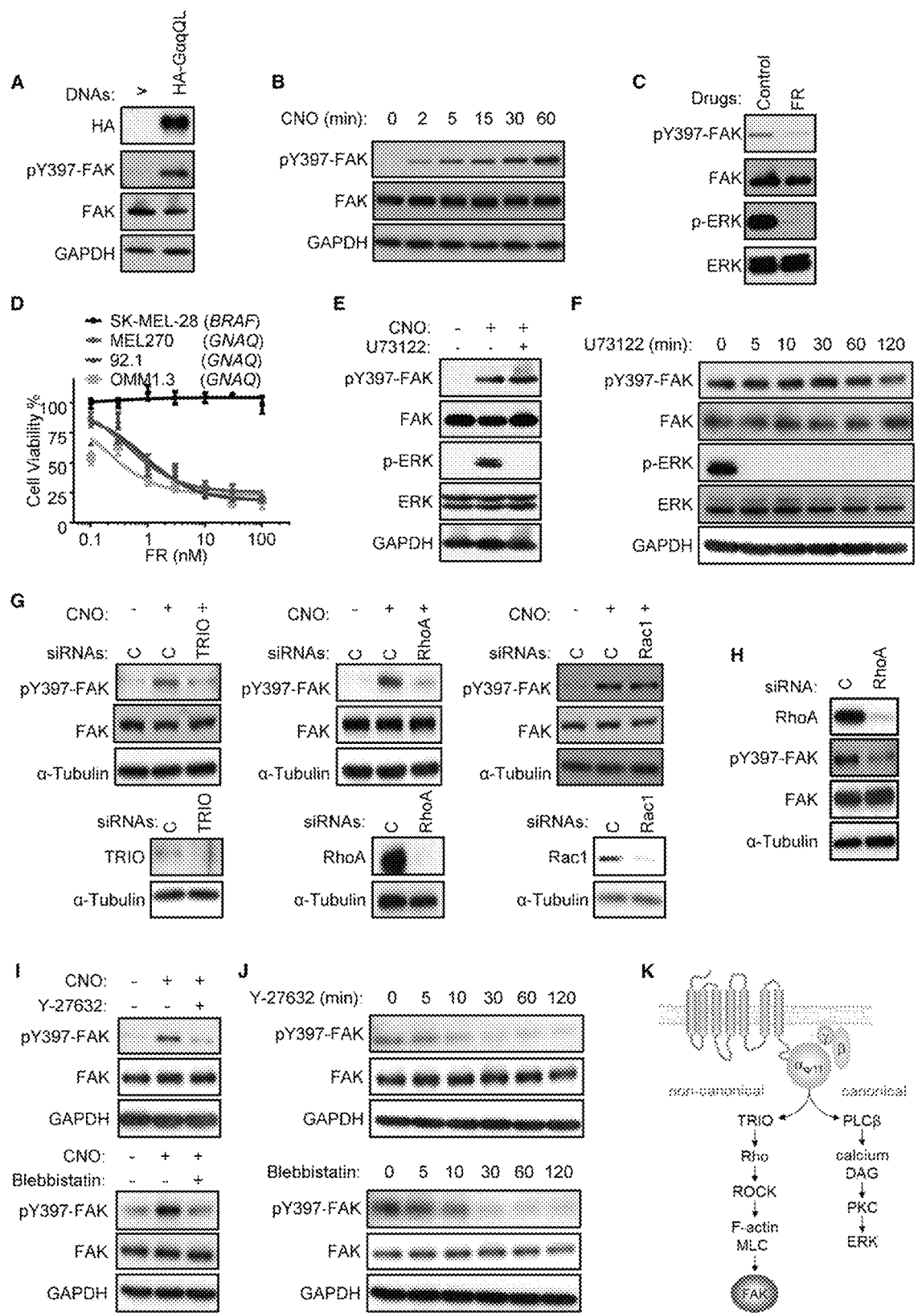
FIGS. 4A-4K show that Gαq regulates FAK activation through a non-canonical TRIO/RhoA-mediated signaling circuitry.

Applicant next sought to investigate the mechanism by which Gαq controls FAK. To understand the impact of GNAQ mutation on FAK activation, Applicant express an HA-tagged activated Gαq mutant, Gαq-Q209L (HA-GαqQL), observed in UM and an empty vector control in human embryonic kidney 293 (HEK293) cells. Immunoblotting against total and phosphorylated forms of FAK revealed that phosphorylation of FAK at Y397 was significantly increased after expression of GαqQL (FIG. 4A). Applicant next took advantage of a previously established synthetic Gαq-coupled GPCR (Gαq-DREADD) that can be activated by a synthetic ligand, Clozapine N-oxide (CNO) (Armbruster et al., 2007; Vaque et al., 2013). Applicant stimulated Gαq-DREADD expressing HEK293 cells with CNO over a time course and found increasingly elevated levels of pY397 FAK in response to CNO (FIG. 4B). In UM cells, Gαq knockdown by siRNA or inhibition by FR900359 (FR), a potent Gαq inhibitor (Schrage et al., 2015), diminished FAK and ERK activation (FIGS. 4C and 3D). Consistent with these data, Gαq inhibition with FR in UM cells and SKCM cells showed inhibition of cell proliferation only in UM cells (FIG. 4D). These results support the notion that FAK acts downstream from the Gαq in UM. However, it is unclear which of the multiple Gαq or Gαq coupled receptor-initiated signaling pathways are responsible for regulating FAK activation.

PLCβ-dependent second messenger activation is among the best-known downstream events stimulated by Gαq (Griner and Kazanietz, 2007; Hubbard and Hepler, 2006), and is considered to be the canonical Gαq signaling pathway, causing transient ERK activation (Vague et al., 2013). Inhibition of PLCβ by the use of a small-molecule PLC inhibitor abolished the ERK activation, as Applicant previously reported (Vague et al., 2013), but did not have an impact on the activation of FAK (FIG. 4E). Similarly, inhibition of PKC blocked ERK activation but not FAK in UM cells (FIG. 4F), indicating that FAK may be activated independently of PLCβ. As Gαq activation of the AP1 and YAP transcriptional programs involves the stimulation of the TRIO guanine nucleotide exchange factor (GEF) for Rho GTPases (Feng et al., 2014b; Vague et al., 2013), Applicant next asked if this non-canonical Gαq signaling pathway is involved in FAK activation by Gαq. Knockdown of TRIO or RhoA prevented the activation of FAK by Gαq-DREADD in HEK293 cells and Gαq in UM cells (FIGS. 4G and 4H). In line with these findings, knockdown of Rac1 had no impact on FAK activation (FIG. 4G). Further analysis showed that blocking actin polymerization by inhibiting ROCK or actomyosin contraction by Y-27632 (Ikeda et al., 2003; Narumiya et al., 2000) and blebbistatin (Kovacs et al., 2004), respectively, repressed FAK activation by Gαq-DREADD in HEK293 cells and Gαq in UM cells (FIGS. 4I and 4J). Together, these findings suggest that Gαq stimulates FAK independently of PLCβ and PKC, but instead through a non-canonical TRIO-dependent pathway resulting in RhoA activation and consequent cytoskeletal changes and actomyosin-initiated cell contraction and signaling (FIG. 4K).

FAK Inhibition Represses the Transcriptional Activity of YAP.

Figures 5A, 5B, 5C, 5D, 5E, 5F, 5G, 5H, 5I, 5J, 5K:
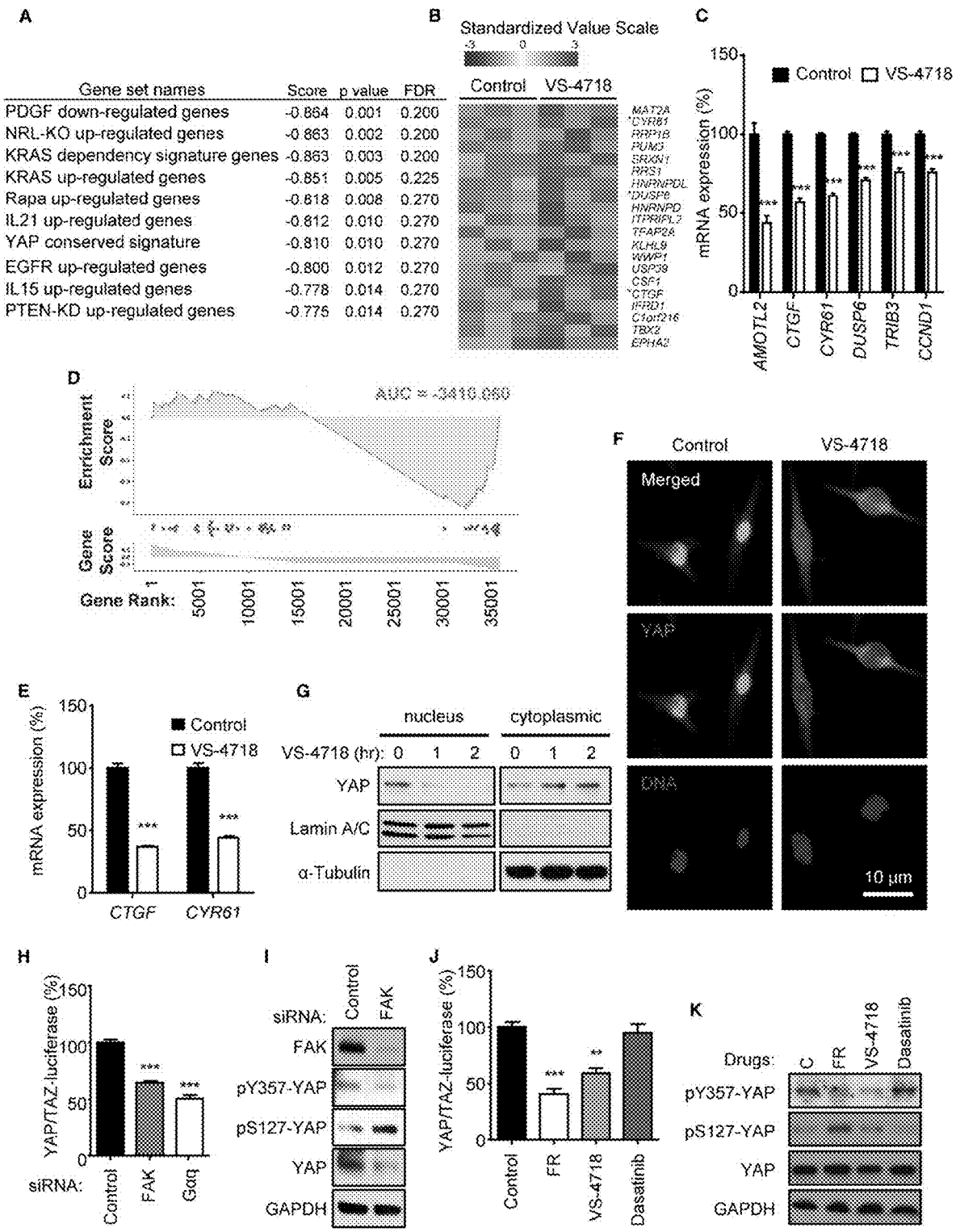
FIGS. 5A-5K show that FAK inhibition regulates the Hippo-YAP pathway in UM.
Figures 7A, 7B, 7C, 7D, 7E:
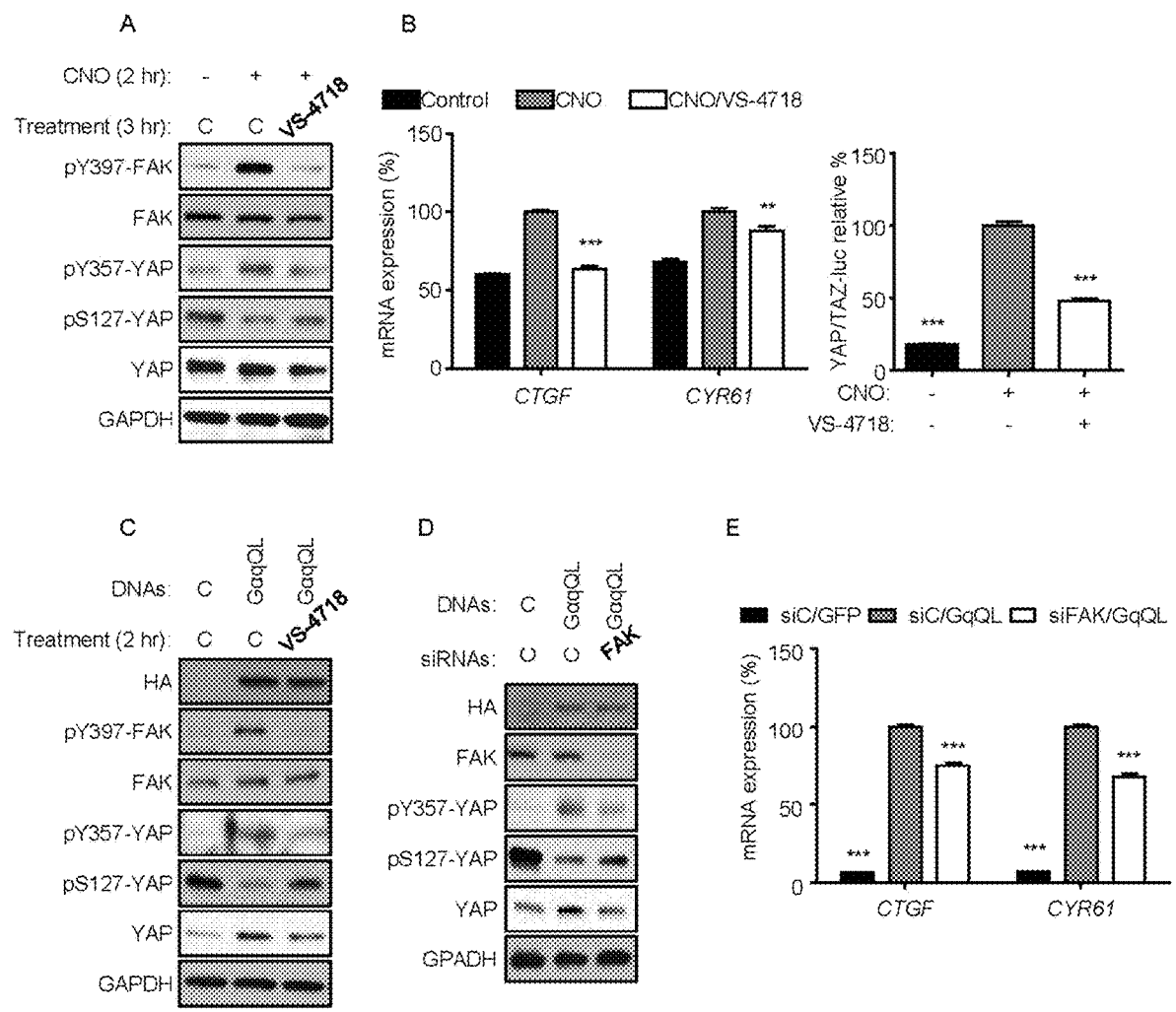
FIGS. 7A-7E show that FAK regulates the Hippo-YAP pathway.

FAK is at the intersection of multiple signaling pathways that promote cancer progression (Sulzmaier et al., 2014), but it is not clear which downstream targets of FAK play a critical role in UM. As an approach to identify key downstream targets of the Gαq– FAK signaling axis, Applicant performed transcriptomic RNA-sequencing on UM cells treated with FAKi (i.e., FAK inhibitor), and performed Gene Set Enrichment Analysis (GSEA) (Subramanian et al., 2005) to characterize the transcriptional effects of inhibiting Gαq and FAK at the pathway level using over 10,000 gene sets from the MSigDB (Molecular Signatures Database), including two sub-collections of oncogenic signatures and hallmark gene sets that Applicants added to the database (Liberzon et al., 2015). In spite of this large collection of transcriptional regulated genes, only 20 oncogenic signature gene sets were significantly repressed and 5 were activated by FAKi in UM cells (FIGS. 5A and 6A). These include the downregulation of genes described as stimulated by KRAS and EGFR and cytokines such as IL21 and IL15, consistent with the likely role in the activation of growth promoting pathways by FAK (Sulzmaier et al., 2014). FAKi also reduced the expression of genes repressed by JAK2, p53, and BMI, suggesting that FAK inhibition may trigger a p53-response and stimulate BMI and JAK2, all of which may contribute to FAK-dependent cell growth and warrant further investigation. One intriguing observation was that FAKi treatment resulted in a significant downregulation of YAP-signature genes (Zhao et al., 2008) (FIGS. 5A-5D, 6A and 6B). The involvement of Hippo/YAP signaling in cancer progression as well as previous work demonstrating the key role of YAP signaling in uveal melanoma (Feng et al., 2014b; Yu et al., 2014a; Yu et al., 2014b) led us to pursue this specific gene signature. To validate these findings, Applicant performed qPCR for the classical YAP-target genes CTGF and CYR61 in UM cells and found significant reduction in the presence of FAKi and knockdown of FAK or Gαq (FIGS. 5E, 6C and 6D). Applicant also found that FAKi clearly diminished YAP nuclear accumulation through quantification of anti-YAP staining and western blot analysis of nuclear and cytoplasmic cellular fractions (FIGS. 5F. 5G and 6E). Applicant further confirmed the functional impact of FAKi and FAK knock down on YAP by performing YAP/TAZ luciferase reporter assays, and using Gαq inhibition and knock down as a control (FIGS. 5H-5K, see FIGS. 3D and 3E for knock down validation). Interestingly, inhibition of Gαq or FAK or siRNA-mediated FAK knockdown repressed YAP phosphorylation on tyrosine 357 (Y357) and increased phosphorylation on serine 127 (S127), which is one of the main repressive targets of Hippo signaling (Pan, 2010) (FIGS. 5I and 5K). Applicant recapitulated these findings in heterologous systems, using HEK293 cells expressing Gαq-DREADD stimulated with CNO and HEK293 cells expressing GαqQL. In both cases, FAK inhibition or knockdown reduced YAP pY357 and increased pS127, and reduced mRNA levels of YAP targets and YAP activity measured by luciferase reporter assay (FIGS. 7A-7E), similar to UM cells. Inhibition of SRC in UM cells had no impact on YAP activity, measured by YAP/TAZ luciferase reporter assay, and failed to promote changes in YAP phosphorylation status (FIGS. 5J and 5K). Together, these results suggest that Gαq and FAK regulate YAP activation in UM, and that this process is likely independent of SRC.

FAK Regulates YAP Activation Through YAP Tyrosine Phosphorylation and Inhibition of Hippo Core Kinases.

Figures 8A, 8B, 8C, 8D, 8E, 8F:
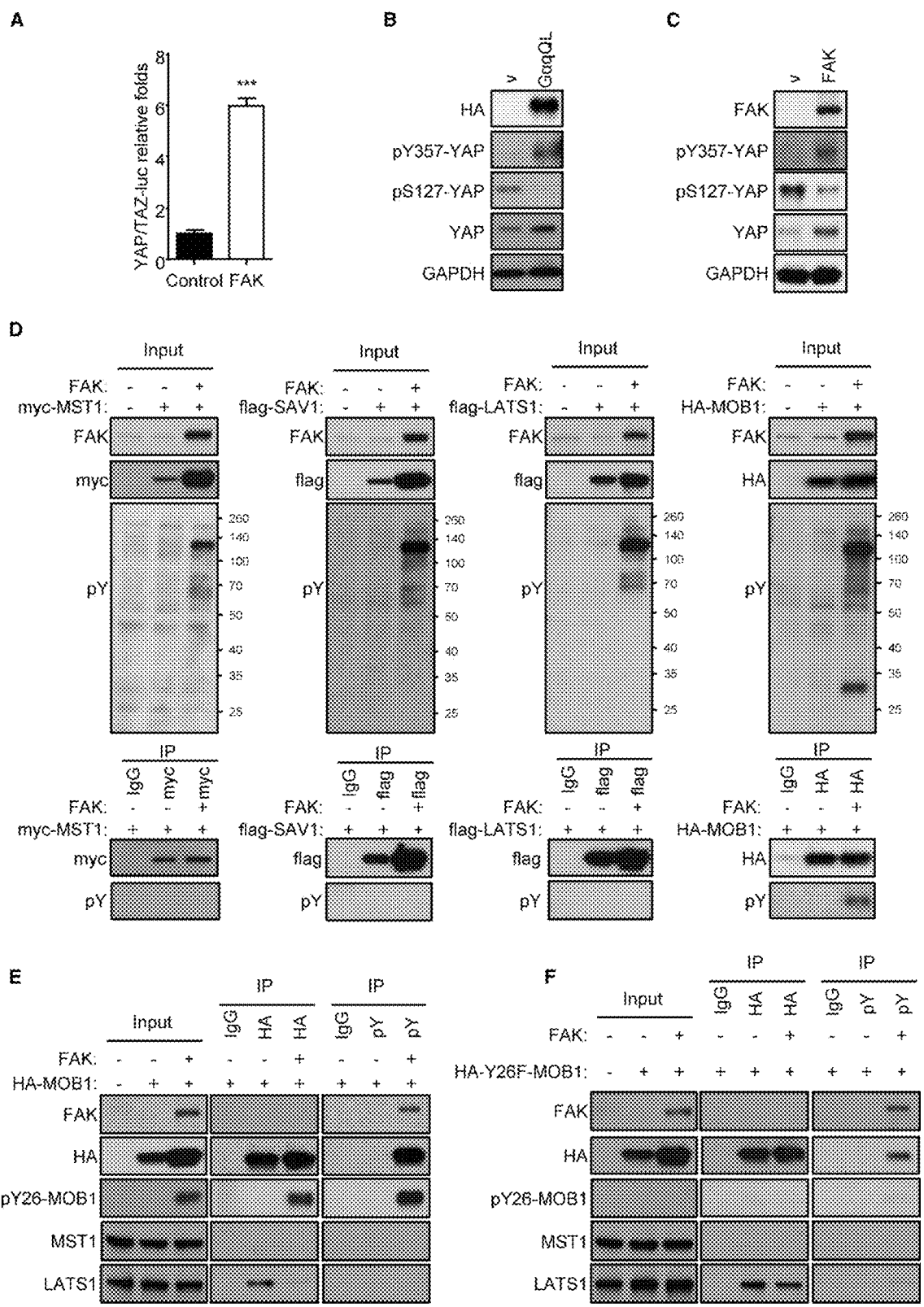
FIGS. 8A-8F show that FAK regulates YAP activation through MOB-Y26 phosphorylation, disrupting the core Hippo kinase signaling pathway.

Applicant next explored whether FAK could control YAP directly, and found that overexpression of FAK in HEK293 cells leads to a significant increase of YAP activity (FIG. 8A). It is well-established that YAP activity and stability is tightly controlled by its phosphorylation on a number of residues (Moroishi et al., 2015; Yu et al., 2015). To define the phosphorylation state of YAP in the context of aberrant Gαq signaling, Applicant expressed GαqQL and active FAK in HEK293 cells. Overexpression of GαqQL or FAK led to increased YAP protein level, diminished YAP pS127, and increased YAP pY357 (FIGS. 8B and 8C).

Figure 9A:
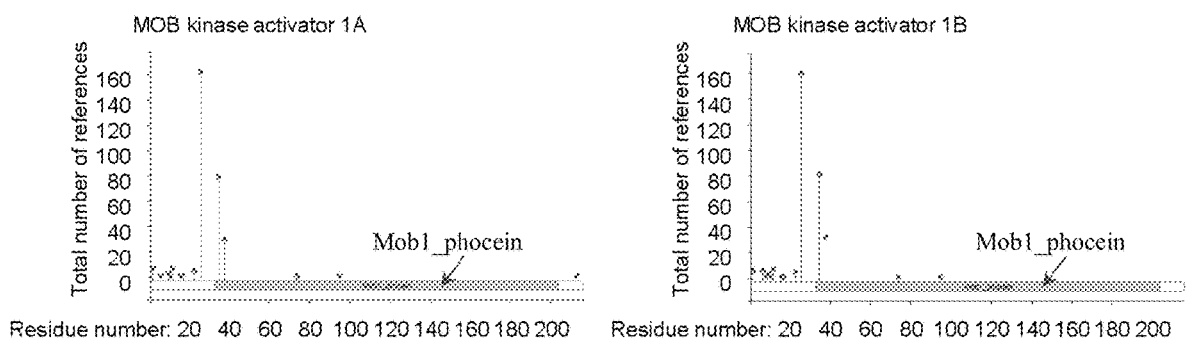
FIGS. 9A-9C show that FAK regulates YAP activation through MOB-Y26 phosphorylation.
Figure 9B:
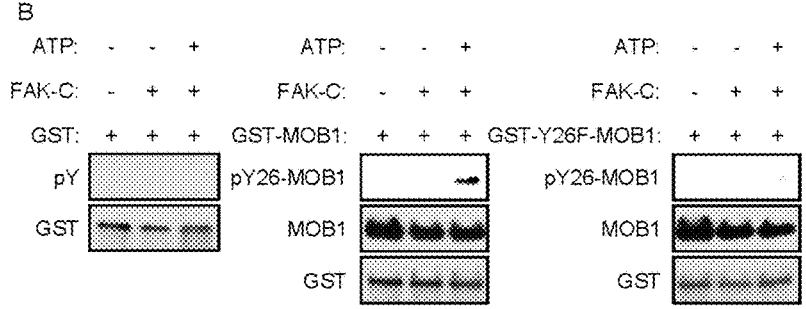
Figure 9C:
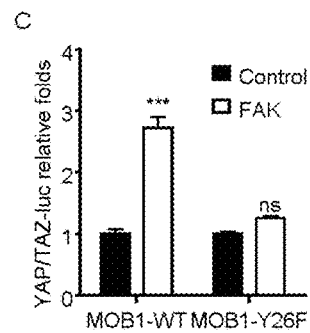

Regarding the changes in YAP pS127 levels, Applicant hypothesized that FAK may also repress inhibitory signals to YAP from the Hippo pathway through direct phosphorylation on the core kinases of the Hippo pathway. In the canonical Hippo pathway, MST1/2 kinases bound to their regulatory protein SAV1 to activate the LATS1/2 kinases (collectively referred to as LATS) as part of a complex with MOB1A/B. LATS in turn phosphorylates YAP (or in certain cells TAZ) at multiple serine residues, including S127, leading to YAP inactivation by cytoplasmic retention and subsequent degradation (Moroishi et al., 2015; Pan, 2010; Yu et al., 2015). By a systematic analysis of the tyrosine phosphorylation status of each Hippo core kinase cascade component after co-transfection with FAK, Applicant found only MOB1A to be tyrosine phosphorylated, as judged by its detection with anti-phosphotyrosine antibodies in tagged MOB1A immune precipitates (FIG. 8D). MOB1 plays a critical regulatory role in the Hippo signaling cascade by transferring the upstream signal from the kinase complex of MST1/SAV1 to LATS (Meng et al., 2016). Consistent with our findings, scanning through large phosphoprotein databases (PhosphoSitePlus® PTM Resource), Applicant found that Y26 on MOB1A/B is conserved among mammals, and that this particular residue is phosphorylated in numerous high-throughput phosphoproteomic datasets (n=161) (FIG. 9A). To interrogate the functional impact of this phosphorylation on MOB1, Applicant transfected HEK293 cells with HA-MOB1 and performed anti-HA and anti-pY immunoprecipitation (IP) assays. Applicant found that an anti-pY26 MOB1 antibody recognized MOB1 only when co-transfected with FAK, which was abolished upon mutation of Y26 on MOB1 to Y26F (FIGS. 8E and 8F), thus serving as a specificity control. Applicant further verified that FAK was able to directly phosphorylate MOB1 on its Y26 by in vitro kinase reaction using purified recombinant proteins (FIG. 9B). When exploring the consequences of this post translational modification in the assembly of Hippo kinase complexes, Applicant found that phosphorylation on Y26-MOB1 by FAK dissociates the MOB1/LATS complex (FIG. 8E). Strikingly, mutation of Y26 of MOB1 to Y26F rescued FAK-induced dissociation from LATS1 (FIG. 8F) and abolished YAP activation by FAK (FIG. 9C). Together, these data suggest that FAK regulates MOB1 Y26 phosphorylation, resulting in the dissociation of the functional MOB1/LATS complex, preventing Hippo-dependent inhibition of YAP and thereby promoting YAP activity.

FAK Inhibition Results in Increased MOB1/LATS Association and Signaling and Reduced YAP Protein Stability in UM.

Figures 11A, 11B, 11C, 11D, 11E:
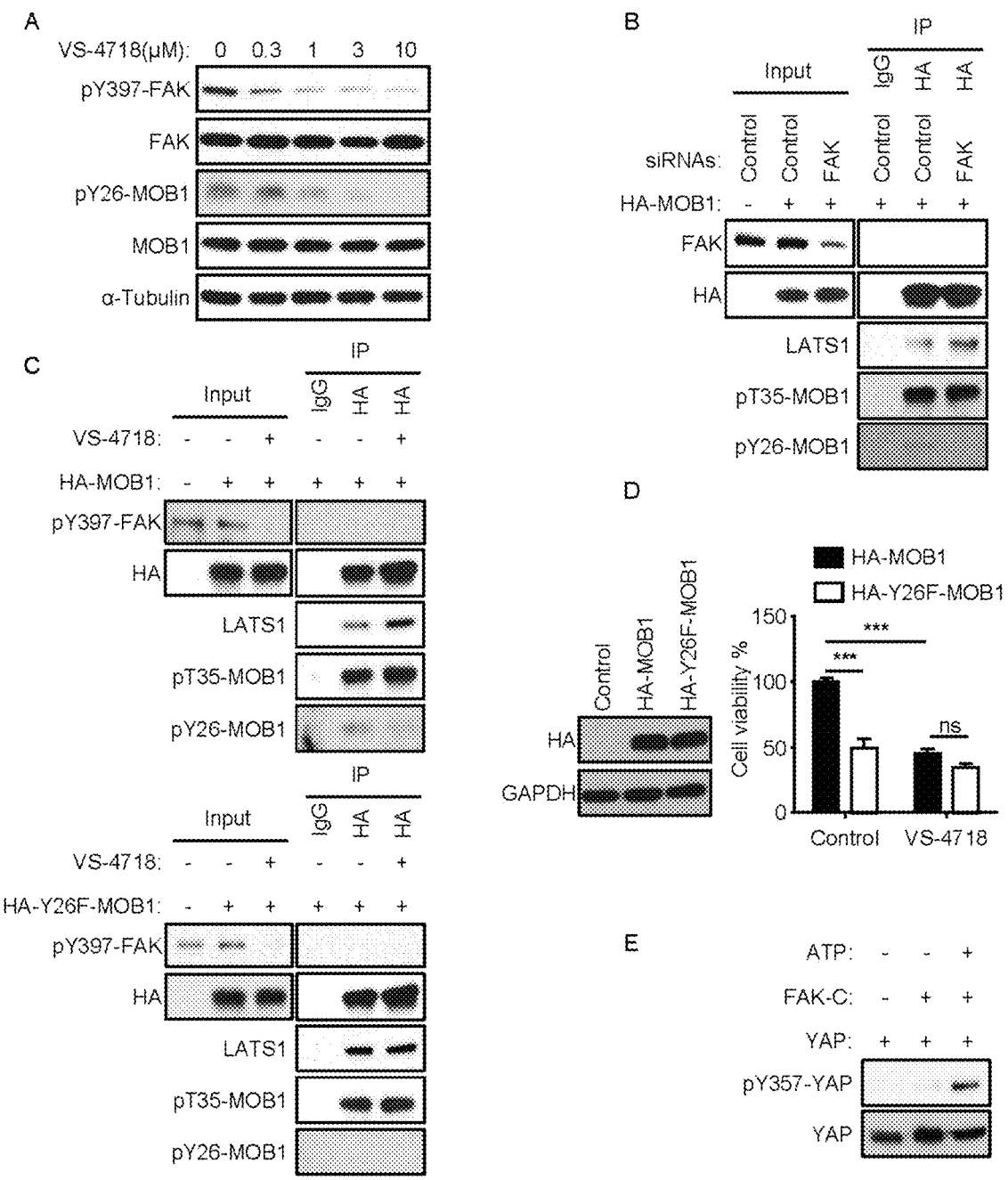
FIGS. 11A-11E provide that inhibition of FAK causes YAP inhibition.

To study the effect of FAK inhibition on the Hippo pathway in UM cells, Applicant examined the phosphorylation status of key Hippo pathway components after treated with FAKi. Applicant observed an increase of pS127-YAP, p909-LATS1, p1079-LATS1, a dose-dependent decrease in pY26 MOB1, and in line with our previous data, enhanced MOB1/LATS interaction (FIGS. 10A, 10B and 11A). In contrast, the MOB1-Y26F mutant demonstrated constitutively strong interaction with LATS independent of FAKi treatment (FIGS. 11B and 11C). Expression of MOB1-Y26F in UM cells phenocopied FAKi treatment as it diminished cell proliferation that could not be further reduced by FAKi (FIG. 11D). Of interest, however, Applicant did not observe an increase in p-MST1 in response to FAK inhibition (FIG. 10A), nor a change in phosphorylation of MOB1 at T35, the main target of MST1 on MOB1 (Meng et al., 2016) with FAKi or knockdown of FAK (FIGS. 11B and 11C). This suggests that in UM, FAK regulates the link between LATS1 and YAP through MOB1, acting downstream from MST1 rather than controlling MST1 (Hippo) activity. In conjunction, Applicant found FAK was able to phosphorylate YAP at Y357 in vitro, (FIG. 11E), a post-translational modification that has been shown to regulate YAP stability and activity (Li et al., 2016; Taniguchi et al., 2015), and aligned with this finding, that FAK inhibition also caused diminished phosphorylation of Y357-YAP in UM cells (FIG. 10A). Indeed, Applicant confirmed that long-term (up to 36 hours) FAK inhibition caused YAP protein downregulation (FIG. 10C). Furthermore, LATS1/2 knockdown was sufficient to rescue from the growth inhibition by FAKi in UM cells (FIG. 10D), supporting that YAP signaling plays a key role in growth promotion downstream from FAK in UM cells. Altogether, our data suggest that FAK drives UM cell growth through promotion of YAP activity by coordinating the previously described F-actin-mediated release of YAP from AMOT, which enhances the pool of cytosolic YAP and enables its nuclear translocation (Feng et al., 2014b), with the release of the inhibitory Hippo kinase cascade through the FAK-mediated phosphorylation of MOB1 and the concomitant tyrosine phosphorylation and stabilization of YAP (FIG. 10E).

FAK Represents a Therapeutic Target in UM.

Figures 12A, 12B, 12C, 12D, 12E, 12F, 12G, 12H:
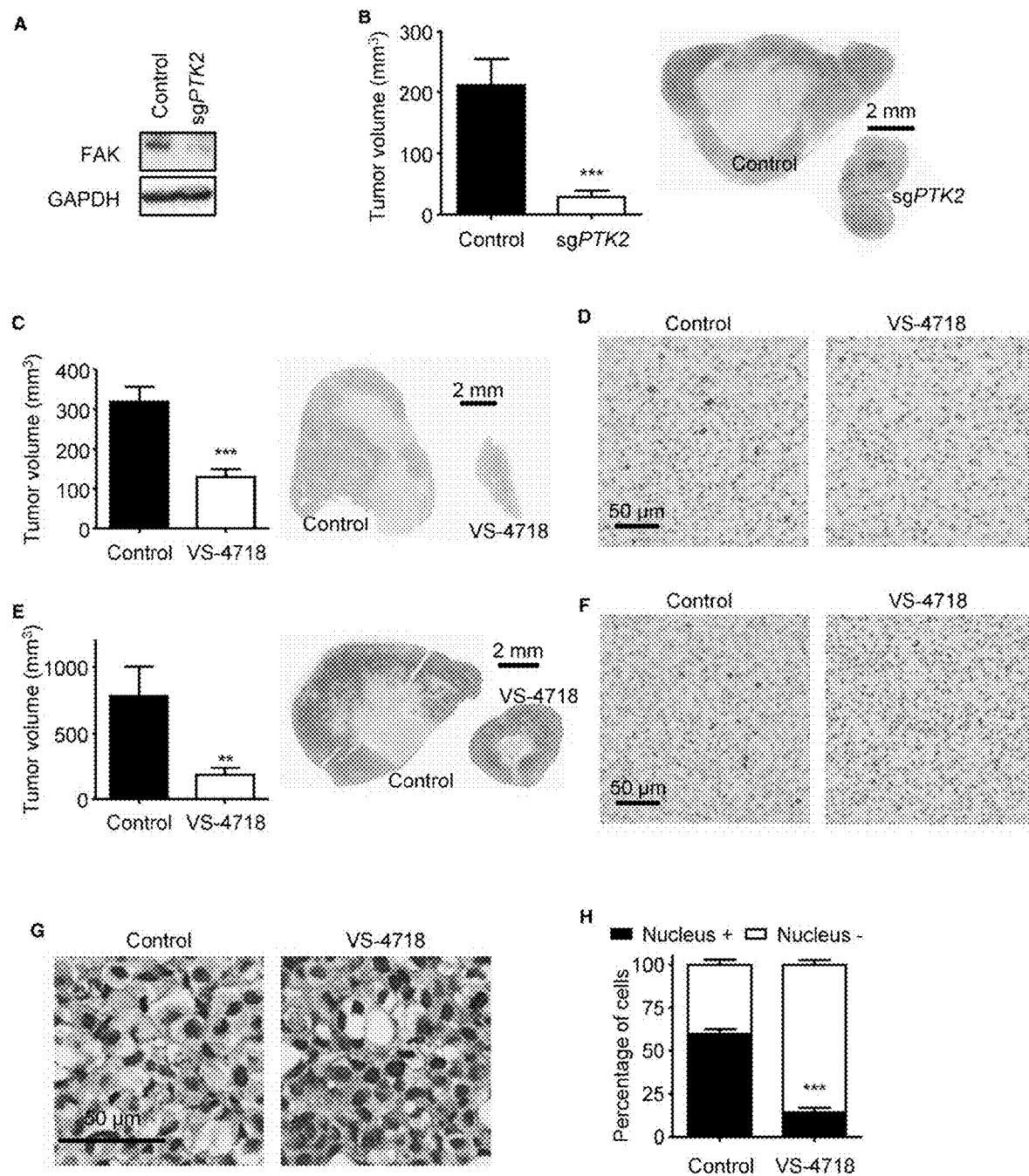
FIGS. 12A to 12H show that FAKi in UM inhibits YAP-dependent UM tumor growth.

Applicant next tested the potential of FAK inhibition for UM treatment. For these studies, Applicant first used lentiviral-delivered Cas9-sgPTK2 to knockout (KO) PTK2 in UM cells (FIG. 12A). Most UM cells did not survive after genome editing of PTK2 (not shown), only mass cultures of Mel270 targeted for PTK2 grew in culture after puromycin selection, displaying nearly abolished FAK protein levels (FIG. 12A). Re-expression of FAK under control of a doxycycline-inducible promoter was sufficient to rescue cell viability in UM cells in which FAK expression was reduced (FIG. 13). Applicant observed that PTK2 KO cells developed only very small tumors (FIG. 12B), suggesting that FAK activation is important for UM tumor growth in vivo. These observations further support the therapeutic potential of targeting FAK for UM. While there are multiple FAKi under clinical evaluation (Sulzmaier et al., 2014), VS-4718, chosen for our studies, was specifically designed for oral administration. Applicant found that VS-4718 treatment reduces both UM tumor size and cell proliferation in two different UM tumor models (FIGS. 12C-12F). Applicant observed clearly increased cytoplasmic retention of YAP in VS-4718 treated tumors, consistent with our previous findings that FAK controls YAP-activity in UM cells (FIGS. 12G and 12H). These results suggest that the pharmacological inhibition of FAK may represent a viable therapeutic approach for the treatment of patients with UM harboring increased YAP activity.

DISCUSSION

The generation of massive quantities of genomic, epigenomic and proteomic data has greatly enhanced our understanding of oncogenesis and cancer as a cellular state. The development of bioinformatics pipelines to predict nodes of connectivity between transcriptional and signaling networks can expedite efforts to identify and exploit molecular vulnerabilities for the treatment of cancer. Without wishing to be bound by the theory, Applicant thus hypothesized that focusing on a cancer type specifically driven by few activating (Gαq) mutations may serve as a good testbed for studying such an approach, harnessing a SL-based integrated bioinformatics analysis to uncover potential oncogenic signaling mechanisms controlled by Gαq and target them. In this study, Applicant demonstrate that FAK acts as a critical oncogenic signaling node in UM-mediating Gαq–driven regulation of the Hippo/YAP pathway and enabling the promotion of an oncogenic state. Applicant provide evidence that FAK destabilizes interactions between key core Hippo pathway members thereby activating YAP in an MST1 Hippo)-independent manner. Furthermore, Applicant show that the oncogenic activity of FAK in UM is targetable by clinically relevant therapeutic agents.

The transformative potential of Gαq signaling was established in the early 1990s (Gutkind et al., 1991; Kalinec et al., 1992) however, the precise signaling events by which Gαq and its linked receptors transduce sustained proliferative signals is not yet well defined. This is due in part to the large number of second messenger generating systems and signaling events that can be perturbed upon Gαq activation. The activation of these second messenger systems and their direct targets, including ion channels and kinases such as PKC, CAMKs and MAPK, are responsible for most of the rapid physiological responses elicited by GPCRs (Griner and Kazanietz, 2007; Howe, 2011; Julius and Nathans, 2012; Newton, 2010; Prevarskaya et al., 2011; Rozengurt, 2007; Sassone-Corsi). Recent studies have identified additional members of this network for UM, highlighting the role of GEFs such as RasGRP3 in MAPK activation (Chen et al., 2017). Despite this link, therapeutic strategies targeting MAPKs have yet to be successful. Clinical trials demonstrated that MEK inhibition with selumetinib or trametinib, as single agents or in combination with Dacarbazine, has little impact on the overall survival of UM patients (Carvajal et al., 2018; Carvajal et al., 2014). This suggests that although MEK/MAPK networks activated by PLCβ may contribute to UM initiation, they may not be critical for the maintenance of tumorigenic potential in UM and that instead inhibition of other Gαq-regulated pathways may be more effective than MEK/MAPK inhibitors as single agents or as part of novel drug combinations.

Contrary to the transient nature of signal transmission through PLCβ, genome-wide RNAi screens revealed that the signaling events driven by Gαq that result in aberrant cell proliferation depends on highly specific protein-protein interactions, rather than solely on diffusible second-messenger systems. Specifically, prior systems biology approaches have identified the RhoGEF TRIO as critical for activating Gαq-driven AP-1-regulated transcriptional networks independently of PLCβ to achieve sustained stimulation of proliferative pathways (Vague et al., 2013). Further work has shown that this pathway converges in the activation of YAP and that YAP activation is critical for oncogenic potential of UM (Feng et al., 2014a; Feng et al., 2014b; Yu et al., 2014a). The Hippo/YAP cascade is a key growth-regulating pathway in normal cellular physiology (Bhatt et al., 2010; Moroishi et al., 2015; Yu et al., 2015). Unsurprisingly, dysregulation of the Hippo pathway is seen frequently in cancer; however, its core components are rarely mutated (Martin et al., 2018; Moroishi et al., 2015). Rather, external pressures from upstream oncogenes typically drive YAP-dependent cell proliferation. Identifying the key molecular players that facilitate oncogenic signaling through Hippo/YAP pathway may also uncover potential network vulnerabilities. Interestingly, inhibition of PLCβ does not impact the activation of YAP after Gαq stimulation (Feng et al., 2014b). Together, these findings suggest that the canonical Gαq-PLCβ-MAPK signaling axis may be critical for tumor initiation rather than tumor maintenance and that opportunities for intervention may lie within the distinct signaling circuitry transduced through TRIO.

Applicant sought to define the distinct molecular framework involved in UM tumor maintenance by taking advantage of a bioinformatics pipeline designed to identify molecular vulnerabilities based on the prediction of synthetic lethal genetic interactions. The top candidate of our screen, FAK, is a non-receptor tyrosine kinase whose role as a downstream target of Gαq has been well established by biochemical studies (Gutkind and Robbins, 1992); however, the contribution of FAK as a mediator of oncogenic Gαq signaling has not been previously explored. Our finding that FAK is rapidly activated by Gαq-linked GPCRs and the oncogenic mutant Gαq through TRIO and RhoA, rather than PLCβ prompted us to focus on the possibility that FAK may represent an integral component of the non-canonical pathway by which Gαq regulates aberrant cell growth. Applicant found that inhibition of FAK was sufficient to reduce UM cell proliferation, and if prolonged, to trigger apoptotic cell death. This response was unanticipated as FAK inhibitors often have limited activity in most cancers as single agents but instead synergize with cytotoxic agents, as Applicant have shown for ovarian cancer that overexpresses FAK as a typical example (Sulzmaier et al., 2014). Applicant hypothesized that as compared to other cancer types with FAK overexpression, the compounding impact of PTK2 copy number gain and overexpression together with Gαq– driven FAK activity in UM creates a unique cellular state that may be highly dependent on the activity of FAK and therefore highly sensitive to FAK inhibition. This convergence of computational predictions, biochemical, and genetic information enabled the discovery of the therapeutic potential of inhibiting FAK for UM treatment.

Applicant's RNA-seq studies examining the functional role of FAK in UM revealed an enrichment of several oncogenic signatures including KRAS and EGFR-regulated genes; however, YAP conserved signature was among the top hits. FAK has been recently linked to YAP activity in mechanotransduction and in the coordination of cell proliferation and differentiation in mouse incisors during development (Hu et al., 2017; Lachowski et al., 2018). However, the underlying cell-context specific and developmental mechanisms are still not fully understood. Applicant provides evidence that in UM the role of FAK converges on promoting YAP activity through the tandem inhibition of Hippo pathway signals by phosphorylation of Y26 of MOB1 and Y357 of YAP. In the case of YAP phosphorylation, these observations extend prior studies indicating the role of JAK2 and SRC in Y357 phosphorylation (Li et al., 2016; Taniguchi et al., 2015). However, downstream from FAK, Applicant observed both tyrosine-phosphorylated YAP and a decrease in pS127 YAP, the latter a direct target of the Hippo signaling pathway. In this regard, there is increasing evidence suggesting that Hippo signaling is tightly regulated by the assembly and dissociation of key signaling complexes. Our interrogation of these complexes in response to FAK activation led to the finding that FAK phosphorylates MOB1 on Y26, resulting in the disassembly of the MOB1/LATS complex and disruption of the Hippo pathway downstream from MST1, effectively rewiring the molecular mechanisms controlling YAP activity. Mutation of Y26 of MOB1 is sufficient to abolish the effect of FAK. Whereas further work may be required to establish the structural basis for this inhibition, as well as alternative FAK-driven pathways in mechanotransduction and development, our findings support that disruption of the MOB1/LATS signaling complex by FAK is a key regulatory step resulting in YAP activation by Gαq. Ultimately, this mechanism may coordinate the Gαq-induced increase in cytosolic free YAP, which is mediated by Rho-induced actin polymerization (Feng et al., 2014b), with Hippo kinase cascade inhibition through the FAK-mediated phosphorylation of MOB1, resulting in the YAP-dependent UM cell growth.

The current lack of effective treatments for primary or metastatic UM leaves a large therapeutic gap for patients and clinicians underscoring an urgent need for the identification of additional pharmacological targets for therapeutic intervention. As YAP-targeting strategies have remained elusive thus far, the success of FAK inhibition in our in vivo models in the context of previously established success and safety of FAK inhibitors in human clinical trials highlight the translational potential of our findings and establish FAK as a therapeutic target for the treatment of UM. Towards this end, the application of systems-level and bioinformatics investigation will be a powerful strategy to identify precision treatment options for UM and a myriad of Gαq-driven diseases.

Methods, Experimental Model and Subject Details

TABLE 1

| REAGENT or RESOURCE | SOURCE | INDENTIFIER |
|---|---|---|
| Antibodies | | |
| YAP | Cell Signaling Technology, MA | 14074 |
| pS127-YAP | Cell Signaling Technology, MA | 4911 |
| pS909-LATS1 | Cell Signaling Technology, MA | 9157 |
| pT1079-LATS1 | Cell Signaling Technology, MA | 8654 |
| LATS1 | Cell Signaling Technology, MA | 3477 |
| p-MST1/MST2 | Cell Signaling Technology, MA | 3681 |
| MST1 | Cell Signaling Technology, MA | 3682 |
| GAPDH(14C10) | Cell Signaling Technology, MA | 2118 |
| α-Tubulin | Cell Signaling Technology, MA | 3873 |
| pY | Cell Signaling Technology, MA | 9411 |
| HA-tag-HRP | Cell Signaling Technology, MA | 2999 |
| HA-tag | Cell Signaling Technology, MA | 3724 |
| myc-tag | Cell Signaling Technology, MA | 2278 |
| pY397-FAK | Cell Signaling Technology, MA | 8556 |
| FAK | Cell Signaling Technology, MA | 3285 |
| cleaved PARP | Cell Signaling Technology, MA | 9541 |
| p-ERK 1/2 | Cell Signaling Technology, MA | 4370 |
| ERK 1/2 | Cell Signaling Technology, MA | 4696 |
| MOB1 | Cell Signaling Technology, MA | 13730 |
| pT35-MOB1 | Cell Signaling Technology, MA | 8699 |
| Gαq(E-17) | Santa Cruz Biotech., CA | sc-393 |
| FAK(C-20) | Santa Cruz Biotech., CA | sc-558 |
| RhoA | Cell Signaling Technology, MA | 2117 |
| TRIO(H120) | Santa Cruz Biotech., CA | sc-28564 |

TABLE 1-continued

| REAGENT or RESOURCE | SOURCE | INDENTIFIER |
|---|---|---|
| Rac1 | BD Biosciences, CA | 610651 |
| pY357-YAP | Abcam, MA | ab62751 |
| LATS2 | Bathyl Laboratories, TX | A300-479A |
| pY26-MOB1A | Signalway Antibody, MA | 12878 |
| flag-tag-HRP | Sigma-Aldrich, MO | A8592 |
| Ki67 | DAKO, CA | M724029-2 |
| Baterial strains | | |
| DH5alpha Competent *E. coli* | BioPioneer, CA | GACC-96 |
| stbl3 Competent *E. coli* | Thermo Fisher | C737303 |
| siRNAs | | |
| Non-targeting | Dharmacon, CO | D-001810-0X |
| Gaq | Sigma-Aldrich, MO | SASI_Hs01_00231793 |
| FAK | Thermo Fisher, MA | s11485 |
| AKT1 | Thermo Fisher, MA | s659 |
| MGLL | Thermo Fisher, MA | s22380 |
| MTHFD1 | Thermo Fisher, MA | s9032 |
| CDK1 | Thermo Fisher, MA | s464 |
| SIRT1 | Thermo Fisher, MA | s223591 |
| PSMB5 | Thermo Fisher, MA | s11354 |
| TRIO | Dharmacon, CO | L-005047-00-0005 |
| RhoA | Dharmacon, CO | L-003860-00-0005 |
| Rac1 | Dharmacon, CO | L-003560-00-0005 |
| LATS1 | Sigma-Alrich, Mo | Hs01_00046128 |
| LATS1 | Sigma-Aldrich, MO | Hs01_00158803 |
| DNAs | | |
| pCMV-myc-MST1 | Addgene | 8847 |
| pCMV2-FLAG-SAV1 | Addgene | 18970 |
| pcDNA3-HA-MOB1 | Addgene | 32835 |
| pcDNA3-HA-Y26F-MOB1 | Generated in-lab | NA |
| pLENTi-HA-MOB1 | Generated in-lab | NA |
| pLENTi-HA-Y26F-MOB1 | Generated in-lab | NA |
| pGEX-HA-MOB1 | Generated in-lab | NA |
| pGex-HA-Y26F-MOB1 | Generated in-lab | NA |
| pLVX-TetOne-FLAG-FAK | Addgene | 18971 |
| BxGTIIC-luciferase | Addgene | 34615 |
| REAGENT | | |
| alamarBlue ™ Reagent | Grand Island, NY | DAL1100 |
| FAK Kinase Enzyme System | Promega | V1971 |
| YAP1 Recombinant Protein | Abnova | H00010413-P01 |

TABLE 1-continued

| REAGENT or RESOURCE | SOURCE | INDENTIFIER |
| --- | --- | --- |
| Glutathione Sepharose 4B | GE Healthcare | 17-0756-01 |
| N/C Extraction Reagents | ThermoFisher | 78833 |
| U73122 | Sigma-Aldrich, MO | U6756 |
| GF109203X | Sigma-Aldrich, MO | G2911 |
| Software and Database | | |
| ISLE | Lee et al 2018 | http://www.github.com/jooslee/ISLE |
| PhosphoSitePlus | Cell signaling technology, MA | |
| Primers | | |
| Y26-MOB1-F(SEQ ID NO: 7) (For point mutation) | Integrated DNA Technologies | CATGTTTTAAGAGTTCAAACTGATGAGATCCTTCAGGGATATTCTTC |
| Y26F-MOB1-R(SEQ ID NO: 8) (For point mutation) | Integrated DNA Technologies | GAAGAATATCCCTGAAGGATCTCATCAGTTTGAACTCTTAAAACATG |
| GAPDH-F(SEQ ID NO: 9) | Integrated DNA Technologies | GAGTCAACGGATTTGGTCGT |
| GAPDH-R(SEQ ID NO: 10) | Integrated DNA Technologies | TTGATTTTGGAGGGATCTCG |
| CTGF-F(SEQ ID NO: 11) | Integrated DNA Technologies | GTTTGGCCCAGACCCAACTA |
| CTGF-R(SEQ ID NO: 12) | Integrated DNA Technologies | GGCTCTGCTTCTCTAGCCTG |
| CYR61-F(SEQ ID NO: 13) | Integrated DNA Technologies | CAGGACTGTGAAGATGCGGT |
| CYR61-R(SEQ ID NO: 14) | Integrated DNA Technologies | GCCTGTAGAAGGGAAACGCT |

Cell Lines, Culture Procedures and Chemicals

HEK293 and HEK293T cells were cultured in DMEM (Sigma-Aldrich Inc., MO) containing 10% FBS (Sigma-Aldrich Inc., MO) and 1× antibiotic/antimycotic solution (Sigma-Aldrich Inc., MO). Culture conditions for UM cells (OMM1.3, OMM1.5, MEL202, Mel270 and 92.1) have been described elsewhere (Schmitt et al., 2007; Zuidervaart et al., 2005). SK-MEL-28 cells were purchased from ATCC and cultured following ATCC recommendations in EMEM containing 10% FBS. VS-4718 (PND-1186) was purchased from MedChemExpress (MCE) pre-prepared as a 10 mM solution in DMSO. FR900359 (FR) was graciously supplied by the lab of Dr. Evi Kostenis.

DNA Constructs

Plasmids pCEFL-HA, pCEFL-HA-GαqQL, pCEFL-Gαq-DREADD, pCEFL-3×-Flag-*Renilla*-luciferase were described previously (Marinissen et al., 2003; Teramoto et al., 2003). pCEFL-myr-FAK was described previously (Chikumi et al., 2002; Igishi et al., 1999). Plasmids pCMV-myc-MST1 (Addgene #8847, originally from Joseph Avruch's lab), pCMV2-FLAG-SAV1 (Addgene #18970, originally from Marius Sudol' lab), pcDNA3-HA-MOB1 (Addgene #32835, originally from Kunliang Guan's lab), p2×FLAG-CMV2-LATS1 (Addgene #18971, originally from Marius Sudol's lab) and 8×GTIIC-luciferase (Addgene #34615, originally from Stefano Piccolo's Lab).

Bioinformatic Analysis (Identifying Clinically-Relevant Gαq-Specific Vulnerabilities of UM).

To identify the clinically-relevant vulnerabilities for UM, Applicant performed an analysis that follows the main concepts of our previous work, ISLE (Lee et al., 2018) with modifications for Gαq-driven UM. Applicant analyzed the cancer genome atlas (TCGA) (Cancer Genome Atlas Research et al., 2013) UM samples with skin cutaneous melanoma (SKCM) samples as control together with the large-scale functional (Cheung et al., 2011; Cowley et al., 2014; Marcotte et al., 2012; Marcotte et al., 2016) and drug response (Barretina et al., 2012; Friedman et al., 2015; Iorio et al., 2016) screens. Applicant downloaded the gene expression, copy number alteration, and patient survival and other clinical characteristics of TCGA UM and SKCM cohort from cBioPortal (Gao et al., 2013) on Feb. 1, 2017. Applicant used 80 UM samples and 287 SKCM samples for our analysis. Applicant obtained the data from cBioPortal as it integrates the mutation analysis from different TCGA centers to avoid center specific bias in mutation calls.

Applicant denoted a tumor sample as Gαq+ if any of the Gαq-family genes (GNAQ, GNA11 and CYSLTR2) are either mutated or amplified in the given sample (amplification, if the Gistic score is greater than 0.35), and as Gαq− if the sample lacks GNAQ, GNA11 and CYSLTR2 genes mutation and amplification. First, Applicant selected important genes in UM, that are (i) highly over expressed in Gαq+UM (n=77, excluding 3 Gαq− cases) with respect to control Gαq− SKCM TCGA samples (n=209) using Wilcoxon rank sum test (p<0.05). Applicant filtered out (ii) those genes that are overexpressed in UM compared to all SKCM samples irrespective of Gαq status (Wilcoxon rank sum p>0.05), leading to 1,146 out of total 18,087 satisfying both conditions. Applicant tested whether these genes show significant overlap with the genes overexpressed in Gαq+ skin melanoma TCGA samples (n=78, mutation=16, amplification=65, overlap=13) compared to Gαq− SKCM samples using hypergeometric test, truncating the hypergeometric p values to $10^{-16}$.

Second, Applicant further selected the genes whose inactivation leads to better patient survival in UM, thus potential target of a therapy. Applicant used a stratified Cox proportional hazard model to evaluate the association, while controlling for available potential confounders in the dataset including patients' sex and tumor stage (Therneau and Grambsch, 2000). The inactivation of 293 genes (out of 1,146 genes that passed the previous screen) show significant association with improved patient survival.

Third, Applicant used gene essentiality (Cheung et al., 2011; Cowley et al., 2014; Marcotte et al., 2012; Marcotte et al., 2016) and drug response screens (Barretina et al., 2012; Friedman et al., 2015; Iorio et al., 2016) in a wide panel of cancer cell lines to identify the genes whose knockdown/inhibition specifically reduces Gαq+ cell viability. Applicant used the mutation and copy number data from the measurements on the cell lines in CCLE collection (Barretina et al., 2012) to determine the status of Gαq-family genes in these cell lines. Applicant performed Wilcoxon rank sum test between the essentiality or drug response values between the cell lines that are Gαq+vs. Gαq−. The essentiality or the drug inhibition identified 72 genes out of 293 genes (that passed the 2nd filter) that satisfy this condition.

Finally, Applicant prioritized the druggable targets. Applicant collected the druggable genome using the drug-to-target mapping curated in DrugBank database (Law et al., 2014) and the literature including (Barretina et al., 2012; Basu et al., 2013; Friedman et al., 2015; Gao et al., 2013; Garnett et al., 2012; Iorio et al., 2016). Our collection encompasses 756 targetable genes, including 273 targets of FDA-approved drugs, 10 targets of drugs under clinical trials, and 473 experimental drugs. Applicant further removed the genes that belong to the same chromosomes to the Gαq-family genes to avoid the confounding effect of genomic linkage. This step led to the final set of 7 targets.

Immunoblot Assay

Western blot assays were performed as described previously (Feng et al., 2014b). Western blots were developed using Immobilon Western Chemiluminescent HRP substrate (Millipore, MA) according to the manufacturer's instructions.

CRISPR-Cas9-Knockout

PTK2-sgRNA-CRISPR/Cas9-all-in-one-lentivector vector was purchased from Applied Biological Materials Inc. (Cat. K1752206). Lentivirus were prepared with HEK293T cells as the packaging cells as previously reported (Basile et al., 2004). To establish PTK2-knock out, cells were infected with the corresponding lentiviral supernatants for 16 hours, after which the media was changed to normal growth medium containing puromycin (Sigma-Aldrich Inc., MO) selection.

siRNAs Transfection

All cells were transfected using Lipofectaminex RNAiMAX Reagent (Thermo Fisher Scientific) according to manufacturer's instructions.

MOB1-Y26F Point Mutation

MOB1-Y26F point mutant was generated using the Quickchange Site-Directed Mutagenesis kit following manufacturer's instructions (Agilent Genomics, CA). pcDNA3-HA-MOB1 was used as the template and see the primers in Table 1.

Human Tumors Xenografts and VS-4718 In Vivo Treatment

All animal studies were carried out according the University of California San Diego (UCSD) Institutional Animal Care and Use Committee (IACUC)-approved protocol (S15195). Female NOD.Cg-Prkdcscid Il2rgtm1wjl/SzJ mice (commonly known as NOD acid gamma, Jackson Laboratory, Maine), 6 to 8 weeks of age and weighing 18 to 20 g, were used in the study of UM cells, housed in appropriate sterile filter-capped cages, and provided food and water ad libitum. All procedures were essentially as previously described (Feng et al., 2014b; Schrage et al., 2015; Vaque et al., 2013). Briefly, exponentially growing cultures were harvested, washed, resuspended in RPMI 1640, and $2\times10^6$ viable cells were transplanted subcutaneously into the flanks of mice. For tumor growth analysis, tumor volume was assessed as $[(LW^2/2)$; where L and W represent the length and the width of the tumor]. The animals were monitored twice weekly for tumor development. Results of animal experiments were expressed as mean±SEM of a total of tumors analyzed. To administer VS-4718 (Verastem Oncology; Needham, Mass.) to mice, 10 mg/ml VS-4718 was prepared in 0.5% carboxymethyl cellulose (CMC) (C5678, Sigma-Aldrich; St. Louis, Mo.) 0.1% Tween 80 (P1754, Sigma Aldrich; St. Louis, Mo.) in sterile water, 100 mg/kg administered via oral gavage twice daily, control group was treated with vehicle.

Immunofluorescence

Cells cultured on coverslips were washed with PBS, fixed with 3.7% formaldehyde in phosphate-buffered saline (PBS) for 30 min, and permeabilized using 0.05% Triton X-100 for 10 min. Fixed cells were blocked with 3% FBS-containing PBS for 30 min, and incubated with YAP (Cell signaling technology, MI) antibody (in 3% FBS-PBS otherwise stated) for 1 hr at room temperature. The reaction was visualized with Alexa-labeled secondary antibodies (Invitrogen, CA). Samples were mounted in PBS buffer containing Hoechst 33342 (Molecular Probes, OR) for nuclear staining. Images were acquired with an Axio Imager Z1 microscope equipped with ApoTome system controlled by ZEN 2012 software (Carl Zeiss, NY).

Luciferase Assays

Cells were co-transfected with pCEFL-3x-Flag-*Renilla*-luciferase and 8xGTIIC-luciferase (Addgene 34615) in 6-well plates overnight to the detection of the luciferase activity, using a Dual-Glo Luciferase Assay Kit (Promega, WI) and a Microtiter plate luminometer (Dynex Tech., VA).

Immunohistochemistry

The following antibodies were used for immunohistochemistry anti-Ki67 (DAKO) and anti-YAP (CST). Unstained 5 µm paraffin sections were dewaxed in Safeclear II (Fisher Scientific, PA), hydrated through graded alcohols and distilled water, and washed three times with PBS. Antigens were retrieved using or 10 mM citrate buffer boiled in a microwave for 20 min (2 min at 100% power and 18 min at 10% power). The slides were allowed to cool down for 30 min at room temperature, rinsed twice with PBS, incubated in 3% hydrogen peroxide in PBS for 10 min to quench the endogenous peroxidase. The sections were then sequentially washed in distilled water and PBS, incubated in blocking solution (2.5% bovine serum albumin in PBS) for 30 min at room temperature. Excess solution was discarded and the primary antibodies were applied diluted in blocking solution at 4° C. overnight. After washing with PBS, the slides were sequentially incubated with the biotinylated secondary antibody (1:400) (Vector Laboratories, CA) for 30 min and with the avidin-biotin complex, reconstituted according to the instruction of the manufacturer in PBS (Vector Stain Elite, ABC kit) (Vector Laboratories, CA), for 30 min at room temperature. The slides were developed in 3,3-diaminobenzidine (Sigma FASTDAB tablet) (Sigma Chemical, MO) diluted in distilled water under a microscope.

Immunoprecipitation

Cells were lysed with IP lysis buffer [10 mM Tris-Cl (pH 8.0), 150 mM NaCl, 1 mM EDTA, 0.3% CHAPS, 50 mM NaF, 1.5 mM $Na_3VO_4$, protease inhibitor (Thermo Scientific, CO), 1 mM DTT, 1 mM PMSF], and centrifuged at 16,000 g for 5 min at 4° C. Supernatants were incubated with first antibody for 1 hr at 4° C., and protein G or protein A conjugated resin for another 1 hr. Resins were then washed 3 times with lysis buffer and boiled in SDS-loading buffer.

Cell Growth Assays

Cell growth assays were performed as described previously (Yamaguchi et al., 2016). Cells were cultured in 96-well-plate and treated with drugs for 72 hr. The manufacturer's instructions of Alamar Blue Cell Viability Reagent were followed to complete the assay.

3D Cell Culture 3-dimensional cultures were performed as described previously (Tancioni et al., 2015). Briefly, 10,000 cells were embedded in 1% methylcellulose diluted in growth media and plated onto 6-well poly-hydroxyethyl methacrylic acid (poly-HEMA)-coated plates.

Generation of GST-MOB Fusion Proteins

GST fusion proteins were prepared engineered, expressed in bacteria, and purified as previously described in (Martin et al., 2018) using standard procedures.

In Vitro FAK Kinase Assay

Kinase reactions were performed as previously described in Bernard-Trifilo et al. Briefly, 1.5 µg of substrate (MOB1-GST, MOB1-Y26F-GST, GST-only control, or recombinant YAP) was resuspended in 40 uL FAK Kinase buffer (20 mM HEPES pH 7.4, 10% glycerol, 10 mM $MgCl_2$, 10 mM $MnCl_2$, and 150 mM NaCl). 5 µL magnesium/ATP cocktail (75 mM $MgCl_2$, 20 mM MOPS pH 7.2, 25 mM β-glycerol phosphate, 5 mM EGTA, 1 mM sodium orthovanadate, 1 mM dithiothreitol) with or without 50 µM ATP was added to appropriate tubes, and placed in 32° C. water bath for 15 min. Samples were boiled in sample buffer and processed on SDS-PAGE.

Nuclear and Cytoplasm Extraction

Subcellular fractionated lysates were generated using NE-PER Nuclear and Cytoplasmic Extraction Reagents (Thermo Scientific, CO) following manufacturer instructions.

Statistical Analysis

All data analysis was performed using GraphPad Prism version 7.03 for Windows (GraphPad Software, CA). The data were analyzed by ANOVA test or t-test (* $p<0.05$,  $p<0.01$, * $p<0.001$).

Example 2: New Multimodal Anticancer Treatment for Uveal Melanoma

Without wishing to be bound by the theory, Applicant hypothesized that by focusing on a unique cancer type driven by activating Gαq mutations, Applicant's studies reveal novel oncogenic signaling mechanism controlled by Gαq and how the interplay between classical and non-canonical Gαq signaling contributes to normal and aberrant cell growth. Based on our recent findings (Feng et al., 2019; Vaque et al., 2013; and Feng et al., 2014a and 2014b) and without being bound by theory, Applicant hypothesizes that the non-receptor tyrosine kinase FAK is an integral part of the non-canonical Gαq-signaling pathway initiated through TRIO and Rho GTPases, and that in turn FAK inhibition or restraining its downstream regulated pathways may represent a precision therapeutic approach for mUM, alone or as part of novel signal transduction-based precision co-targeting strategies. Applicant has now discovered that co-targeting FAK and the MEK-ERK pathway leads to the rapid apoptotic death of UM and mUM cells, resulting in UM regression and improved survival of mice bearing UM liver metastasis lesions. Indeed, Applicant discovered that MEK-ERK pathway inhibition by multiple clinical and experimental MEK inhibitors combined with FAKi shows a remarkable synergistic growth inhibitory effect in UM cells. Additionally, the novel RAF/MEK inhibitor CH5126766 (Wada et al., 2014; Knauf et al., 2018) also showed synergistic anti-proliferative effects with VS-4718 and its clinically relevant VS-6063 (known as defactinib), thus providing a strong basis for our application and a rationale and mechanistic framework for future precision therapy trials combining FAK and MEK-ERK pathways inhibitors in OM and mOM.

Targeting FAK and the MEK-ERK Network in OM and mUM

Using a synthetic biology approach and a genome-wide RNAi screen, Applicant has recently shown that Gαq activates a highly conserved Rho GTPase-TRIO signaling circuitry independently of PLC-β, the best known target of Gαq (Vague et al., 2013, Feng et al., 2014a and 2014b). Remarkably, Applicant found that this novel pathway is involved in the activation of YAP, a transcriptional co-activator regulated by the Hippo pathway, and that in turn, YAP activation is necessary for UM growth (Feng et al., 2014a and 2014b). However, there are currently no specific and safe YAP inhibitors available. Thus, there is an urgent need to understand how Gαq promotes cancer growth in order to develop new targeted (precision) therapeutic options. In a recent study, Applicant used a novel computational framework to shed light on Gαq biology and identify systems vulnerabilities for OM, based on the prediction of synthetic (dosage) lethal gene interactions (Kaelin, 2005; Hartwell et al., 1997; Brough et al., 2011; Ashworth et al., 2011; Jerby-Arnon et al., 2014; and Lee et al., 2018) of Gαq (Feng et al., 2019). This novel pipeline integrates data from large multiomics cancer datasets, including OM patient transcriptomes and genomes, with in vitro screens (datasets of gene essentiality and dependence (Marcotte et al., 2012; Marcotte et al., 2016; Cheung et al., 2011; and Cowley et al., (2014)) and druggable screens (datasets of drug response screens (Iorio et al., 2016; Basu et al., 2013)). The top predicted synthetic lethal gene with GNAQ was PTK2, suggesting the potential benefit of targeting the PTK2 gene product (a non-receptor tyrosine kinase known as FAK) in GNAQ-induced tumors.

Remarkably, aligned with our GNAQ-vulnerability prediction (above), the analysis of OM genomic alterations revealed that the PTK2 gene is amplified or overexpressed in >56% of all OM lesions, even in cases that do not exhibit amplification of the MYC proto-oncogene, which is proximal to the PTK2 locus on chromosome 8q. Indeed, UM represents the human cancer harboring the highest level of FAK overexpression (Feng et al., 2019). Furthermore, patients with high PTK2 expression (the lower line) show poorer survival than the patients with low PTK2 expression (the upper line) (FIG. 2D), aligned with its potential biological role in OM. FAK modulates cell growth, survival and movement, with phosphorylation at position Y397 representing a common marker of FAK activation (Sulzmaier et al., 201), which Applicant found to be widespread in UM (Feng et al., 2019). FAK signaling is linked to cancer stem cell survival (Schober, 2011; Shapiro et al., 2014; Williams et al., 2015), and FAK inhibitors (FAKi) in the clinic (>30 clinical trials) are well tolerated and have been recently shown to increase the response to new immune checkpoint inhibitors in cancer (Sulzmaier et al., 2014; Jiang et al., 2016). Remarkably, activation of FAK by Gq-linked receptors was initially reported by our team in the early 90s (Gutkind, 1992). This unexpected convergence of computational predictions, biochemical, and genetic information prompted us to focus on the role of this Gαq-tyrosine kinase signaling axis in UM, and specifically on the Gαq-FAK signaling network and the evaluation of FAKi for mOM treatment.

Regulation of the Novel Hippo-YAP Pathway by a Gαq Non-Canonical Signaling Route Through TRIO and FAK.

In two independent studies, the Guan and Gutkind labs provided the first demonstration that YAP activation is central to UM growth, and a suitable target for therapy (Feng et al., 2014a and 2014b; Yu et al., 2014). In the canonical Hippo pathway, MST1/2 kinases (Hippo) bound to their regulatory protein SAV1 activate the LATS1/2 kinases (collectively referred to as LATS) as part of a complex with MOB1A/B. LATS in turn phosphorylates YAP (or in certain cells TAZ) at multiple serine residues, including pS127 leading to YAP inactivation by cytoplasmic retention and degradation (Meng, 2016). Applicant provided evidence that activation of YAP by Gαq involves a novel TRIO-RhoA regulated pathway controlling actin polymerization (F-actin) and the release of YAP from an inactive pool associated with an F-actin binding protein, AMOT, concomitant with Hippo pathway inhibition (Feng et al., 2014a; Feng et al., 2014b). Free YAP translocates to the nucleus where it binds TEAD transcription factors, promoting the expression of YAP-regulated genes. Remarkably, by transcriptomic RNA-sequencing of OM cells treated with FAKi and Gene Set Enrichment Analysis (GSEA) (Subramanian et al., 2005), Applicant found that FAKi treatment results in a significant downregulation of YAP-signature genes. Systematic dissection of the underlying mechanisms led us to uncover that FAK promotes YAP activity through direct tyrosine phosphorylation of YAP (Y357) concomitant with the release of inhibitory core Hippo signaling on YAP by tyrosine phosphorylation of MOB1 (pY26) and the consequent inhibition of LATS. Our studies provided a novel direct link between Gαq-FAK driven tyrosine phosphorylation networks and YAP activation[1].

FAK is a Druggable Signaling Target Downstream from the GNAQ Oncogene.

Several highly selective small molecule FAKi have been generated and are currently being evaluated in the clinic (Sulzmaier, 2014). Among them, PF-562271 is a classical FAKi (Lee, 2015) and VS-4718 is a new generation orally-bioavailable FAKi (Sulzmaier, 2014). Applicant confirmed that a) FAK knock down (KD) or CRISPR/Cas9 genome editing reduces UM cell proliferation and tumorigenesis, b) treatment with FAKi had limited effects in SKCM harboring BRAF oncogenes, but inhibited FAK (and YAP, see below), and reduced cell proliferation and tumor growth in vivo in UM (Feng et al., 2019), thereby establishing FAK as a druggable target in OM. Ultimately, based on our recent findings (Feng et al., 2019; Vaque et al., 2013; Feng et al., 2014a and 2014b) and without wishing to be bound by the theory, Applicant hypothesize that the non-receptor tyrosine kinase FAK is an integral part of the non-canonical Gαq-signaling pathway initiated through TRIO and Rho GTPases, and that in turn FAK inhibition or restraining its downstream regulated pathways may represent a precision therapeutic approach for mUM, alone or as part of novel signal transduction-based precision co-targeting strategies Exploiting GNAQ-Synthetic Lethal and Gene Interaction Networks to Expose Systems Vulnerabilities Resulting in OM Cell Death as a Precision Therapeutic Approach to Treat mUM.

A major drawback of the use of targeted therapies is that the prolonged inhibition of key signalling hubs, such as EGFR, PI3K, BRAF, and mTOR, often leads to the activation of an intricate network of feedback loops, which may initiate compensatory bypass mechanisms overcoming the growth-suppressive activity of targeted therapies (Wang et al., 2014; Lui et al., 2013; Quesnelle, 2011; Stabile et al., 2011; Yamaguchi et al., 2016). As such, combinatorial inhibition of oncogene-effector and feedback pathways is a promising cancer treatment strategy (Anderson et al., 2017). However, the Gαq-regulated pathways that when overactive, can render FAKi ineffective, as well as what feedback mechanisms should be targeted to optimize therapeutic responses to FAKi are still unknown. In addition, signaling inhibitors typically cause cytostatic rather than cytotoxic inhibition of tumor growth. In the absence of tumor shrinkage, tumor persistence allows the near-certain onset of resistance mechanisms and tumor escape.

Novel Gαq-FAK Regulated Signaling and Transcriptional Networks.

As part of an effort to identify additional novel Gαq-FAK regulated pathway contributing to the therapeutic response and/or drug resistance to FAKi, Applicant performed RNA sequencing, and Gene Set Enrichment Analysis (GSEA) (Subramanian et al., 2005)) to characterize the transcriptional effects of inhibiting Gαq and FAK at the pathway level using over 10,000 gene sets from the MSigDB (Molecular Signatures Database). As an example, 20 of these oncogenic signature gene sets were significantly repressed by FAKi in UM cells, including the downregulation of gene sets stimulated by KRAS, EGFR, PTEN KD (FIG. 5A), and YAP-signature genes (Zhao et al., 2008), the latter as Applicant recently described (Feng et al., 2019). Considering the shared pathways among the other top hits and without to be bound by the theory, Applicant hypothesize that FAK may act downstream from Gαq in the signaling pathway linking this G protein to ERK and/or PI3K-AKT-mTOR activation, which has not been previously reported.

Signaling Pathway-Activating Mutant Screen.

Figure 14A:
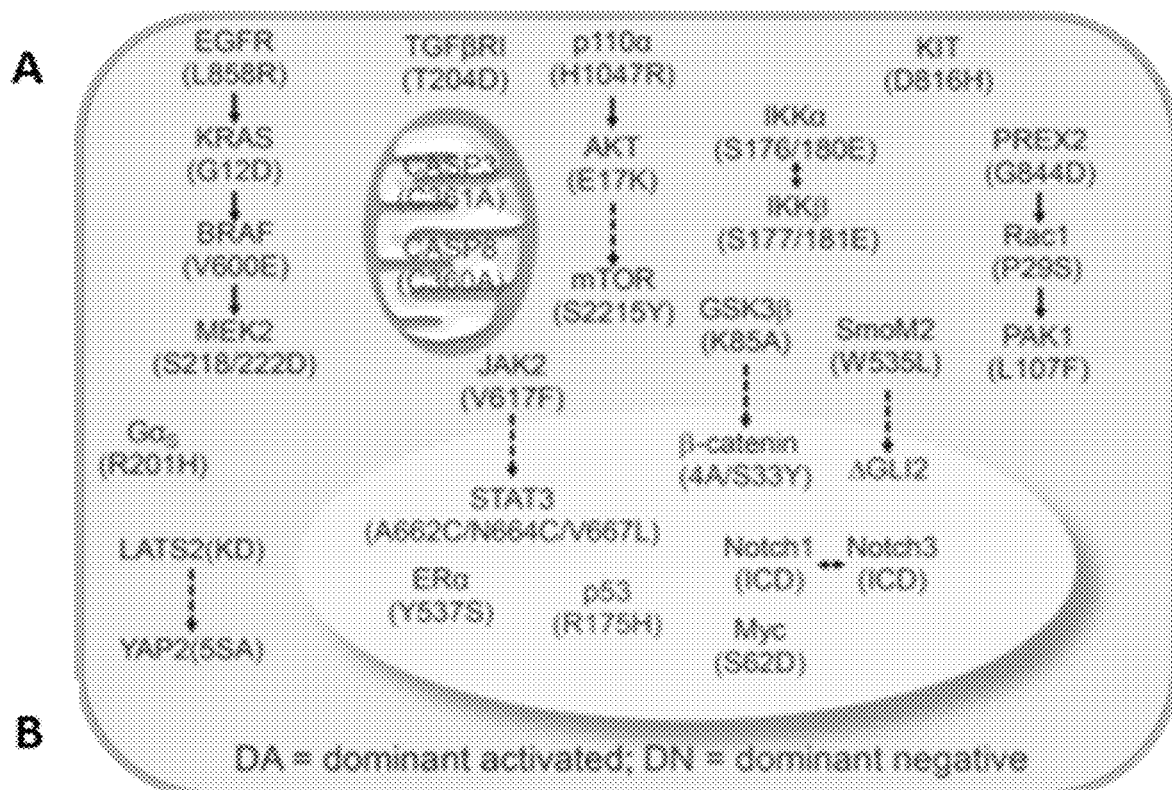
FIGS. 14A and 14B provide CSTK analysis of mechanisms rescuing from FAKi growth inhibition.
Figure 14B:
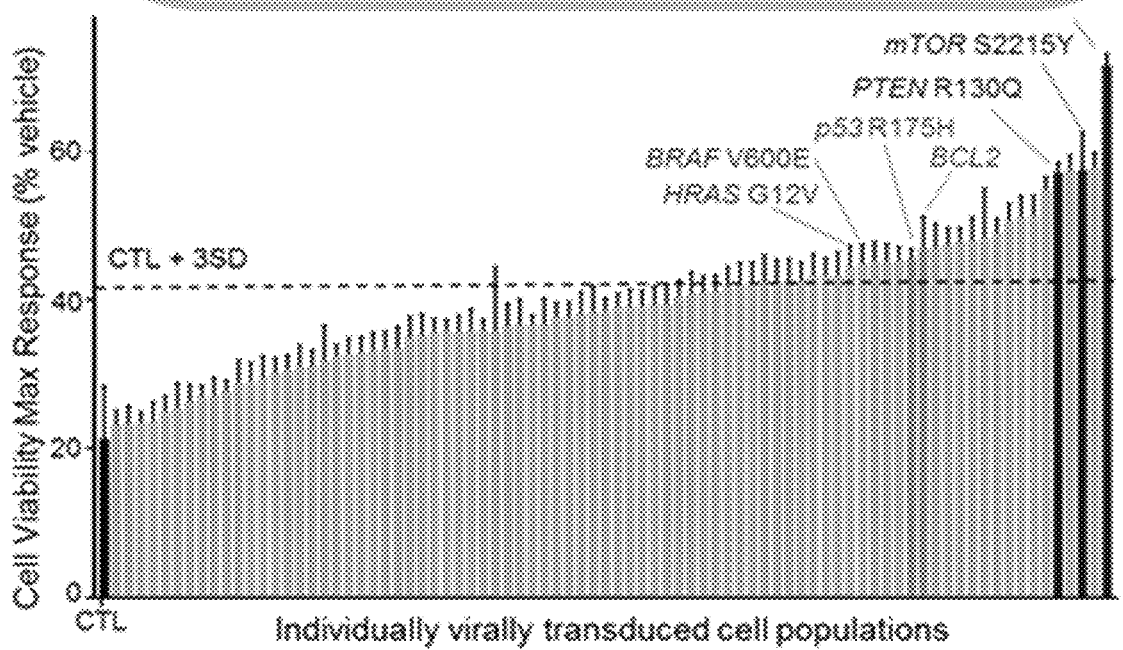
Figure 15:
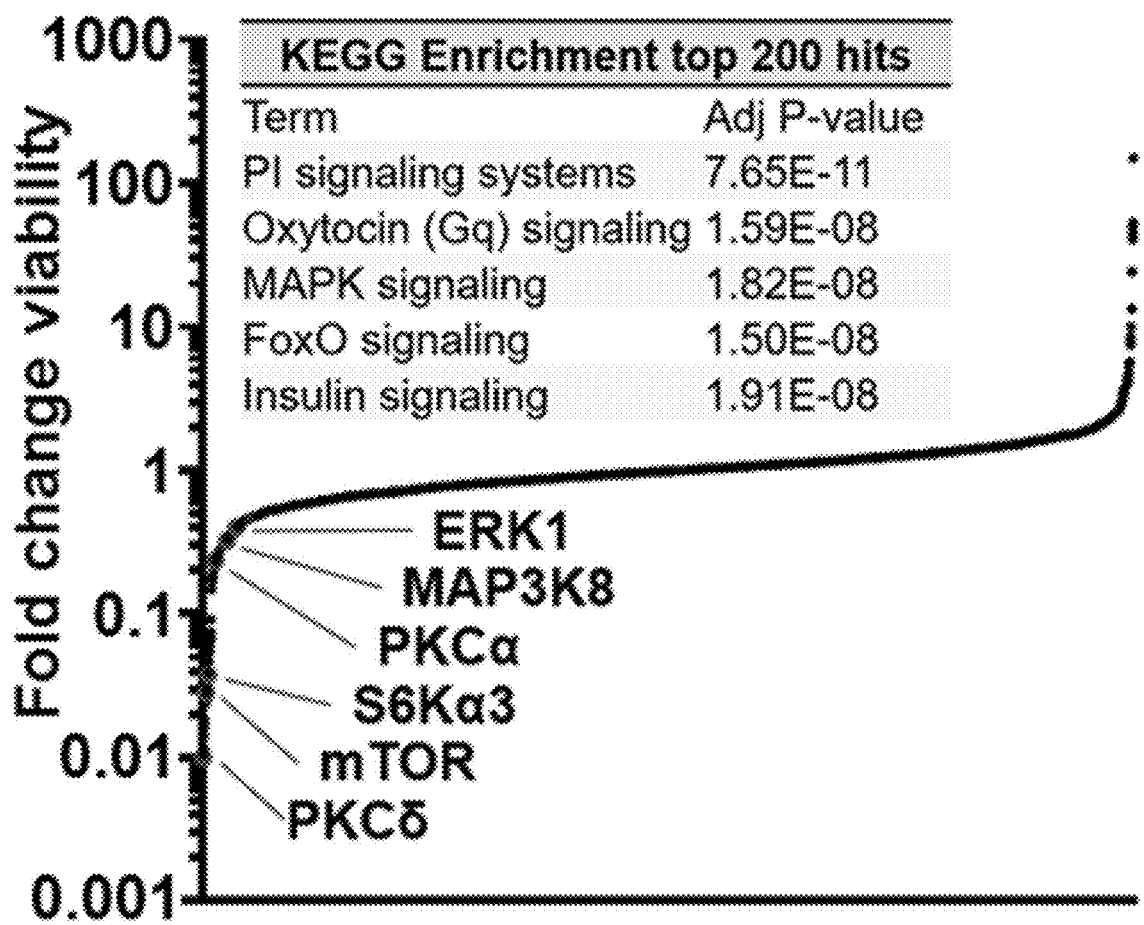
FIG. 15 shows results of kinome-wide CRISPR screen for synthetic lethal interactors of FAKi. OM cells expressing Cas9 were infected with the Brunello Human Kinome CRISPR sgRNA KO library at an MOI of 0.3. After selection, cells were treated with vehicle or 0.5 μM VS-4718 (FAKi). Data are represented as fold change viability in FAKi-treated cells compared to control. Significant hits represent synthetic lethal genes with FAKi treatment. (inset) Pathway analysis of top 200 synthetic lethal genes with FAKi using KEGG enrichment.

Both intrinsic and acquired resistance severely limit the depth and duration of clinical response to single-agent therapies. Further, the means by which tumor cells can acquire resistance to a given targeted therapy have been proven to be challenging to predict. In order to systematically interrogate cell-context specific mechanisms of resistance to antitumor agents, Dr. Wood recently developed a unique approach to explore the biological impact of activating the signaling pathways most frequently implicated in cancer (e.g., ERK, Ras, PI3K, STAT3, Wnt, Notch, TGFβ, Hippo, MAPKs, oncogenic transcription factors, among others). His team generated barcoded, lentiviral cDNA constructs representing key nodes in each pathway that when overexpressed, render each pathway constitutively active, in total, comprising 100 unique mutants (Martz et al., 2014) (FIG. 14). These constructs, collectively referred to as "The Cancer Signaling Toolkit" (CSTK), have been designed and used to rapidly profile and discover drug resistance pathways (Martz et al., 2014). Taking advantage of this approach, Applicant performed a genetic screen using the CSTK to identify signaling genes that can rescue the growth suppressive activity of FAKi in UM. Applicant found that PI3K/AKT/mTOR pathway activating genes were among the top hits rescuing from FAKi (FIG. 14), which is remarkably aligned with our FAK GSEA (above) suggesting a central role for PI3K pathway regulation by GNAQ through FAK in UM. Similarly, Applicant found that many rescuing viruses activate directly the ERK/MAPK pathway (e.g., HRAS, BRAF) or act upstream of this signaling route (e.g., HGF, FGFR3), suggesting that compensatory ERK reactivation can result in FAKi resistance (see below, also for additional rescuing genes) (FIG. 14).

Kinome-Wide CRISPR/Cas9 Screens Identify Synthetic Lethal Targets for FAKi.

Applicant performed a kinome-wide Cas9/CRISPR-based screen to identify molecular events rescuing (resistance mechanisms) from FAK inhibition or increasing the response to FAKi (sensitizing mechanisms) that are synthetic lethal for FAKi. As the kinome has been the target of a majority of drug-discovery efforts, Applicant envisioned that the identification of kinases whose activity are essential for OM survival in the context of FAKi will facilitate the discovery of therapeutic targets that are readily translatable to clinical efforts. Applicant have developed a sgRNA reduction algorithm that reduces the readout of multiple silencing elements (sgDNA), from many to one representative readout for gene symbol (e.g., the RIGER (Ebert et al., 2008) or ATARiS (Shao et al., 2013) algorithms that Applicant co-developed at the Broad Institute). The statistical significance of each cell viability profile is estimated using an empirical permutation test based on computing the information coefficient (IC) scores against a randomized phenotype. Using these methods and a variant of the Gene Set Enrichment Analysis (GSEA) methodology, Applicant have investigated if the top a) synthetic lethal, b) rescue and c) sensitizing hits are enriched in specific biological processes or signaling pathways. Remarkably, our analysis of synthetic lethal interactors of FAKi revealed a significant enrichment of Gq-PLC and MAPK signaling components, aligned with the results of our CSTK screen.

Co-Targeting the Gαq-FAK Signaling Circuitry and the MEK-ERK Pathway in GNAQ-Driven Malignancies.

Figures 16A, 16B, 16C:
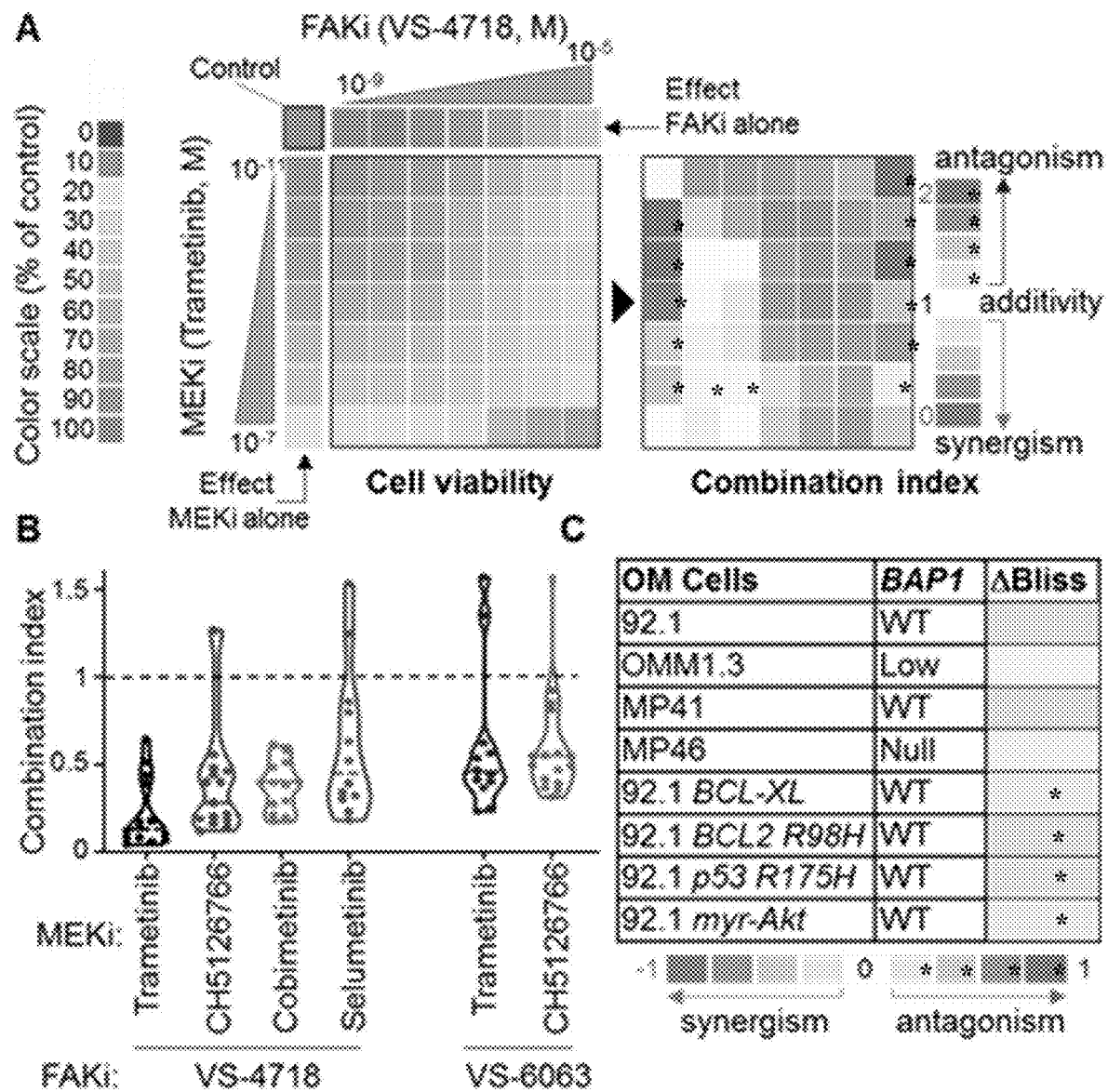
FIGS. 16A-16C show synergy between FAKi and MEKi in OM and mOM cells.

Remarkably, both CRISPR/Cas9 sgRNA and signaling activation (CSTK) screens converged to reveal that co-targeting FAK and the MEK-ERK pathway would be a promising combination for treatment of OM, and thus Applicant are focused on this specific potential synthetic lethal interaction. Applicant performed detailed combinatorial analysis achieving ERK pathway inhibition by a clinical MEK inhibitor, trametinib, combined with FAKi (VS-4718) at a series of dilutions of drug combinations. Drug combinations scored as synergistic (i. e., > than additive) are identified by using the most widely used methodologies: the Chou-Talalay combination index (CI) (Chou, 2010; Chou, 1984; and Chou, 2006) and the Bliss independence score (ΔBliss) (Chou, 2010; Chou, 2006; Berenbaum, 1989; Greco, 1995; and Geary, 2013) as Applicant recently described (Yamaguchi et al., 216). Co-inhibition of FAK and MEK/ERK showed a remarkable synergistic growth inhibitory effect in OM cells (FIG. 5). Applicant also performed a class analysis of MEK-ERK pathway inhibition by multiple approved MEKis, combined with FAKi, all of which showed remarkable synergistic activity supporting a general drug class interaction (FIG. 16). Additionally, the novel RAF/MEK inhibitor CH5126766 (Wada et al., 2014; Knauf et al., 2018) also showed synergistic anti-proliferative effects with VS-4718 and its clinically relevant VS-6063 (known as defactinib), similar to trametinib. This provides a strong rationale for focusing on FAK/MEK-ERK therapeutic interaction for our proposed initial co-targeting studies. Applicant observed similar synergistic profiles in BAP1 low or null cell lines supporting the possibility that FAKi/MEKi combination are active in mUM.

The Therapeutic Potential of Co-Targeting FAK and MEK-ERK in UM and mUM In Vivo.

Figures 17A, 17B:
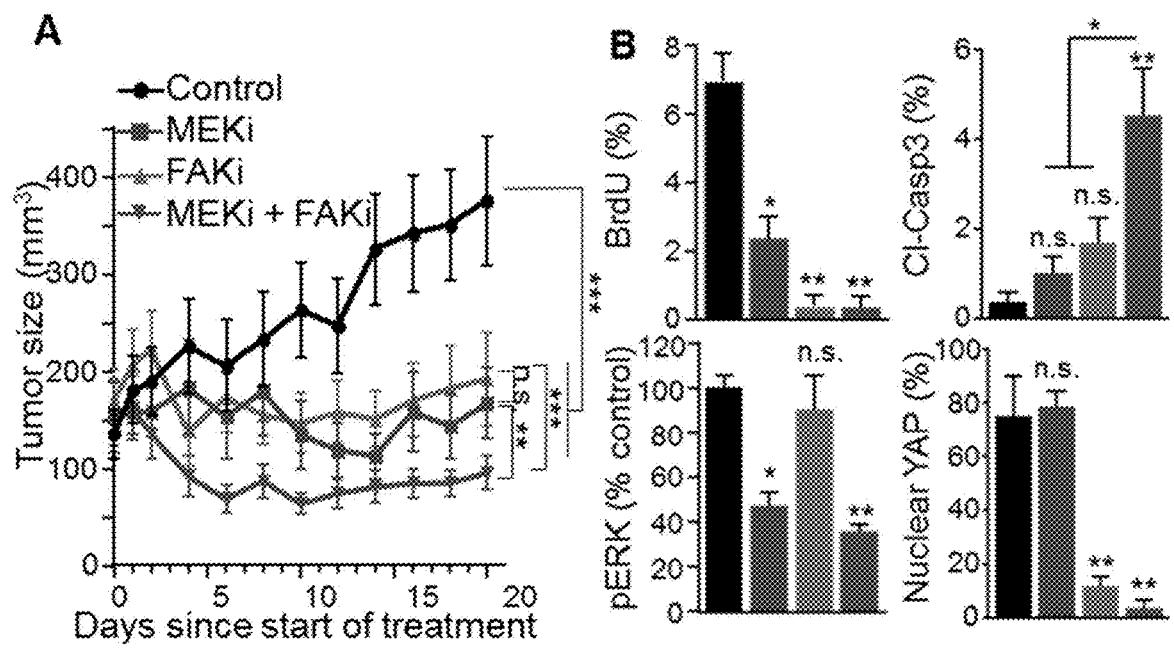
FIGS. 17A and 17B show potent antitumoral and cytotoxic effects of FAKi/MEKi combination in OM xenografts.
Figure 18A:
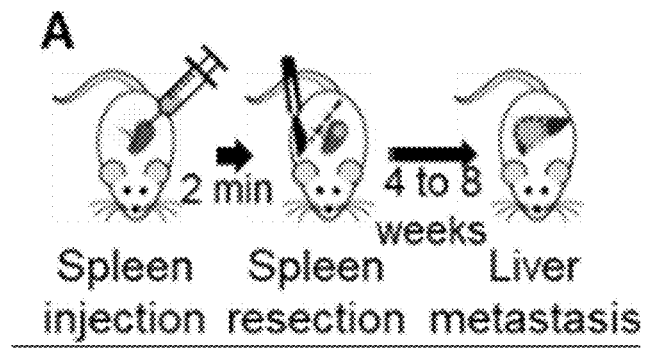
FIGS. 18A to 18G show potent antitumoral activity of FAKi/MEKi co-treatment in mOM models.
Figures 18B, 18C, 18D:
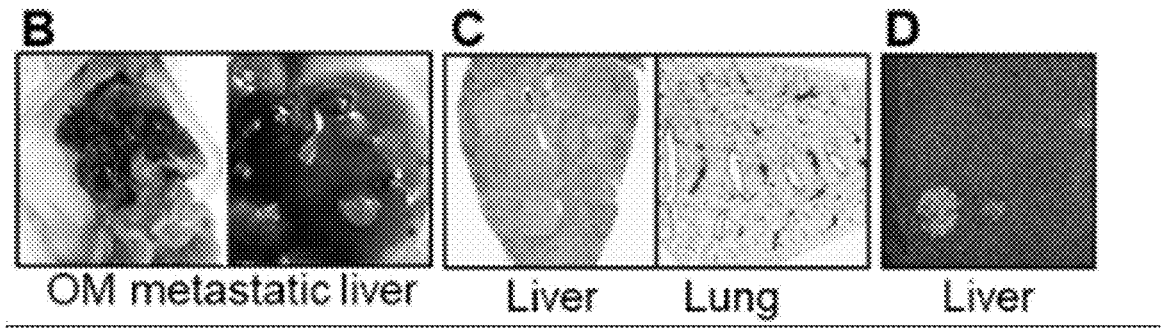
Figure 18E:
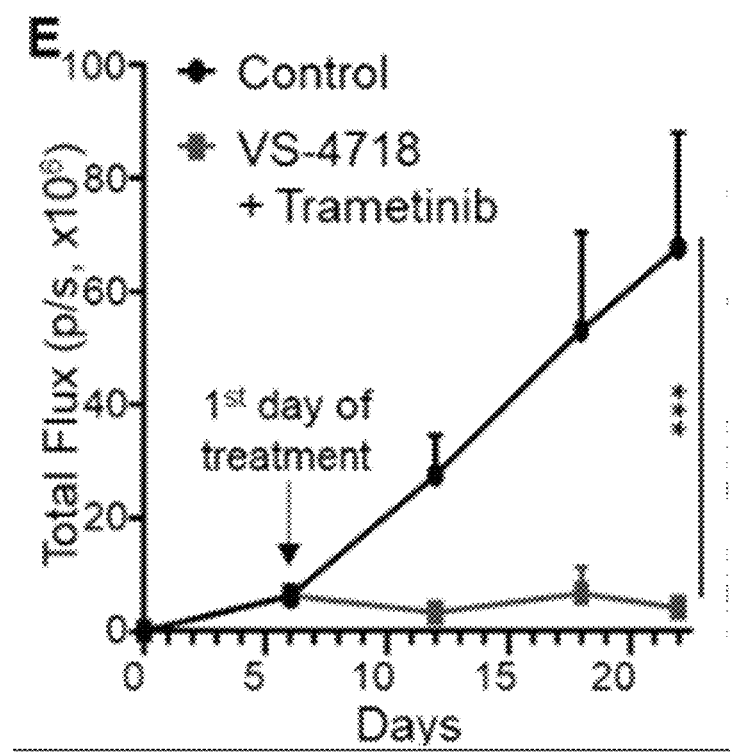
Figure 18F:
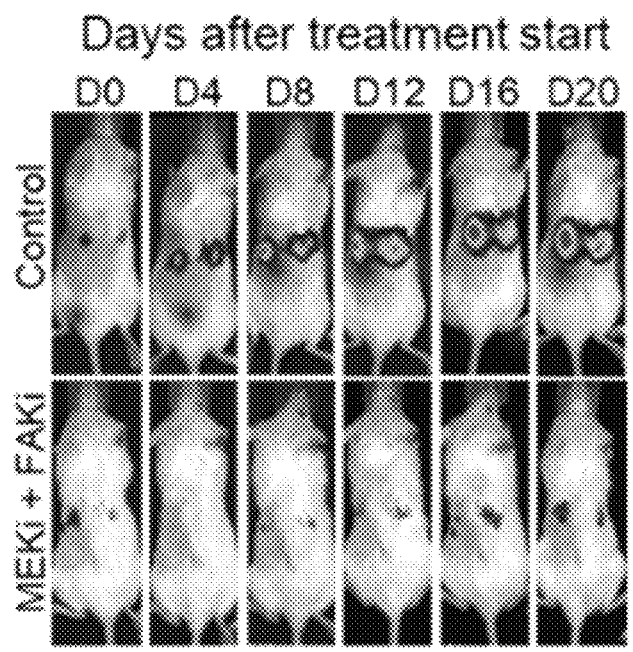
Figure 18G:
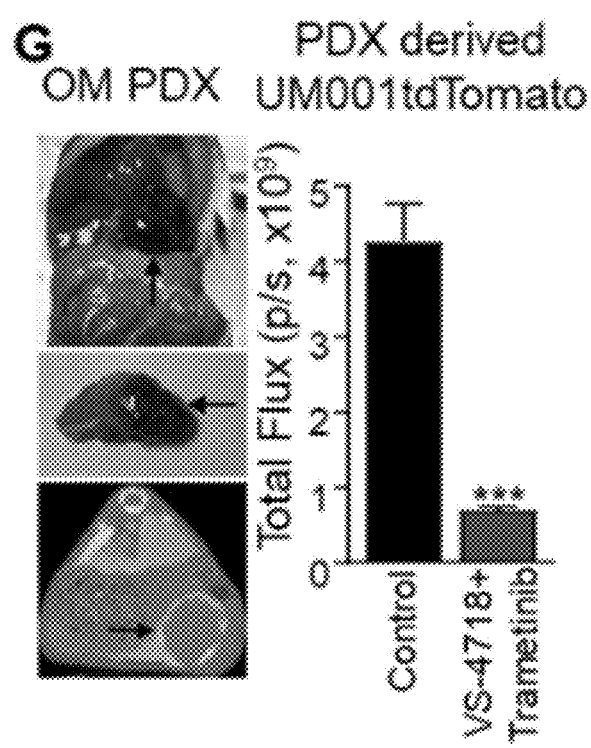

Applicant have now demonstrated therapeutic potential of co-targeting FAK and the MEK-ERK pathway in OM models in vivo (FIG. 17), as well as in recently developed UM metastasis models and mUM PDX models (FIG. 18). Specifically, Applicant have obtained evidence that FAKi (VS-4718) and MEKi (trametinib) as single agents present a cytostatic profile in OM xenografts while they are cytotoxic (increased cl-Casp3) in the combined treatment (FIG. 17). Similarly, Applicant found that VS-4718 and trametinib combination recapitulate our xenograft data showing a strong inhibition of metastatic progression (FIG. 18).

New Metastatic OM Models.

The major challenge in designing a treatment strategy for OM hepatic metastasis is the lack of suitable animal models. Applicant have now developed a) an orthotopic mouse model for human UM hepatic metastases, and b) established and characterized multiple mUM PDX mouse models. a) Splenic-injection/hematogenous dissemination model: Applicant have developed a preclinical murine UM tumor model of hepatic metastases via splenic injection (Soares et al., 2014) of UM cells stably expressing GFP-luciferase (Luc), in nonobese diabetic/severe combined immunodeficiency (NOD-SCID) gamma (NSG) mice, which enables monitoring the metastatic cancer burden in vivo using the Lumina Imaging System (IVIS). Ex vivo imaging of multiples organs post splenic implantation show the migration of the cells to the liver, lung, and other organs, but that few cluster of UM cells remain viable only in the liver after 24 h (not shown). Analysis of disease progression over time showed that implanted mice display both macroscopic and microscopic hepatic metastases (FIG. 18). Remarkably, the combination treatment of VS-4718 and trametinib nearly abolished metastatic progression of OM (FIG. 18). Indeed, the combination of FAK and MEK/ERK blockade elicited a remarkable beneficial effect.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Additional information regarding the claimed embodiments is provided in the Appendix attached hereto.

Other aspects are set forth within the following claims.

REFERENCES

1) Anderson, G. R. et al. A Landscape of Therapeutic Cooperativity in KRAS Mutant Cancers Reveals Principles for Controlling Tumor Evolution. Cell Rep 20, 999-1015 (2017).
2) Armbruster, B. N., Li, X., Pausch, M. H., Herlitze, S., and Roth, B. L. (2007). Evolving the lock to fit the key to create a family of G protein-coupled receptors potently activated by an inert ligand. Proc Natl Acad Sci USA 104, 5163-5168.
3) Arnold, J. J., Blinder, K. J., Bressler, N. M., Bressler, S. B., Burdan, A., Haynes, L., Lim, J. I., Miller, J. W., Potter, M. J., Reaves, A., et al. (2004). Acute severe visual acuity decrease after photodynamic therapy with verteporfin: case reports from randomized clinical trials-TAP and VIP report no. 3. Am J Ophthalmol 137, 683-696.
4) Ashworth, A., Lord, C. J. & Reis, J. S. Genetic Interactions in Cancer Progression and Treatment. Cell 145, 30-38 (2011).
5) Azab, M., Benchaboune, M., Blinder, K. J., Bressler, N. M., Bressler, S. B., Gragoudas, E. S., Fish, G. E., Hao, Y., Haynes, L., Lim, J. I., et al. (2004). Verteporfin therapy of subfoveal choroidal neovascularization in age-related macular degeneration: meta-analysis of 2-year safety results in three randomized clinical trials: Treatment Of Age-Related Macular Degeneration With Photodynamic Therapy and Verteporfin In Photodynamic Therapy Study Report no. 4. Retina 24, 1-12.
6) Barbazetto, I. A., Lee, T. C., Rollins, I. S., Chang, S., and Abramson, D. H. (2003). Treatment of choroidal melanoma using photodynamic therapy. Am J Ophthalmol 135, 898-899.
7) Barretina, J., Caponigro, G., Stransky, N., Venkatesan, K., Margolin, A. A., Kim, S., Wilson, C. J., Lehar, J., Kryukov, G. V., Sonkin, D., et al. (2012). The Cancer Cell Line Encyclopedia enables predictive modelling of anticancer drug sensitivity. Nature 483, 603-607.
8) Basu, A. et al. An Interactive Resource to Identify Cancer Genetic and Lineage Dependencies Targeted by Small Molecules. Cell 154, 1151-1161 (2013).
9) Basu, A., Bodycombe, N. E., Cheah, J. H., Price, E. V., Liu, K., Schaefer, G. I., Ebright, R. Y., Stewart, M. L., Ito, D., Wang, S., et al. (2013). An Interactive Resource to Identify Cancer Genetic and Lineage Dependencies Targeted by Small Molecules. Cell 154, 1151-1161.
10) Berenbaum, M. C. What is synergy? Pharmacol Rev 41, 93-141 (1989).
11) Bhatt, M., Shah, S., and Shivprakash (2010). Development of a high-throughput method for the determination of ethosuximide in human plasma by liquid chromatography mass spectrometry. J Chromatogr B Analyt Technol Biomed Life Sci 878, 1605-1610.
12) Brough, R., Frankum, J. R., Costa-Cabral, S., Lord, C. J. & Ashworth, A. Searching for synthetic lethality in cancer. Curr Opin Genet Dev 21, 34-41 (2011).
13) Cancer Genome Atlas Research, N., Weinstein, J. N., Collisson, E. A., Mills, G. B., Shaw, K. R., Ozenberger, B. A., Ellrott, K., Shmulevich, I., Sander, C., and Stuart, J. M. (2013). The Cancer Genome Atlas Pan-Cancer analysis project. Nat Genet 45, 1113-1120.
14) Carvajal, R. D. et al. Effect of selumetinib vs chemotherapy on progression-free survival in uveal melanoma: a randomized clinical trial. Jama 311, 2397-2405 (2014).
15) Carvajal, R. D. et al. Selumetinib in Combination With Dacarbazine in Patients With Metastatic Uveal Melanoma: A Phase III, Multicenter, Randomized Trial (SUMIT). J Clin Oncol 36, 1232-1239 (2018).
16) Carvajal, R. D., Piperno-Neumann, S., Kapiteijn, E., Chapman, P. B., Frank, S., Joshua, A. M., Piulats, J. M., Wolter, P., Cocquyt, V., Chmielowski, B., et al. (2018). Selumetinib in Combination With Dacarbazine in Patients With Metastatic Uveal Melanoma: A Phase III, Multicenter, Randomized Trial (SUMIT). J Clin Oncol 36, 1232-1239.
17) Carvajal, R. D., Sosman, J. A., Quevedo, J. F., Milhem, M. M., Joshua, A. M., Kudchadkar, R. R., Linette, G. P., Gajewski, T. F., Lutzky, J., Lawson, D. H., et al. (2014). Effect of selumetinib vs chemotherapy on progression-free survival in uveal melanoma: a randomized clinical trial. Jama 311, 2397-2405.
18) Chen, X., Wu, Q., Depeille, P., Chen, P., Thornton, S., Kalirai, H., Coupland, S. E., Roose, J. P., and Bastian, B. C. (2017). RasGRP3 Mediates MAPK Pathway Activation in GNAQ Mutant Uveal Melanoma. Cancer Cell 31, 685-696 e686.
19) Cheung, H. W. et al. Systematic investigation of genetic vulnerabilities across cancer cell lines reveals lineage-specific dependencies in ovarian cancer. Proc Natl Acad Sci USA 108, 12372-12377 (2011).
20) Cheung, H. W., Cowley, G. S., Weir, B. A., Boehm, J. S., Rusin, S., Scott, J. A., East, A., Ali, L. D., Lizotte, P. H., Wong, T. C., et al. (2011). Systematic investigation of genetic vulnerabilities across cancer cell lines reveals lineage-specific dependencies in ovarian cancer. Proceedings of the National Academy of Sciences of the United States of America 108, 12372-12377.
21) Chikumi, H., Fukuhara, S., and Gutkind, J. S. (2002). Regulation of G protein-linked guanine nucleotide exchange factors for Rho, PDZ-RhoGEF, and LARG by tyrosine phosphorylation: evidence of a role for focal adhesion kinase. J Biol Chem 277, 12463-12473.
22) Chou, T. C. & Talalay, P. Quantitative analysis of dose-effect relationships: the combined effects of multiple drugs or enzyme inhibitors. Adv Enzyme Regul 22, 27-55 (1984).
23) Chou, T. C. Drug combination studies and their synergy quantification using the Chou-Talalay method. Cancer Res 70, 440-446 (2010).
24) Chou, T. C. Theoretical basis, experimental design, and computerized simulation of synergism and antagonism in drug combination studies. Pharmacol Rev 58, 621-681 (2006).
25) Cowley, G. S. et al. Parallel genome-scale loss of function screens in 216 cancer cell lines for the identification of context-specific genetic dependencies. Sci Data 1, 140035 (2014).

26) Cowley, G. S., Weir, B. A., Vazquez, F., Tamayo, P., Scott, J. A., Rusin, S., East-Seletsky, A., Ali, L. D., Gerath, W. F., Pantel, S. E., et al. (2014). Parallel genome-scale loss of function screens in 216 cancer cell lines for the identification of context-specific genetic dependencies. Sci Data 1, 140035.
27) Dorsam, R. T. & Gutkind, J. S. G-protein-coupled receptors and cancer. Nat Rev Cancer 7, 79-94 (2007).
28) Dorsam, R. T., and Gutkind, J. S. (2007). G-protein-coupled receptors and cancer. Nat Rev Cancer 7, 79-94.
29) Ebert, B. L. et al. Identification of RPS14 as a 5q– syndrome gene by RNA interference screen. Nature 451, 335-339 (2008).
30) Falchook, G. S. et al. Activity of the oral MEK inhibitor trametinib in patients with advanced melanoma: a phase 1 dose-escalation trial. Lancet Oncol 13, 782-789 (2012).
31) Feng, X. et al. A Platform of Synthetic Lethal Gene Interaction Networks Reveals that the GNAQ Uveal Melanoma Oncogene Controls the Hippo Pathway through FAK. Cancer Cell 35, 457-472 e455 (2019).
32) Feng, X. et al. Hippo-independent activation of YAP by the GNAQ uveal melanoma oncogene through a trio-regulated rho GTPase signaling circuitry. Cancer Cell 25, 831-845 (2014 and 2014b).
33) Feng, X., Chen, Q., and Gutkind, J. S. (2014a). Onco-targeting G proteins: The Hippo in the room. Oncotarget 5, 10997-10999.
34) Field, M. G. & Harbour, J. W. Recent developments in prognostic and predictive testing in uveal melanoma. Curr Opin Ophthalmol 25, 234-239 (2014).
35) Friedman, A. A., Amzallag, A., Pruteanu-Malinici, I., Baniya, S., Cooper, Z. A., Piris, A., Hargreaves, L., Igras, V., Frederick, D. T., Lawrence, D. P., et al. (2015). Landscape of Targeted Anti-Cancer Drug Synergies in Melanoma Identifies a Novel BRAF508 VEGFR/PDGFR Combination Treatment. PLoS One 10, e0140310.
36) Gao, J. et al. Integrative analysis of complex cancer genomics and clinical profiles using the cBioPortal. Sci Signal 6, pl1 (2013).
37) Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortal. Sci Signal 6, pl1.
38) Garnett, M. J., Edelman, E. J., Heidorn, S. J., Greenman, C. D., Dastur, A., Lau, K. W., Greninger, P., Thompson, I. R., Luo, X., Soares, J., et al. (2012). Systematic identification of genomic markers of drug sensitivity in cancer cells. Nature 483, 570-U587.
39) Geary, N. Understanding synergy. Am J Physiol Endocrinol Metab 304, E237-253 (2013).
40) Greco, W. R., Bravo, G. & Parsons, J. C. The search for synergy: a critical review from a response surface perspective. Pharmacol Rev 47, 331-385 (1995).
41) Griner, E. M., and Kazanietz, M. G. (2007). Protein kinase C and other diacylglycerol effectors in cancer. Nat Rev Cancer 7, 281-294.
42) Gutkind, J. S. & Robbins, K. C. Activation of transforming G protein-coupled receptors induces rapid tyrosine phosphorylation of cellular proteins, including p125FAK and the p130 v-src substrate. Biochem Biophys Res Commun 188, 155-161 (1992).
43) Gutkind, J. S., and Robbins, K. C. (1992). Activation of transforming G protein-coupled receptors induces rapid tyrosine phosphorylation of cellular proteins, including p125FAK and the p130 v-src substrate. Biochem Biophys Res Commun 188, 155-161.
44) Gutkind, J. S., Novotny, E. A., Brann, M. R., and Robbins, K. C. (1991). Muscarinic acetylcholine receptor subtypes as agonist-dependent oncogenes. Proc Natl Acad Sci USA 88, 4703-4707.
45) Harbour, J. W. et al. Frequent mutation of BAP1 in metastasizing uveal melanomas. Science 330, 1410-1413 (2010).
46) Hartwell, L. H., Szankasi, P., Roberts, C. J., Murray, A. W. & Friend, S. H. Integrating genetic approaches into the discovery of anticancer drugs. Science 278, 1064-1068 (1997).
47) Helgadottir, H. & Mom, V. The genetics of uveal melanoma: current insights, in Appl Clin Genet, Vol. 9 147-155 (2016).
48) Howe, A. K. (2011). Cross-talk between calcium and protein kinase A in the regulation of cell migration. Current opinion in cell biology 23, 554-561.
49) Hu, J. K., Du, W., Shelton, S. J., Oldham, M. C., DiPersio, C. M., and Klein, O. D. (2017). An FAK-YAP-mTOR Signaling Axis Regulates Stem Cell-Based Tissue Renewal in Mice. Cell Stem Cell 21, 91-106 e106.
50) Hubbard, K. B. & Hepler, J. R. Cell signalling diversity of the Gqalpha family of heterotrimeric G proteins. Cell Signal 18, 135-150 (2006).
51) Hubbard, K. B., and Hepler, J. R. (2006). Cell signalling diversity of the Gqalpha family of heterotrimeric G proteins. Cell Signal 18, 135-150.
52) Igishi, T., Fukuhara, S., Patel, V., Katz, B. Z., Yamada, K. M., and Gutkind, J. S. (1999). Divergent signaling pathways link focal adhesion kinase to mitogen-activated protein kinase cascades. Evidence for a role of paxillin in c-Jun NH(2)-terminal kinase activation. J Biol Chem 274, 30738-30746.
53) Ikeda, F., Terajima, H., Shimahara, Y., Kondo, T., and Yamaoka, Y. (2003). Reduction of hepatic ischemia/reperfusion-induced injury by a specific ROCK/Rho kinase inhibitor Y-27632. J Surg Res 109, 155-160.
54) Iorio, F. et al. A Landscape of Pharmacogenomic Interactions in Cancer. Cell 166, 740-754 (2016).
55) Iorio, F., Knijnenburg, T. A., Vis, D. J., Bignell, G. R., Menden, M. P., Schubert, M., Aben, N., Goncalves, E., Barthorpe, S., Lightfoot, H., et al. (2016). A Landscape of Pharmacogenomic Interactions in Cancer. Cell 166, 740-754.
56) Jerby-Arnon, L. et al. Predicting cancer-specific vulnerability via data-driven detection of synthetic lethality. Cell 158, 1199-1209 (2014).
57) Jiang, H. et al. Targeting focal adhesion kinase renders pancreatic cancers responsive to checkpoint immunotherapy. Nat Med 22, 851-860 (2016).
58) Julius, D., and Nathans, J. (2012). Signaling by sensory receptors. Cold Spring Harbor perspectives in biology 4, a005991.
59) Kaelin, W. G. The concept of synthetic lethality in the context of anticancer therapy. Nature Reviews Cancer 5, 689-698 (2005).
60) Kalinec, G., Nazarali, A. J., Hermouet, S., Xu, N. & Gutkind, J. S. Mutated alpha subunit of the Gq protein induces malignant transformation in NIH 3T3 cells. Mol Cell Biol 12, 4687-4693 (1992).
61) Kalinec, G., Nazarali, A. J., Hermouet, S., Xu, N., and Gutkind, J. S. (1992). Mutated alpha subunit of the Gq protein induces malignant transformation in NIH 3T3 cells. Mol Cell Biol 12, 4687-4693.
62) Knauf, J. A. et al. Hgf/Met activation mediates resistance to BRAF inhibition in murine anaplastic thyroid cancers. J Clin Invest 128, 4086-4097 (2018).

63) Kovacs, M., Toth, J., Hetenyi, C., Malnasi-Csizmadia, A., and Sellers, J. R. (2004). Mechanism of blebbistatin inhibition of myosin II. J Biol Chem 279, 35557-35563.
64) Lachowski, D., Cortes, E., Robinson, B., Rice, A., Rombouts, K., and Del Rio Hernandez, A. E. (2018). FAK controls the mechanical activation of YAP, a transcriptional regulator required for durotaxis. FASEB J 32, 1099-1107.
65) Law, V., Knox, C., Djoumbou, Y., Jewison, T., Guo, A. C., Liu, Y., Maciejewski, A., Arndt, D., Wilson, M., Neveu, V., et al. (2014). DrugBank 4.0: shedding new light on drug metabolism. Nucleic Acids Res 42, D1091-1097.
66) Lee, B. Y., Timpson, P., Horvath, L. G. & Daly, R. J. FAK signaling in human cancer as a target for therapeutics. Pharmacol Ther 146, 132-149 (2015).
67) Lee, J. S. et al. Harnessing synthetic lethality to predict the response to cancer treatment. Nat Commun 9, 2546 (2018).
68) Lee, J. S., Das, A., Jerby-Arnon, L., Arafeh, R., Auslander, N., Davidson, M., McGarry, L., James, D., Amzallag, A., Park, S. G., et al. (2018). Harnessing synthetic lethality to predict the response to cancer treatment. Nat Commun 9, 2546.
69) Li, P., Silvis, M. R., Honaker, Y., Lien, W. H., Arron, S. T., and Vasioukhin, V. (2016). alphaE557 catenin inhibits a Src-YAP1 oncogenic module that couples tyrosine kinases and the effector of Hippo signaling pathway. Genes Dev 30, 798-811.
70) Liberzon, A., Birger, C., Thorvaldsdottir, H., Ghandi, M., Mesirov, J. P., and Tamayo, P. (2015).
71) Lui, V. W. Y. et al. Frequent mutation of the PI3K pathway in head and neck cancer defines predictive biomarkers. Cancer Discovery (2013).
72) Luke, J. J. et al. Biology of advanced uveal melanoma and next steps for clinical therapeutics. Pigment Cell & Melanoma Research 28, 135-147 (2016).
73) Marcotte, R. et al. Essential gene profiles in breast, pancreatic, and ovarian cancer cells. Cancer Discov 2, 172-189 (2012).
74) Marcotte, R. et al. Functional Genomic Landscape of Human Breast Cancer Drivers, Vulnerabilities, and Resistance. Cell 164, 293-309 (2016).
75) Marcotte, R., Brown, K. R., Suarez, F., Sayad, A., Karamboulas, K., Krzyzanowski, P. M., Sircoulomb, F., Medrano, M., Fedyshyn, Y., Koh, J. L., et al. (2012). Essential gene profiles in breast, pancreatic, and ovarian cancer cells. Cancer Discov 2, 172-189.
76) Marcotte, R., Sayad, A., Brown, K. R., Sanchez-Garcia, F., Reimand, J., Haider, M., Virtanen, C., Bradner, J. E., Bader, G. D., Mills, G. B., et al. (2016). Functional Genomic Landscape of Human Breast Cancer Drivers, Vulnerabilities, and Resistance. Cell 164, 293-309.
77) Marinissen, M. J., Servitja, J. M., Offermanns, S., Simon, M. I., and Gutkind, J. S. (2003). Thrombin protease-activated receptor-1 signals through Gq- and G13-initiated MAPK cascades regulating c-Jun expression to induce cell transformation. J Biol Chem 278, 46814-46825.
78) Martin, D., Degese, M. S., Vitale-Cross, L., Iglesias-Bartolome, R., Valera, J. L. C., Wang, Z., Feng, X., Yeerna, H., Vadmal, V., Moroishi, T., et al. (2018). Assembly and activation of the Hippo signalome by FAT1 tumor suppressor. Nat Commun 9, 2372.
79) Martz, C. A. et al. Systematic identification of signaling pathways with potential to confer anticancer drug resistance. Sci Signal 7, ra121 (2014).
80) Meng, Z., Moroishi, T. & Guan, K. L. Mechanisms of Hippo pathway regulation. Genes Dev 30, 1-17 (2016).
81) Meng, Z., Moroishi, T., and Guan, K. L. (2016). Mechanisms of Hippo pathway regulation. Genes Dev 30, 1-17.
82) Moore, A. R., Ceraudo, E., Sher, J. J., Guan, Y., Shoushtari, A. N., Chang, M. T., Zhang, J. Q., Walczak, E. G., Kazmi, M. A., Taylor, B. S., et al. (2016). Recurrent activating mutations of G-protein-coupled receptor CYSLTR2 in uveal melanoma. Nature Genetics 48, 675-680.
83) Moroishi, T., Hansen, C. G., and Guan, K. L. (2015). The emerging roles of YAP and TAZ in cancer. Nature reviews Cancer 15, 73-79.
84) Narumiya, S., Ishizaki, T., and Uehata, M. (2000). Use and properties of ROCK-specific inhibitor Y-27632. Methods Enzymol 325, 273-284.
85) Newton, A. C. (2010). Protein kinase C: poised to signal. Am J Physiol Endocrinol Metab 298, E395-402.
86) O'Hayre, M., Degese, M. S. & Gutkind, J. S. Novel insights into G protein and G protein-coupled receptor signaling in cancer. Curr Opin Cell Biol 27, 126-135 (2014).
87) O'Hayre, M., Vazquez-Prado, J., Kufareva, I., Stawiski, E. W., Handel, T. M., Seshagiri, S., and Gutkind, J. S. (2013). The emerging mutational landscape of G proteins and G-protein-coupled receptors in cancer. Nature reviews Cancer 13, 412-424.
88) Pan, D. (2010). The hippo signaling pathway in development and cancer. Dev Cell 19, 491-505.
89) Prevarskaya, N., Skryma, R., and Shuba, Y. (2011). Calcium in tumour metastasis: new roles for known actors. Nature reviews Cancer 11, 609-618.
90) Quesnelle, K. M. & Grandis, J. R. Dual kinase inhibition of EGFR and HER2 overcomes resistance to cetuximab in a novel in vivo model of acquired cetuximab resistance. Clinical cancer research 17, 5935-5944 (2011).
91) Robertson, A. G. et al. Integrative Analysis Identifies Four Molecular and Clinical Subsets in Uveal Melanoma. Cancer Cell 32, 204-220 e215 (2017).
92) Robertson, A. G., Shih, J., Yau, C., Gibb, E. A., Oba, J., Mungall, K. L., Hess, J. M., Uzunangelov, V., Walter, V., Danilova, L., et al. (2017). Integrative Analysis Identifies Four Molecular and Clinical Subsets in Uveal Melanoma. Cancer Cell 32, 204-220 e215.
93) Rozengurt, E. (2007). Mitogenic signaling pathways induced by G protein-coupled receptors. J Cell Physiol 213, 589-602.
94) Rozengurt, E. Mitogenic signaling pathways induced by G protein-coupled receptors. J Cell Physiol 213, 589-602 (2007).
95) Sanchez-Fernandez, G. et al. Galphaq signalling: the new and the old. Cell Signal 26, 833-848 (2014).
96) Sassone-Corsi, P. (2012). The cyclic AMP pathway. Cold Spring Harbor perspectives in biology 4.
97) Schober, M. & Fuchs, E. Tumor-initiating stem cells of squamous cell carcinomas and their control by TGF-beta and integrin/focal adhesion kinase (FAK) signaling. Proc Natl Acad Sci USA 108, 10544-10549 (2011).
98) Schrage, R., Schmitz, A. L., Gaffal, E., Annala, S., Kehraus, S., Wenzel, D., Bullesbach, K. M., Bald, T., Inoue, A., Shinjo, Y., et al. (2015). The experimental power of FR900359 to study Gq-regulated biological processes. Nat Commun 6, 10156.
99) Shao, D. D. et al. ATARiS: computational quantification of gene suppression phenotypes from multisample RNAi screens. Genome Res 23, 665-678 (2013).

100) Shapiro, I. M. et al. Merlin deficiency predicts FAK inhibitor sensitivity: a synthetic lethal relationship. Sci Transl Med 6, 237ra268 (2014).
101) Singh, A. D., Turell, M. E. & Topham, A. K. Uveal melanoma: trends in incidence, treatment, and survival. Ophthalmology 118, 1881-1885 (2011).
102) Smrcka, A. V., Brown, J. H. & Holz, G. G. Role of phospholipase Cepsilon in physiological phosphoinositide signaling networks. Cell Signal 24, 1333-1343 (2012).
103) Soares, K. C. et al. A preclinical murine model of hepatic metastases. J Vis Exp, 51677 (2014).
104) Soucek, P., and Cihelkova, I. (2006). Photodynamic therapy with verteporfin in subfoveal amelanotic choroidal melanoma (A controlled case). Neuro endocrinology letters 27, 145-148.
105) Stabile, L. P. et al. c-Src activation mediates erlotinib resistance in head and neck cancer by stimulating c-Met. Clin Cancer Res 19, 380-392 (2013).
106) Subramanian, A. et al. Gene set enrichment analysis: a knowledge-based approach for interpreting genome-wide expression profiles. Proc Natl Acad Sci USA 102, 15545-15550 (2005).
107) Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.
108) Sulzmaier, F. J., Jean, C. & Schlaepfer, D. D. FAK in cancer: mechanistic findings and clinical applications. Nat Rev Cancer 14, 598-610 (2014).
109) Sulzmaier, F. J., Jean, C., and Schlaepfer, D. D. (2014). FAK in cancer: mechanistic findings and clinical applications. Nat Rev Cancer 14, 598-610.
110) Tancioni, I., Miller, N. L., Uryu, S., Lawson, C., Jean, C., Chen, X. L., Kleinschmidt, E. G., and Schlaepfer, D. D. (2015). FAK activity protects nucleostemin in facilitating breast cancer spheroid and tumor growth. Breast Cancer Res 17, 47.
111) Taniguchi, K., Wu, L. W., Grivennikov, S. I., de Jong, P. R., Lian, I., Yu, F. X., Wang, K., Ho, S. B., Boland, B. S., Chang, J. T., et al. (2015). A gp130-Src-YAP module links inflammation to epithelial regeneration. Nature 519, 57-62.
112) Teramoto, H., Malek, R. L., Behbahani, B., Castellone, M. D., Lee, N. H., and Gutkind, J. S. (2003). Identification of H-Ras, RhoA, Rac1 and Cdc42 responsive genes. Oncogene 22, 2689-2697.
113) The Molecular Signatures Database (MSigDB) hallmark gene set collection. Cell systems 1, 417-425.
114) Therneau, T. M., and Grambsch, P. M. (2000). Modeling survival data: extending the Cox model (New York: Springer).
115) Tsherniak, A., Vazquez, F., Montgomery, P. G., Weir, B. A., Kryukov, G., Cowley, G. S., Gill, S., Harrington, W. F., Pantel, S., Krill-Burger, J. M., et al. (2017). Defining a Cancer Dependency Map. Cell 170, 564-576 e516.
116) Van Raamsdonk, C. D. et al. Frequent somatic mutations of GNAQ in uveal melanoma and blue naevi. Nature 457, 599-602 (2009).
117) Van Raamsdonk, C. D., Bezrookove, V., Green, G., Bauer, J., Gaugler, L., O'Brien, J. M., Simpson, E. M., Barsh, G. S., and Bastian, B. C. (2009). Frequent somatic mutations of GNAQ in uveal melanoma and blue naevi. Nature 457, 599-602.
118) Van Raamsdonk, C. D., Griewank, K. G., Crosby, M. B., Garrido, M. C., Vemula, S., Wiesner, T., Obenauf, A. C., Wackernagel, W., Green, G., Bouvier, N., et al. (2010). Mutations in GNA11 in uveal melanoma. N Engl J Med 363, 2191-2199.
119) Vaque, J. P. et al. A genome-wide RNAi screen reveals a Trio-regulated Rho GTPase circuitry transducing mitogenic signals initiated by G protein-coupled receptors. Mol Cell 49, 94-108 (2013).
120) Vaque, J. P., Dorsam, R. T., Feng, X., Iglesias-Bartolome, R., Forsthoefel, D. J., Chen, Q., Debant, A., Seeger, M. A., Ksander, B. R., Teramoto, H., et al. (2013). A genome-wide RNAi screen reveals a Trio-regulated Rho GTPase circuitry transducing mitogenic signals initiated by G-protein-coupled receptors. Mol Cell 49, 94-108.
121) Wada, M., Horinaka, M., Yamazaki, T., Katoh, N. & Sakai, T. The dual RAF/MEK inhibitor CH5126766/RO5126766 may be a potential therapy for RAS-mutated tumor cells. PLoS One 9, e113217 (2014).
122) Wang, Z. et al. mTor co-targeting in cetuximab resistance in head and neck cancers harboring PIK3CA and RAS mutations. Journal of the National Cancer Institute 106, dju215 (2014).
123) Williams, K. E., Bundred, N. J., Landberg, G., Clarke, R. B. & Farnie, G. Focal adhesion kinase and Wnt signaling regulate human ductal carcinoma in situ stem cell activity and response to radiotherapy. Stem Cells 33, 327-341 (2015).
124) Yamaguchi, K. et al. A synthetic-lethality RNAi screen reveals an ERK-mTOR co-targeting pro-apoptotic switch in PIK3CA+ oral cancers. Oncotarget 7, 10696-10709 (2016).
125) Yamaguchi, K., Iglesias-Bartolome, R., Wang, Z., Callejas-Valera, J. L., Amornphimoltham, P., Molinolo, A. A., Cohen, E. E., Califano, J. A., Lippman, S. M., Luo, J., et al. (2016). A synthetic-lethality RNAi screen reveals an ERK-mTOR co-targeting pro-apoptotic switch in PIK3CA+ oral cancers. Oncotarget 7, 10696-10709.
126) Yoo, J. H. et al. ARF6 Is an Actionable Node that Orchestrates Oncogenic GNAQ Signaling in Uveal Melanoma. Cancer Cell 29, 889-904 (2016).
127) Yu, F. X. et al. Mutant Gq/11 promote uveal melanoma tumorigenesis by activating YAP. Cancer Cell 25, 822-830 (2014).
128) Yu, F. X., Luo, J., Mo, J. S., Liu, G., Kim, Y. C., Meng, Z., Zhao, L., Peyman, G., Ouyang, H., Jiang, W., et al. (2014a). Mutant Gq/11 promote uveal melanoma tumorigenesis by activating YAP. Cancer Cell 25, 822-830.
129) Yu, F. X., Zhang, K., and Guan, K. L. (2014b). YAP as oncotarget in uveal melanoma. Oncoscience 1, 480-481.
130) Yu, F. X., Zhao, B., and Guan, K. L. (2015). Hippo Pathway in Organ Size Control, Tissue Homeostasis, and Cancer. Cell 163, 811-828.
131) Zhao, B. et al. TEAD mediates YAP-dependent gene induction and growth control. Genes Dev 22, 1962-1971 (2008).
132) Zhao, B., Ye, X., Yu, J. D., Li, L., Li, W. Q., Li, S. M., Yu, J. J., Lin, J. D., Wang, C. Y., Chinnaiyan, A. M., et al. (2008). TEAD mediates YAP-dependent gene induction and growth control. Gene Dev 22, 1962-1971.

What is claimed is:

1. A method for treating primary or metastatic uveal melanoma (UM) in a subject in need thereof comprising administering an effective amount of a first agent that inhibits expression of focal adhesion kinase (FAK) and a second agent that inhibits mitogen-activated protein kinase kinase (MEK), wherein the first agent is one or more of: PF-562271, VS-4718, NVP-TAC544, TAE226, VS-6063, 1H-Pyrrolo(2,3-b)pyridine, Y15 (1,2,4,5-benzenetetraamine tetrahydrochloride), chloropyramine hydrochloride, R2, Y11, PF-562,271, or GSK2256098 and wherein the second agent is one or more of: selumetinib, trametinib, cobimetinib, CH5126766, Binimetinib, AZD-8330, PD-325901, CI-1040, or TAK-733.

2. The method of claim 1, wherein the UM of the subject has one or more of: a deficient GTPase, a constitutively active Gαq protein, an increased expression of Yes-Associated Protein (YAP), a nuclear-localized YAP, an increased phosphorylation of YAP at Y357, a decreased phosphorylation of YAP at S127, a reduced expression of BAP1, or an increased expression of FAK protein.

3. A method for treating primary or metastatic uveal melanoma (UM) in a subject in need thereof comprising administering an effective amount of a first agent that inhibits expression of focal adhesion kinase (FAK) and a second agent that inhibits mitogen-activated protein kinase kinase (MEK), wherein the first agent is VS-4718 and the second agent is trametinib or CH5126766.

4. A method for treating primary or metastatic uveal melanoma (UM) in a subject in need thereof comprising administering an effective amount of a first agent that inhibits expression of focal adhesion kinase (FAK) and a second agent that inhibits mitogen-activated protein kinase kinase (MEK), wherein the first agent is VS-6063 and the second agent is CH5126766.

5. The method of claim 1, wherein the subject in need thereof is a mammal.

6. The method of claim 5, wherein the mammal is human being.

7. The method of claim 1, wherein the administering an effective amount of the first agent and the second agent comprises one or more of: oral, topical, transdermal, intranasal, vaginal, rectal, subcutaneous intravenous, intraarterial, intramuscular, intraosseous, intraperitoneal, intraocular, subconjunctival, sub-Tenon's, intravitreal, retrobulbar, intracameral, intratumoral, epidural and intrathecal.

8. The method of claim 1, wherein the administering an effective amount of the first agent and the second agent occurs simultaneously.

9. A method for selecting a subject having uveal melanoma (UM) or suspected of having uveal melanoma for treatment with the method of claim 1, the method comprising one or more of the following: 1) determining if a biological sample isolated from the subject has or is characterized as: a deficient GTPase, 2) a constitutively active Gαq protein, 3) an increased expression of Yes-Associated Protein (YAP), 4) a nuclear-localized YAP, 5) an increased phosphorylation of YAP at Y357, 6) a decreased phosphorylation of YAP at S127, 7) a reduced expression of BAP1, or 8) an increased expression of FAK protein.

* * * * *

UNITED STATES PATENT AND TRADEMARK OFFICE
CERTIFICATE OF CORRECTION

PATENT NO. : 11,679,113 B2
APPLICATION NO. : 16/824639
DATED : June 20, 2023
INVENTOR(S) : Jorge Gutkind et al.

Page 1 of 1

It is certified that error appears in the above-identified patent and that said Letters Patent is hereby corrected as shown below:

In the Claims

At Column 73, Line 54: replace "Gaq protein" with --G$\alpha$q protein--

At Column 74, Line 65: replace "Gaq protein" with --G$\alpha$q protein--

Signed and Sealed this
Ninth Day of January, 2024

*Katherine Kelly Vidal*
Katherine Kelly Vidal
*Director of the United States Patent and Trademark Office*